United States Patent
Gray et al.

(10) Patent No.: US 12,234,220 B2
(45) Date of Patent: Feb. 25, 2025

(54) IMMUNOMODULATORY COMPOUNDS

(71) Applicant: DANA-FARBER CANCER INSTITUTE, INC., Boston, MA (US)

(72) Inventors: Nathanael Gray, Boston, MA (US); Tinghu Zhang, Brookline, MA (US); Eric Fischer, Chestnut Hill, MA (US); Alyssa Verano, Allston, MA (US); Zhixiang He, Brookline, MA (US); Guangyan Du, Jamaica Plain, MA (US); Katherine Donovan, Boston, MA (US); Radoslaw Nowak, Boston, MA (US); Jing Ting Christine Yuan, Brookline, MA (US); Hu Liu, Newton, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 952 days.

(21) Appl. No.: 17/255,738

(22) PCT Filed: Jun. 27, 2019

(86) PCT No.: PCT/US2019/039509
§ 371 (c)(1),
(2) Date: Dec. 23, 2020

(87) PCT Pub. No.: WO2020/006233
PCT Pub. Date: Jan. 2, 2020

(65) Prior Publication Data
US 2021/0284624 A1 Sep. 16, 2021

Related U.S. Application Data

(60) Provisional application No. 62/692,176, filed on Jun. 29, 2018.

(51) Int. Cl.
*C07D 401/12* (2006.01)

(52) U.S. Cl.
CPC ................................ *C07D 401/12* (2013.01)

(58) Field of Classification Search
CPC .................................................... C07D 401/12
See application file for complete search history.

(56) References Cited

U.S. PATENT DOCUMENTS

| 5,698,579 A | 12/1997 | Muller |
| 5,877,200 A | 3/1999 | Muller |

(Continued)

FOREIGN PATENT DOCUMENTS

| WO | WO2008/007979 | * | 1/2008 |
| WO | 2017161119 A1 | | 9/2017 |

(Continued)

OTHER PUBLICATIONS

Yuan et al. CAS: 145:249510, 2006.*

(Continued)

*Primary Examiner* — Rei Tsang Shiao
(74) *Attorney, Agent, or Firm* — ArentFox Schiff LLP; Daniel W. Clarke; Shawn P. Foley

(57) ABSTRACT

Disclosed are immunomodulatory compounds, pharmaceutical compositions containing them, and methods of making and using the compounds to treat diseases and disorders characterized by aberrant protein activity that can be targeted by cereblon.

42 Claims, 1 Drawing Sheet

(56) References Cited

U.S. PATENT DOCUMENTS

| | | | |
|---|---|---|---|
| 2018/0215731 A1 | 8/2018 | Crew et al. | |
| 2019/0076539 A1* | 3/2019 | Phillips | C07D 401/12 |

FOREIGN PATENT DOCUMENTS

| | | |
|---|---|---|
| WO | 2017197051 A1 | 11/2017 |
| WO | 2019043214 A1 | 3/2019 |
| WO | 2019140387 A1 | 7/2019 |

OTHER PUBLICATIONS

Palmer et al. CAS: 148: 168597, 2008.*
Phillips et al. CAS: 168:4549, 2017.*
Crew et al. CAS: 169:243035, 2018.*
CAS No. 1333622-73-3.
CAS No. 1489856-35-0.
El-Zanfally, S. et al. "Derivatives of Glutarimide Likely to Possess Therapeutic Activity", Journal of Pharmaceutical Sciences, 1965, 54(3):467-469.
Pubchem CID 65956110 Create Date: Oct. 24, 2012.
CAS No. 1485736-82-0, create date: Dec. 2, 2013, 3-pyridinecarboxamide, N-(2,6-dioxo-3-piperidinyl)-1,2-dihydro-4,6-dimethyl-2-oxo.
CAS No. 2174361-01-2, create date: Feb. 16, 2018, Urea, N-(2,6-dioxo-3-piperidinyl)-N'-[3-methoxy-4-(2-oxo-1-pyrrolidinyl)phenyl].
CAS No. 2175321-89-6, create date: Feb. 18, 2018, Urea, N-(2,6-dioxo-3-piperidinyl)-N'-(2-ethyl-2-methyl-1,3-benzodioxol-5-yl).
CAS No. 2175274-04-9, create date: Feb. 18, 2018, Urea, N-(2,3-dihydro-1,4-benzodioxol-6-yl)-N'-(2,6-dioxo-3-piperidinyl).
CAS No. 1786100-02-4, create date: Jun. 22, 2015, Urea, N-(2,6-dioxo-3-piperidinyl)-N'-2-pyridinyl.
CAS No. 1468002-51-8, create date: Nov. 3, 2013, 4-pyridinecarboxamide, 2-amino-6-chloro-N-(2,6-dioxo-3-piperidinyl).
CAS No. 1492264-76-2, create date: Dec. 11, 2013, 4-pyridinecarboxamide, 2,6-dichloro-N-(2,6-dioxo-3-piperidinyl).
CAS No. 1497183-05-7, create date: Dec. 17, 2013, 1-isoquinolinecarboxamide, N-(2,6-dioxo-3-piperidinyl).
CAS No. 1967286-38-9, create date: Aug. 5, 2016, 4-pyridinecarboxamide, N-(2,6-dioxo-3-piperidinyl)-3-methoxy.
CAS No. 1967313-34-3, create date: Aug. 5, 2016, 4-pyridinecarboxamide, 2-amino-N-(2,6-dioxo-3-piperidinyl)-3-fluoro.
CAS No. 1967312-18-0, create date: Aug. 5, 2016, 4-pyridinecarboxamide, 2-amino-N-(2,6-dioxo-3-piperidinyl)-2-(ethylamino)-3-fluoro.
CAS No. 1967299-94-0, create date: Aug. 5, 2016, 4-pyridinecarboxamide, 2-amino-N-(2,6-dioxo-3-piperidinyl)-3-fluoro-2-(methylamino).
CAS No. 1911130-46-5, create date: May 16, 2016, 2-pyridinecarboxamide, 6-bromo-N-(2,6-dioxo-3-piperidinyl).
CAS No. 1706818-13-4, create date: May 18, 2015, 3-pyridinecarboxamide, N-(2,6-dioxo-3-piperidinyl)-1,2-dihydro-4,6-dimethyl-2-oxo.
Pubchem CID 348822367, create date: Dec. 18, 2017, 1-(2,6-dioxopiperidin-3-yl)-3-phenylurea.
Pubchem CID 132353847, create date: Mar. 2, 2018, N-(2,6-dioxopiperidin-3-yl)-5-phenylpyridine-2-carboxamide.

* cited by examiner

IMMUNOMODULATORY COMPOUNDS

RELATED APPLICATIONS

This application is a national stage application, filed under 35 U.S.C. § 371, of International Application No. PCT/US2019/039509, filed Jun. 27, 2019, which claims the benefit of priority under 35 U.S.C. § 119(e) to U.S. Provisional Application No. 62/692,176, filed on Jun. 29, 2018, each of which is incorporated herein by reference in its entirety.

GOVERNMENT LICENSE RIGHTS

This invention was made with government support under grant number R01CA214608 awarded by the National Institutes of Health. The government has certain rights in the invention.

BACKGROUND OF THE INVENTION

The gene that encodes cereblon (CRBN) was first identified in the course of a study of genes related to memory and learning; the gene was assigned the name CRBN based on its supposed role in the development of cerebral tissues and because its expression in the hippocampus among other areas, is associated with memory and learning processes. Higgins, et al., Neurol. 63(10):1927-31 (2004).

Cereblon is a 442-amino acid multifunctional protein located in the cytoplasm, nucleus and peripheral membrane of the human brain and other tissues (Wada et al., Biochem. & Biophys. Res. Comm. 477:388-94 (2016)). It interacts with the DNA damage-binding protein-1 (DDB1), Cullin 4 (Cul4A and Cul4B), and regulator of Cullins 1 (RoC1) to form the functional E3 ubiquitin ligase complex, which is known as the CRL4$^{CRBN}$ E3 ubiquitin ligase complex. Cereblon's role as part of this complex includes targeting proteins for proteolysis (degradation) via a ubiquitin-proteasome pathway. See, e.g., Chang et al., Int. J. Biochem. Mol. Biol. 2(3):287-94 (2011).

Cereblon is closely associated with the metabolism and proliferation of normal cells as well as tumor cells. On one hand, its existence ensures normal metabolic function and normal physiological function of ion channels, which are important to maintaining cell growth and proliferation. On the other hand, cereblon is also involved in the occurrence of many diseases, such as cancer. See, generally, Shi et al., J. Immunol. Res. Article ID 9130608 (2017).

Immunomodulatory drugs ("IMiDs"). are a new class of anti-cancer drugs that are derived from thalidomide, a drug which has been approved by the FDA for treatment of multiple myeloma. In addition to thalidomide itself, two thalidomide analogs, lenalidomide and pomalidomide, have been approved by the FDA (and are being marketed under the names REVLIMID® and POMALYST®, respectively) for treatment of multiple myeloma (among other diseases). As suggested by their nomenclature, one of the first known properties of IMiDs was their immunomodulatory capacity, including cytokine modulation and T cell co-stimulation (Schafer et al., J. Pharmacol. & Exper. Ther. 305:1222-32 (2003)), resulting in interleukin-2 production in T cells. Subsequently, IMiDs were shown to have pleiotropic effects on a wide range of immune cells including natural killer (NK) cell activation and B cell and monocyte inhibition (Corral et al., J. Immunol. 163:380-6 (1999)).

Cereblon has been identified as a common primary target for IMiDs. For example, it has been reported that members of the Ikaros family of transcription factors, Ikaros and Aiolos (encoded by the genes Ikaros family zinc finger protein 1 (IKZF1) and IKZF3 respectively) are recruited as protein substrates for CRL4$^{CRBN}$ in T cells in response to treatment with lenalidomide and pomalidomide, resulting in enhanced production of IL-2 and other cytokines that regulate T cell function. See, Gandhi et al., Br. J. Hematol. 164:811-21 (2014). It has also been reported that lenalidomide, but not pomalidomide, induces the degradation of the protein kinase, casein kinase 1α (CK1α), which exploits CK1a haploinsufficiency associated with 5q-deletion associated myelodysplastic syndrome. See, Krönke et al., Nature 523:183-8 (2015). Structural studies have shown that these IMiDs bind in a shallow hydrophobic pocket on the surface of cereblon, and that the binding is mediated by the glutarimide ring that is common to thalidomide, lenalidomide and pomalidomide.

More recently, CRBN-binding compounds named "cereblon modulators" have been developed. For example, CC-122, a new chemical entity termed 'pleiotropic pathway modifier', binds cereblon and promotes degradation of Aiolos and Ikaros in diffuse large B-cell lymphoma (DLBCL) and T cells in vitro, in vivo, and in patients, resulting in both cell autonomous as well as immunostimulatory effects. See, Hagner et al., Blood 126(6):779-89 (2016). CC-885, another new cereblon modulator, has been reported to possess antitumor activity which is broader than that of thalidomide, lenalidomide and pomalidomide. CC-885 is mediated by cereblon-dependent ubiquitination and degradation of the translation termination factor glutathione S-transferase pi gene (GSTP1). See, Matyskiela et al., Nature 535:252 (2016).

The exploitation of cereblon as a mediator in disease treatment has also led to the development of hetero-bifunctional PROTACs (PROteolysis TArgeting Chimera) that recruit targeted proteins that are themselves disease mediators (e.g., bromodomain-containing protein 4 (BRD4)) to CRL4$^{CRBN}$ E3 ubiquitin ligase, leading to degradation of the targeted protein. See, e.g., Lu et al, Cell Cancer Biol. 22(6):755-63 (2015).

SUMMARY OF THE INVENTION

A first aspect of the present invention is directed to a compound having a structure represented by formula (I):

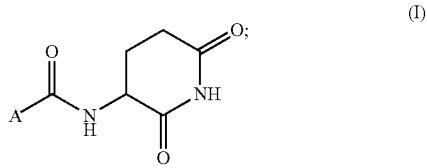

wherein A represents A$_1$, A$_2$, A$_3$, A$_4$ or A$_5$:

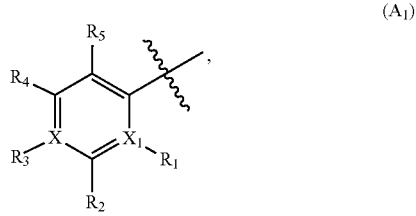

wherein X and $X_1$ independently represent C or N, provided that one of X and $X_1$ represents N; wherein $R_1$ is absent if $X_1$ represents N, and if $X_1$ represents C, $R_1$ represents H, or together with $R_2$ and the other atoms to which they are bound form an optionally substituted 5- or 6-membered carbocyclic group (e.g., an optionally substituted phenyl group) or an optionally substituted 5- or 6-membered heterocyclic group (e.g., an optionally substituted 5- or 6-membered heteroaryl group);

$R_2$ represents H, halo, hydroxy, optionally substituted C1-C4 alkoxy, 1-benzyl-4-piperidinoxy, optionally substituted 5- or 6-membered carbocyclic group, optionally substituted 5- or 6-membered heterocyclic group, optionally substituted aryl (which as defined herein embraces aralkyl and aralkoxy), optionally substituted heteroaryl (which as defined herein embraces heteroaralkyl and heteroaralkoxy), or $NR_6R_7$, wherein each of $R_6$ and $R_7$ independently represents H or a substituent (e.g., optionally substituted amine (e.g., $NH_2$), optionally substituted C1-C4 alkyl, optionally substituted C1-C4 alkoxy, optionally substituted aryl, optionally substituted heteroaryl), or $R_2$ together with $R_1$ and the other atoms to which they are bound form an optionally substituted 5- or 6-membered carbocyclic group (e.g., an optionally substituted phenyl group) or an optionally substituted 5- or 6-membered heterocyclic group (e.g., an optionally substituted 5- or 6-membered heteroaryl group);

if X represents N, $R_3$ is absent, and if X represents C, $R_3$ independently represents H, halo, optionally substituted amine (e.g., $NH_2$), hydroxy, optionally substituted C1-C4 alkoxy, 1-benzyl-4-piperidinoxy, optionally substituted 5- or 6-membered carbocyclic group, optionally substituted 5- or 6-membered heterocyclic group, optionally substituted aryl, optionally substituted heteroaryl, or $NR_6R_7$, or wherein $R_2$ and $R_3$, or $R_3$ and $R_4$, together with the atoms to which they are bound form an optionally substituted 5- or 6-membered carbocyclic group (e.g., an optionally substituted phenyl group) or an optionally substituted 5- or 6-membered heterocyclic group (e.g., an optionally substituted 5- or 6-membered heteroaryl group);

$R_4$, and $R_5$ each independently represents H, halo, optionally substituted amine (e.g., $NH_2$), hydroxy, optionally substituted C1-C4 alkoxy, 1-benzyl-4-piperidinoxy, an optionally substituted 5- or 6-membered carbocyclic group, an optionally substituted 5- or 6-membered heterocyclic group, optionally substituted aryl, optionally substituted heteroaryl, or $NR_6R_7$, or wherein $R_4$ and $R_5$, together with the atoms to which they are bound form an optionally substituted 5- or 6-membered carbocyclic group (e.g., an optionally substituted phenyl group) or an optionally substituted 5- or 6-membered heterocyclic group (e.g., an optionally substituted 5- or 6-membered heteroaryl group);

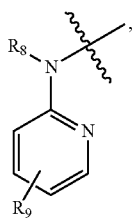

(A₂)

wherein $R_8$ represents H, optionally substituted C1-C4 alkyl, optionally substituted amine (e.g., $NH_2$), optionally substituted C1-C4 alkoxy, or an optionally substituted 5- or 6-membered carbocyclic group (e.g., an optionally substituted phenyl group) or an optionally substituted 5- or 6-membered heterocyclic group (e.g., an optionally substituted 5- or 6-membered heteroaryl group), and $R_9$ represents H, halo (e.g., Cl or F), optionally substituted C1-C4 alkyl, optionally substituted amine (e.g., $NH_2$), hydroxy, optionally substituted C1-C4 alkoxy, or an optionally substituted 5- or 6-membered carbocyclic group (e.g., an optionally substituted phenyl group) or an optionally substituted 5- or 6-membered heterocyclic group (e.g., an optionally substituted 5- or 6-membered heteroaryl group);

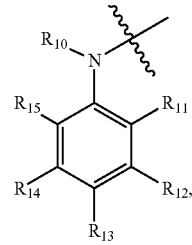

(A₃)

wherein $R_{10}$ represents H, optionally substituted C1-C4 alkyl, optionally substituted amine (e.g., $NH_2$), optionally substituted C1-C4 alkoxy, optionally substituted aryl, or an optionally substituted heteroaryl group, and $R_{11}$, $R_{12}$, $R_{13}$, $R_{14}$, and $R_{15}$ each independently represents H, halo, hydroxy, optionally substituted C1-C4 alkoxy, optionally substituted aryl (which as defined herein embraces aralkyl and aralkoxy), optionally substituted heteroaryl (which as defined herein embraces heteroaralkyl and heteroaralkoxy), or $NR_6R_7$, wherein each of $R_6$ and $R_7$ independently represents H or a substituent (e.g., optionally substituted amine (e.g., $NH_2$), optionally substituted C1-C4 alkyl, optionally substituted C1-C4 alkoxy, optionally substituted aryl, optionally substituted heteroaryl), or $R_{11}$ together with $R_{12}$ and the other atoms to which they are bound form an optionally substituted 5- or 6-membered carbocyclic group (e.g., an optionally substituted phenyl group) or an optionally substituted 5- or 6-membered heterocyclic group (e.g., an optionally substituted 5- or 6-membered heteroaryl group), or $R_{12}$ together with $R_{13}$ and the other atoms to which they are bound form an optionally substituted 5- or 6-membered carbocyclic group (e.g., an optionally substituted phenyl group) or an optionally substituted 5- or 6-membered heterocyclic group (e.g., an optionally substituted 5- or 6-membered heteroaryl group), or $R_{13}$ together with $R_{14}$ and the other atoms to which they are bound form an optionally substituted 5- or 6-membered carbocyclic group (e.g., an optionally substituted phenyl group) or an optionally substituted 5- or 6-membered heterocyclic group (e.g., an optionally substituted 5- or 6-membered heteroaryl group), or $R_{14}$ together with $R_{15}$ and the other atoms to which they are bound form an optionally substituted 5- or 6-membered carbocyclic group (e.g., an optionally substituted phenyl group) or an optionally substituted 5- or 6-membered heterocyclic group (e.g., an optionally substituted 5- or 6-membered heteroaryl group);

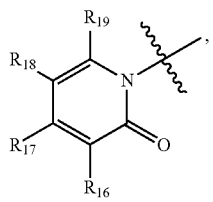

(A4)

wherein $R_{16}$, $R_{17}$, $R_{18}$ and $R_{19}$ independently represent H or a substituent, (e.g., optionally substituted amine (e.g., $NH_2$), hydroxy, optionally substituted C1-C4 alkyl, optionally substituted C1-C4 alkoxy, optionally substituted aryl, optionally substituted heteroaryl) or wherein $R_{16}$ and $R_{17}$ together with the atoms to which they are bound form an optionally substituted 5- or 6-membered carbocyclic group (e.g., optionally substituted phenyl group), an optionally substituted 5- or 6-membered heterocyclic group (e.g., an optionally substituted 5- or 6-membered heteroaryl group), or wherein $R_{17}$ and $R_{18}$ together with the atoms to which they are bound form an optionally substituted 5- or 6-membered carbocyclic group (e.g., a phenyl group), an optionally substituted 5- or 6-membered heterocyclic group (e.g., a 5- or 6-membered heteroaryl group), or wherein $R_{18}$ and $R_{19}$ together with the atoms to which they are bound form an optionally substituted 5- or 6-membered carbocyclic group (e.g., a phenyl group), or an optionally substituted 5- or 6-membered heterocyclic group (e.g., a 5- or 6-membered heteroaryl group); or

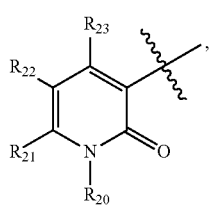

(A5)

wherein $R_{20}$, $R_{21}$, $R_{22}$ and $R_{23}$ independently represent H or a substituent (e.g., optionally substituted amine (e.g., $NH_2$), hydroxy, optionally substituted C1-C4 alkyl, optionally substituted C1-C4 alkoxy, optionally substituted aryl, optionally substituted heteroaryl), or wherein $R_{20}$ and $R_{21}$ together with the atoms to which they are bound form an optionally substituted 5- or 6-membered heterocyclic group, or wherein $R_{21}$ and $R_{22}$ together with the atoms to which they are bound form an optionally substituted 5- or 6-membered carbocyclic group (e.g., a phenyl group), an optionally substituted 5- or 6-membered heterocyclic group (e.g., a 5- or 6-membered heteroaryl group), or wherein $R_{22}$ and $R_{23}$ together with the atoms to which they are bound form an optionally substituted 5- or 6-membered carbocyclic group (e.g., a phenyl group), or an optionally substituted 5- or 6-membered heterocyclic group (e.g., a 5- or 6-membered heteroaryl group); or a pharmaceutically acceptable salt or stereoisomer thereof.

In some embodiments wherein A is $A_1$, not all of $R_2$, $R_3$, $R_4$, and $R_5$ represents H. In some embodiments, such as when X represents N, all of $R_1$, $R_2$, $R_4$ and $R_5$ represent H. In some embodiments, such as when $X_1$ represents N, all of $R_2$, $R_3$, $R_4$ and $R_5$ represent H. In some embodiments, one of $R_2$, $R_3$, $R_4$, and $R_5$ represents a substituted benzyloxy group (e.g., 4-[[4(oxymethyl)phenyl]methyl]morpholine) or halo (e.g., Cl).

In some embodiments wherein A is $A_2$, $R_8$ is H or methyl, and $R_9$ is H, hydroxy, $NH_2$ or halo (e.g., Cl).

In some embodiments wherein A is $A_3$, $R_{10}$ is H or methyl, and $R_{11}$ and $R_{12}$ together with the atoms to which they are bound form an optionally substituted 5-membered heterocyclic group.

In some embodiments, one of $R_2$, $R_3$, $R_4$, and $R_5$ represents C5-C6 heterocyclic substituted benzyl or 1-benzyl-4-piperidinoxy.

In some embodiments wherein A is $A_4$, $R_{16}$ and $R_{17}$ together with the atoms to which they are bound form an optionally substituted phenyl group. In some embodiments, $R_{17}$ and $R_{18}$ together with the atoms to which they are bound form an optionally substituted phenyl group. In some embodiments, $R_{18}$ and $R_{19}$ together with the atoms to which they are bound form an optionally substituted phenyl group. In some embodiments, the phenyl group is unsubstituted.

In some embodiments, wherein A is $A_5$, $R_{20}$ is H, methyl, phenyl or benzyl, and $R_{21}$, $R_{22}$, and $R_{23}$ are H.

Another aspect of the present invention is directed to a pharmaceutical composition that includes a therapeutically effective amount of a compound of formula (I) or a pharmaceutically acceptable salt or stereoisomer thereof and a pharmaceutically acceptable carrier.

A further aspect of the present invention is directed to a method for making a compound of formula (I) or a pharmaceutically acceptable salt or stereoisomer thereof.

A further aspect of the present invention is directed to methods of treating diseases or disorders involving aberrant (e.g., dysregulated) protein activity, that entails administration of a therapeutically effective amount of a compound of formula (I) or a pharmaceutically acceptable salt or a stereoisomer thereof to a subject in need thereof.

The inventive compounds lack the pyrrolidine-2-one or pyrrolidine-2,5-dione ring that is common to thalidomide, lenalidomide, and pomalidomide. Applicant has surprisingly and unexpectedly discovered that even without the pyrrolidine-2-one or pyrrolidine-2,5-dione ring, the inventive compounds have affinity for cereblon and may thus exhibit cereblon modulatory activity and function as immunomodulatory therapeutics. Without intending to be bound by any particular theory of operation, Applicant believes that the compounds effect binding to cereblon at least in part due to intramolecular hydrogen bonding between the NH group and the N atom of the pyridine ring.

Also without intending to be bound by any theory of operation, Applicant believes that the compounds of the present invention exert their therapeutic (e.g., anti-cancer) effects or benefits by a combination of anti-proliferative and immunomodulatory effects. In particular, it is believed that the binding of the compounds to cereblon confers a differentiated substrate specificity on $CRL4^{CRBN}$ E3 ubiquitin ligase. This diversified substrate specificity substantially enlarges the types and numbers of potential targets, thus offering a wide range of therapeutic applications. For example, in addition to or aside from the expression products of IKZF1, and IKZF3, and CK1a, compounds of the present invention may indirectly target a host of different substrates for cereblon-dependent ubiquitination and degradation. Such substrates may include, for example, family with sequence similarity 83 member F (FAM83F), DTW domain containing 1 (DTWD1), IKZF2, IKZF4, IKZF5, zinc finger protein 91 homolog (ZFP91), ZFP62, ZFP36 ring finger protein like (ZFP36L2), ring finger protein 166 (RNF166), Ras-related protein Rab-28 (RAB28), glutathione S-transferase pi 1 (GSTP1), GSPT2, mitochondrial import inner membrane translocase subunit Tim10 (TIMM10), GDNF inducible zinc finger protein 1 (GZF1), early growth response 1 (EGR1), hypermethylated in cancer 1 (HIC1), HIC2, insulinoma-associated protein 2 (INSM2), odd-skipped related transcription factor 2 (OSR2), protein polybromo-1 (PB1), PR domain zinc finger protein 15 (PRD15), spalt like transcription factor 1 (SALL1), SALL3, SALL4, WIZ, zinc finger and BTB domain-containing protein 17 (ZBT17), ZBTB39, ZBT41, ZBT49, ZBT7A, ZBT7B, ZBTB2, zinc finger protein interacting with K protein 1 (ZIK1), zinc finger protein 3 (ZNF3), ZNF217, ZNF276, ZNF316, ZNF324B, ZNF335, ZNF397, ZNF407, ZNF408, ZNF462, ZNF483, SNF517, ZNF526, ZNF581, ZNF587, ZNF589, ZNF618, ZNF644, ZNF646, ZNF653, ZN6F54, ZNF692, ZNF724, ZNF771, ZNF782, ZNF784, ZNF814, zinc finger and SCAN domain containing 10 (ZSC10), ZSC22, ZC827, and zinc finger with UFM1-specific peptidase domain (ZUFSP).

Some of these targets might not be "druggable" in the sense of being directly targeted by any current generation of IMiDs. Thus, the inventive compounds may be further advantageous relative to the cereblon-targeted degraders which due to their large flexible linkers can cause pharmacokinetic challenges.

DETAILED DESCRIPTION OF THE INVENTION

Figure 1A:
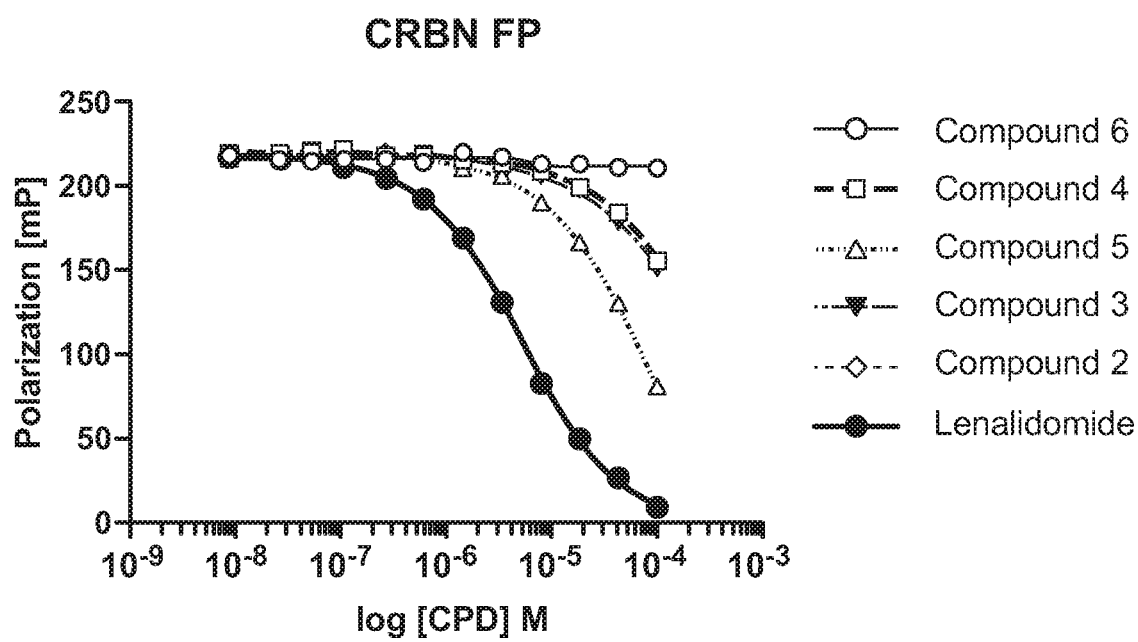
FIG. 1A is a graph that shows cereblon binding (expressed in polarization mP) by various inventive immunomodulatory compounds (inventive compounds 2-6) as compared to a control (lenalidomide).

Unless defined otherwise, all technical and scientific terms used herein have the same meaning as is commonly understood by one of skill in the art to which the subject matter herein belongs. As used in the specification and the appended claims, unless specified to the contrary, the following terms have the meaning indicated in order to facilitate the understanding of the present invention.

As used in the description and the appended claims, the singular forms "a", "an", and "the" include plural referents unless the context clearly dictates otherwise. Thus, for example, reference to "a composition" includes mixtures of two or more such compositions, reference to "an inhibitor" includes mixtures of two or more such inhibitors, and the like.

Unless stated otherwise, the term "about" means within 10% (e.g., within 5%, 2% or 1%) of the particular value modified by the term "about."

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

With respect to compounds of the present invention, and to the extent the following terms are used herein to further describe them, the following definitions apply.

As used herein, the term "aliphatic" refers to a non-cyclic hydrocarbon group and includes branched and unbranched, alkyl, alkenyl, or alkynyl groups.

As used herein, the term "alkyl" refers to a saturated linear or branched-chain monovalent hydrocarbon radical. In one embodiment, the alkyl radical is a $C_1$-$C_{18}$ group. In other embodiments, the alkyl radical is a $C_0$-$C_6$, $C_0$-$C_5$, $C_0$-$C_3$, $C_1$-$C_{12}$, $C_1$-$C_8$, $C_1$-$C_6$, $C_1$-$C_5$, $C_1$-$C_4$ or $C_1$-$C_3$ group (wherein $C_0$ alkyl refers to a bond). Examples of alkyl groups include methyl, ethyl, 1-propyl, 2-propyl, i-propyl, 1-butyl, 2-methyl-1-propyl, 2-butyl, 2-methyl-2-propyl, 1-pentyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, heptyl, octyl, nonyl, decyl, undecyl and dodecyl. In some embodiments, an alkyl group is a $C_1$-$C_3$ alkyl group. In some embodiments, an alkyl group is a $C_1$-$C_2$ alkyl group.

As used herein, the term "alkylene" refers to a straight or branched divalent hydrocarbon chain linking the rest of the molecule to a radical group, consisting solely of carbon and hydrogen, containing no unsaturation and having from one to 12 carbon atoms, for example, methylene, ethylene, propylene, n-butylene, and the like. The alkylene chain may be attached to the rest of the molecule through a single bond and to the radical group through a single bond. In some embodiments, the alkylene group contains one to 8 carbon atoms ($C_1$-$C_8$ alkylene). In other embodiments, an alkylene group contains one to 5 carbon atoms ($C_1$-$C_5$ alkylene). In other embodiments, an alkylene group contains one to 4 carbon atoms ($C_1$-$C_4$ alkylene). In other embodiments, an alkylene contains one to three carbon atoms ($C_1$-$C_3$ alkylene). In other embodiments, an alkylene group contains one to two carbon atoms ($C_1$-$C_2$ alkylene). In other embodiments, an alkylene group contains one carbon atom ($C_1$ alkylene).

As used herein, the term "haloalkyl" refers to an alkyl group as defined herein that is substituted with one or more (e.g., 1, 2, 3, or 4) halo groups.

As used herein, the term "alkenyl" refers to a linear or branched-chain monovalent hydrocarbon radical with at least one carbon-carbon double bond. An alkenyl includes radicals having "cis" and "trans" orientations, or alternatively, "E" and "Z" orientations. In one example, the alkenyl radical is a $C_2$-$C_{18}$ group. In other embodiments, the alkenyl radical is a $C_2$-$C_{12}$, $C_2$-$C_{10}$, $C_2$-$C_8$, $C_2$-$C_6$ or $C_2$-$C_3$ group. Examples include ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

As used herein, the term "alkynyl" refers to a linear or branched monovalent hydrocarbon radical with at least one carbon-carbon triple bond. In one example, the alkynyl radical is a $C_2$-$C_{18}$ group. In other examples, the alkynyl radical is $C_2$-$C_{12}$, $C_2$-$C_{10}$, $C_2$-$C_8$, $C_2$-$C_6$ or $C_2$-$C_3$. Examples include ethynyl prop-1-ynyl, prop-2-ynyl, but-1-ynyl, but-2-ynyl and but-3-ynyl.

As used herein, the term "aldehyde" is represented by the formula —C(O)H. The terms "C(O)" and C=O are used interchangeably herein.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl.

As used herein, the term "halogen" (or "halo" or "halide") refers to fluorine, chlorine, bromine, or iodine.

As used herein, the term "carboxylic acid" is represented by the formula —C(O)OH, and a "carboxylate" is represented by the formula —C(O)O—.

As used herein, the term "ester" is represented by the formula —OC(O)$Z^1$ or —C(O)O$Z^1$, where $Z^1$ may be an alkyl, halogenated alkyl, alkenyl, alkynyl, aryl, heteroaryl, cycloalkyl, cycloalkenyl, heterocycloalkyl, or heterocycloalkenyl group, all as described herein.

As used herein, the term "ether" is represented by the formula $Z^1OZ^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group, all as described herein.

As used herein, the term "ketone" is represented by the formula $Z^1C(O)Z^2$, where $A^1$ and $A^2$ independently represent alkyl, halogenated alkyl, alkenyl, alkynyl, aryl, heteroaryl, cycloalkyl, cycloalkenyl, heterocycloalkyl, or heterocycloalkenyl group, all as described herein.

As used herein, the term "sulfonyl" refers to the sulfo-oxo group represented by the formula —S(O)$_2Z^1$, where $Z^1$ may be hydrogen, an alkyl, halogenated alkyl, alkenyl, alkynyl, aryl, heteroaryl, cycloalkyl, cycloalkenyl, heterocycloalkyl, or heterocycloalkenyl group, all as described herein.

As used herein, the term "sulfonylamino" (or "sulfonamide") is represented by the formula —S(O)$_2NH_2$.

As used herein, the term "thiol" is represented by the formula —SH.

As used herein, the term "cyclic group" broadly refers to any group that used alone or as part of a larger moiety, contains a saturated, partially saturated or aromatic ring system e.g., carbocyclic (cycloalkyl, cycloalkenyl), heterocyclic (heterocycloalkyl, heterocycloalkenyl), aryl and heteroaryl groups. Cyclic groups may have one or more (e.g., fused) ring systems. Thus, for example, a cyclic group can contain one or more carbocyclic, heterocyclic, aryl or heteroaryl groups.

As used herein, the term "carbocyclic" (also "carbocyclyl") refers to a group that used alone or as part of a larger moiety, contains a saturated, partially unsaturated, or aromatic ring system having 3 to 20 carbon atoms, that is alone or part of a larger moiety (e.g., an alkcarbocyclic group). The term carbocyclyl includes mono-, bi-, tri-, fused, bridged, and spiro-ring systems, and combinations thereof. In one embodiment, carbocyclyl includes 3 to 15 carbon atoms ($C_3$-$C_{15}$). In one embodiment, carbocyclyl includes 3 to 12 carbon atoms ($C_3$-$C_{12}$). In another embodiment, carbocyclyl includes $C_3$-$C_8$, $C_3$-$C_{10}$ or $C_5$-$C_{10}$. In another embodiment, carbocyclyl, as a monocycle, includes $C_3$-$C_8$, $C_3$-$C_6$ or $C_5$-$C_6$. In some embodiments, carbocyclyl, as a bicycle, includes $C_7$-$C_{12}$. In another embodiment, carbocyclyl, as a spiro system, includes $C_5$-$C_{12}$. Representative examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, such as for example bicyclo[2.2.1]heptane, bicyclo[2.2.2]octane, naphthalene, and bicyclo[3.2.2]nonane. Representative examples of spiro carbocyclyls include spiro[2.2]pentane, spiro[2.3]hexane, spiro[2.4]heptane, spiro[2.5]octane and spiro[4.5]decane. The term carbocyclyl includes aryl ring systems as defined herein. The term carbocyyl also includes cycloalkyl rings (e.g., saturated or partially unsaturated mono-, bi-, or spiro-carbocycles). The term carbocyclic group also includes a carbocyclic ring fused to one or more (e.g., 1, 2 or 3) different cyclic groups (e.g., aryl or heterocyclic rings), where the radical or point of attachment is on the carbocyclic ring.

Thus, the term carbocyclic also embraces carbocyclylalkyl groups which as used herein refer to a group of the formula —$R^c$-carbocyclyl where $R^c$ is an alkylene chain. The term carbocyclic also embraces carbocyclylalkoxy groups which as used herein refer to a group bonded through an oxygen atom of the formula —O—$R^c$-carbocyclyl where $R^c$ is an alkylene chain.

As used herein, the term "heterocyclyl" refers to a "carbocyclyl" that used alone or as part of a larger moiety, contains a saturated, partially unsaturated or aromatic ring system, wherein one or more (e.g., 1, 2, 3, or 4) carbon atoms have been replaced with a heteroatom (e.g., O, N, N(O), S, S(O), or S(O)$_2$). The term heterocyclyl includes mono-, bi-, tri-, fused, bridged, and spiro-ring systems, and combinations thereof. In some embodiments, a heterocyclyl refers to a 3 to 15 membered heterocyclyl ring system. In some embodiments, a heterocyclyl refers to a 3 to 12 membered heterocyclyl ring system. In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. The term heterocyclyl also includes $C_3$-$C_8$ heterocycloalkyl, which is a saturated or partially unsaturated mono-, bi-, or spiro-ring system containing 3-8 carbons and one or more (1, 2, 3 or 4) heteroatoms.

In some embodiments, a heterocyclyl group includes 3-12 ring atoms and includes monocycles, bicycles, tricycles and Spiro ring systems, wherein the ring atoms are carbon, and one to 5 ring atoms is a heteroatom such as nitrogen, sulfur or oxygen. In some embodiments, heterocyclyl includes 3- to 7-membered monocycles having one or more heteroatoms selected from nitrogen, sulfur or oxygen. In some embodiments, heterocyclyl includes 4- to 6-membered monocycles having one or more heteroatoms selected from nitrogen, sulfur or oxygen. In some embodiments, heterocyclyl includes 3-membered monocycles. In some embodiments, heterocyclyl includes 4-membered monocycles. In some embodiments, heterocyclyl includes 5-6 membered monocycles. In some embodiments, the heterocyclyl group includes 0 to 3 double bonds. In any of the foregoing embodiments, heterocyclyl includes 1, 2, 3 or 4 heteroatoms. Any nitrogen or sulfur heteroatom may optionally be oxidized (e.g., NO, SO, SO$_2$), and any nitrogen heteroatom may optionally be quaternized (e.g., [NR$_4$]$^+$Cl$^-$, [NR$_4$]$^+$OH$^-$).

Representative examples of heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydropyranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Representative examples of benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are yet other examples of heterocyclyl groups. In some embodiments, a heterocyclic group includes a heterocyclic ring fused to one or more (e.g., 1, 2 or 3) different cyclic groups (e.g., carbocyclic rings or heterocyclic rings), where the radical or point of attachment is on the heterocyclic ring, and in some embodiments wherein the point of attachment is a heteroatom contained in the heterocyclic ring.

Thus, the term heterocyclic embraces N-heterocyclyl groups which as used herein refer to a heterocyclyl group containing at least one nitrogen and where the point of attachment of the heterocyclyl group to the rest of the molecule is through a nitrogen atom in the heterocyclyl group. Representative examples of N-heterocyclyl groups include 1-morpholinyl, 1-piperidinyl, 1-piperazinyl, 1-pyrrolidinyl, pyrazolidinyl, imidazolinyl and imidazolidinyl. The term heterocyclic also embraces C-heterocyclyl groups which as used herein refer to a heterocyclyl group containing at least one heteroatom and where the point of attachment of the heterocyclyl group to the rest of the molecule is through a carbon atom in the heterocyclyl group. Representative examples of C-heterocyclyl radicals include 2-morpholinyl, 2- or 3- or 4-piperidinyl, 2-piperazinyl, and 2- or 3-pyrrolidinyl. The term heterocyclic also embraces heterocyclylalkyl groups which as disclosed above refer to a group of the formula —$R^c$-heterocyclyl where $R^c$ is an alkylene chain. The term heterocyclic also embraces heterocyclylalkoxy groups which as used herein refer to a radical bonded through an oxygen atom of the formula —O—$R^c$-heterocyclyl where $R^c$ is an alkylene chain.

As used herein, the term "aryl" used alone or as part of a larger moiety (e.g., "aralkyl", wherein the terminal carbon atom on the alkyl group is the point of attachment, e.g., a benzyl group), "aralkoxy" wherein the oxygen atom is the point of attachment, or "aroxyalkyl" wherein the point of attachment is on the aryl group) refers to a group that includes monocyclic, bicyclic or tricyclic, carbon ring system, that includes fused rings, wherein at least one ring in the system is aromatic. In some embodiments, the aralkoxy group is a benzoxy group. The term "aryl" may be used interchangeably with the term "aryl ring". In one embodiment, aryl includes groups having 6-18 carbon atoms. In another embodiment, aryl includes groups having 6-10 carbon atoms. Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, and the like, which may be substituted or independently substituted by one or more substituents described herein. A particular aryl is phenyl. In some embodiments, an aryl group includes an aryl ring fused to one or more (e.g., 1, 2 or 3) different cyclic groups (e.g., carbocyclic rings or heterocyclic rings), where the radical or point of attachment is on the aryl ring.

Thus, the term aryl embraces aralkyl groups which as disclosed above refer to a group of the formula —$R^c$-aryl where $R^c$ is an alkylene chain such as methylene or ethylene. In some embodiments, the aralkyl group is an optionally substituted benzyl group. The term aryl also embraces aralkoxy groups which as used herein refer to a group bonded through an oxygen atom of the formula —O—$R^c$-aryl where $R^c$ is an alkylene chain such as methylene or ethylene.

As used herein, the term "heteroaryl" used alone or as part of a larger moiety (e.g., "heteroarylalkyl" (also "heteroaralkyl"), or "heteroarylalkoxy" (also "heteroaralkoxy"), refers to a monocyclic, bicyclic or tricyclic ring system having 5 to 14 ring atoms, wherein at least one ring is aromatic and contains at least one heteroatom. In one embodiment, heteroaryl includes 4-6 membered monocyclic aromatic groups where one or more ring atoms is nitrogen, sulfur or oxygen that is independently optionally substituted. In another embodiment, heteroaryl includes 5-6 membered monocyclic aromatic groups where one or more ring atoms is nitrogen, sulfur or oxygen. Representative examples of heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b]pyridazinyl, purinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5- yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, and pyrid-2-yl N-oxide. The term "heteroaryl" also includes groups in which a heteroaryl is fused to one or more cyclic (e.g., carbocyclyl, or heterocyclyl) rings, where the radical or point of attachment is on the heteroaryl ring. Nonlimiting examples include indolyl, isoindolyl, benzothienyl, benzofuranyl, dibenzofuranyl, indazolyl, benzimidazolyl, benzothiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl and pyrido[2,3-b]-1,4-oxazin-3(4H)-one. A heteroaryl group may be mono-, bi- or tri-cyclic. In some embodiments, a heteroaryl group includes a heteroaryl ring fused to one or more (e.g., 1, 2 or 3) different cyclic groups (e.g., carbocyclic rings or heterocyclic rings), where the radical or point of attachment is on the heteroaryl ring, and in some embodiments wherein the point of attachment is a heteroatom contained in the heterocyclic ring.

Thus, the term heteroaryl embraces N-heteroaryl groups which as used herein refer to a heteroaryl group as defined above containing at least one nitrogen and where the point of attachment of the heteroaryl group to the rest of the molecule is through a nitrogen atom in the heteroaryl group. The term heteroaryl also embraces C-heteroaryl groups which as used herein refer to a heteroaryl group as defined above and where the point of attachment of the heteroaryl group to the rest of the molecule is through a carbon atom in the heteroaryl group. The term heteroaryl also embraces heteroarylalkyl groups which as disclosed above refer to a group of the formula —$R^c$-heteroaryl, where $R^c$ is an alkylene chain as defined above. The term heteroaryl also embraces heteroaralkoxy (or heteroarylalkoxy) groups which as used herein refer to a group bonded through an oxygen atom of the formula —O—$R^c$-heteroaryl, where $R^c$ is an alkylene group as defined above.

Any of the groups described herein may be substituted or unsubstituted. As used herein, the term "substituted" broadly refers to all permissible substituents with the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc. Representative substituents include halogens, hydroxyl groups, and any other organic groupings containing any number of carbon atoms, e.g., 1-14 carbon atoms, and which may include one or more (e.g., 1 2 3, or 4) heteroatoms such as oxygen, sulfur, and nitrogen grouped in a linear, branched, or cyclic structural format.

Representative examples of substituents may thus include alkyl, substituted alkyl, alkoxy, substituted alkoxy, alkenyl, substituted alkenyl, alkynyl, substituted alkynyl, cyclic, substituted cyclic, carbocyclic, substituted carbocyclic, heterocyclic, substituted heterocyclic, aryl (e.g., benzyl and phenyl), substituted aryl (e.g., substituted benzyl or phenyl), heteroaryl, substituted heteroaryl, aralkyl, substituted aralkyl, halo, hydroxyl, aryloxy, substituted aryloxy, alkylthio, substituted alkylthio, arylthio, substituted arylthio, cyano, carbonyl, substituted carbonyl, carboxyl, substituted carboxyl, amino (e.g., $NH_2$), substituted amino, amido, substituted amido, morpholino, sulfonyl, substituted sulfonyl, amino acid, and peptide groups.

Broadly, the present invention is directed to a compound having a structure represented by formula (I):

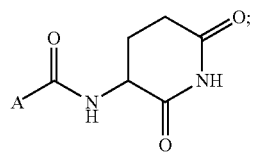

wherein A represents $A_1$, $A_2$, $A_3$, $A_4$ or $A_5$:

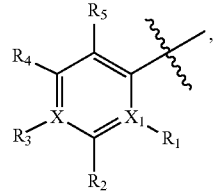

wherein X and $X_1$ independently represent C or N, provided that one of X and $X_1$ represents N; wherein $R_1$ is absent if $X_1$ represents N, and if $X_1$ represents C, $R_1$ represents H, or together with $R_2$ and the other atoms to which they are bound form an optionally substituted 5- or 6-membered carbocyclic group (e.g., an optionally phenyl group) or an optionally substituted 5- or 6-membered heterocyclic group (e.g., an optionally substituted 5- or 6-membered heteroaryl group);

$R_2$ represents H, halo, hydroxy, optionally substituted C1-C4 alkoxy, 1-benzyl-4-piperidinoxy, optionally substituted 5- or 6-membered carbocyclic group, optionally substituted 5- or 6-membered heterocyclic group, optionally substituted aryl (which as defined herein embraces aralkyl and aralkoxy), optionally substituted heteroaryl (which as defined herein embraces heteroaralkyl and heteroaralkoxy), or $NR_6R_7$, wherein each of $R_6$ and $R_7$ independently represents H or a substituent (e.g., optionally substituted amine (e.g., $NH_2$), optionally substituted C1-C4 alkyl, optionally substituted C1-C4 alkoxy, optionally substituted aryl, optionally substituted heteroaryl), or $R_2$ together with $R_1$ and the other atoms to which they are bound form an optionally substituted 5- or 6-membered carbocyclic group (e.g., an optionally substituted phenyl group) or an optionally substituted 5- or 6-membered heterocyclic group (e.g., an optionally substituted 5- or 6-membered heteroaryl group);

if X represents N, $R_3$ is absent, and if X represents C, $R_3$ independently represents H, halo, hydroxy, optionally substituted amine (e.g., $NH_2$), optionally substituted C1-C4 alkoxy, 1-benzyl-4-piperidinoxy, optionally substituted 5- or 6-membered carbocyclic group, optionally substituted 5- or 6-membered heterocyclic group, optionally substituted aryl, optionally substituted heteroaryl, or $NR_6R_7$, or wherein $R_2$ and $R_3$, or $R_3$ and $R_4$, together with the atoms to which they are bound form an optionally substituted 5- or 6-membered carbocyclic group (e.g., an optionally substituted phenyl group) or an optionally substituted 5- or 6-membered heterocyclic group (e.g., an optionally substituted 5- or 6-membered heteroaryl group);

$R_4$ and $R_5$ each independently represents H, halo, hydroxy, optionally substituted amine (e.g., $NH_2$), optionally substituted C1-C4 alkoxy, 1-benzyl-4-piperidinoxy, optionally substituted 5- or 6-membered carbocyclic group, optionally substituted 5- or 6-membered heterocyclic group, optionally substituted aryl, optionally substituted heteroaryl, or NR$_6$R$_7$, or wherein R$_4$ and R$_5$, together with the atoms to which they are bound form an optionally substituted 5- or 6-membered carbocyclic group (e.g., an optionally substituted phenyl group) or an optionally substituted 5- or 6-membered heterocyclic group (e.g., an optionally substituted 5- or 6-membered heteroaryl group);

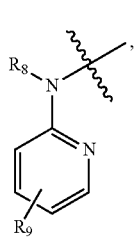

(A$_2$)

wherein R$_8$ represents H, optionally substituted C1-C4 alkyl, optionally substituted amine (e.g., NH$_2$), optionally substituted C1-C4 alkoxy, optionally substituted aryl, or an optionally substituted heteroaryl group, and R$_9$ represents H, halo (e.g., Cl or F), hydroxy, optionally substituted C1-C4 alkyl, optionally substituted amine (e.g., NH$_2$), optionally substituted C1-C4 alkoxy, optionally substituted 5- or 6-membered carbocyclic group (e.g., an optionally substituted phenyl group), or an optionally substituted 5- or 6-membered heterocyclic group (e.g., an optionally substituted 5- or 6-membered heteroaryl group);

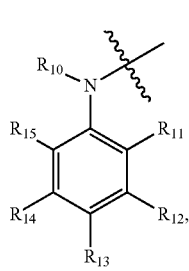

(A$_3$)

wherein R$_{10}$ represents H, optionally substituted C1-C4 alkyl, optionally substituted amine, (e.g., NH$_2$) optionally substituted C1-C4 alkoxy, optionally substituted aryl, or an optionally substituted heteroaryl group, and R$_{11}$, R$_{12}$, R$_{13}$, R$_{14}$, and R$_{15}$ each independently represents H, halo, hydroxy, optionally substituted C1-C4 alkoxy, optionally substituted aryl (which as defined herein embraces aralkyl and aralkoxy), optionally substituted heteroaryl (which as defined herein embraces heteroaralkyl and heteroaralkoxy), or NR$_6$R$_7$, wherein each of R$_6$ and R$_7$ independently represents H or a substituent (e.g., optionally substituted amine (e.g., NH$_2$), optionally substituted C1-C4 alkyl, optionally substituted C1-C4 alkoxy, optionally substituted aryl, optionally substituted heteroaryl), or R$_{11}$ together with R$_{12}$ and the other atoms to which they are bound form an optionally substituted 5- or 6-membered carbocyclic group (e.g., an optionally substituted phenyl group) or an optionally substituted 5- or 6-membered heterocyclic group (e.g., an optionally substituted 5- or 6-membered heteroaryl group), or R$_{12}$ together with R$_{13}$ and the other atoms to which they are bound form an optionally substituted 5- or 6-membered carbocyclic group (e.g., an optionally substituted phenyl group) or an optionally substituted 5- or 6-membered heterocyclic group (e.g., an optionally substituted 5- or 6-membered heteroaryl group), or R$_{13}$ together with R$_{14}$ and the other atoms to which they are bound form an optionally substituted 5- or 6-membered carbocyclic group (e.g., an optionally substituted phenyl group) or an optionally substituted 5- or 6-membered heterocyclic group (e.g., an optionally substituted 5- or 6-membered heteroaryl group), or R$_{14}$ together with R$_{15}$ and the other atoms to which they are bound form an optionally substituted 5- or 6-membered carbocyclic group (e.g., an optionally substituted phenyl group) or an optionally substituted 5- or 6-membered heterocyclic group (e.g., an optionally substituted 5- or 6-membered heteroaryl group);

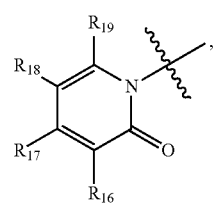

(A$_4$)

wherein R$_{16}$, R$_{17}$, R$_{18}$ and R$_{19}$ independently represent H or a substituent (e.g., optionally substituted amine (e.g., NH$_2$), hydroxy, optionally substituted C1-C4 alkyl, optionally substituted C1-C4 alkoxy, optionally substituted aryl, optionally substituted heteroaryl), or wherein R$_{16}$ and R$_{17}$ together with the atoms to which they are bound form an optionally substituted 5- or 6-membered carbocyclic group (e.g., optionally substituted phenyl group), an optionally substituted 5- or 6-membered heterocyclic group (e.g., an optionally substituted 5- or 6-membered heteroaryl group), or wherein R$_{17}$ and R$_{18}$ together with the atoms to which they are bound form an optionally substituted 5- or 6-membered carbocyclic group (e.g., a phenyl group), an optionally substituted 5- or 6-membered heterocyclic group (e.g., a 5- or 6-membered heteroaryl group), or wherein R$_{18}$ and R$_{19}$ together with the atoms to which they are bound form an optionally substituted 5- or 6-membered carbocyclic group (e.g., a phenyl group), or an optionally substituted 5- or 6-membered heterocyclic group (e.g., a 5- or 6-membered heteroaryl group); or

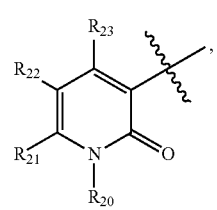

(A$_5$)

wherein $R_{20}$, $R_{21}$, $R_{22}$ and $R_{23}$ independently represent H or a substituent (e.g., optionally substituted amine (e.g., $NH_2$), hydroxy, optionally substituted C1-C4 alkyl, optionally substituted C1-C4 alkoxy, optionally substituted aryl, optionally substituted heteroaryl), or wherein $R_{20}$ and $R_{21}$ together with the atoms to which they are bound form an optionally substituted 5- or 6-membered heterocyclic group, or wherein $R_{21}$ and $R_{22}$ together with the atoms to which they are bound form an optionally substituted 5- or 6-membered carbocyclic group (e.g., a phenyl group), an optionally substituted 5- or 6-membered heterocyclic group (e.g., a 5- or 6-membered heteroaryl group), or wherein $R_{22}$ and $R_{23}$ together with the atoms to which they are bound form an optionally substituted 5- or 6-membered carbocyclic group (e.g., a phenyl group), or an optionally substituted 5- or 6-membered heterocyclic group (e.g., a 5- or 6-membered heteroaryl group); or a pharmaceutically acceptable salt or stereoisomer thereof.

In some embodiments wherein A is $A_1$, not all of $R_2$, $R_3$, $R_4$, and $R_5$ represents H. In some embodiments, such as when X represents N, all of $R_1$, $R_2$, $R_4$ and $R_5$ represents H. In some embodiments, such as when $X_1$ represents N, all of $R_2$, $R_3$, $R_4$ and $R_5$ represents H. In some embodiments, one of $R_2$, $R_3$, $R_4$, and $R_5$ represents a substituted benzyloxy group (e.g., 4-[[4(oxymethyl)phenyl]methyl]morpholine), or halo (e.g., Cl). In some embodiments, $R_1$ and $R_2$ together with the atoms to which they are bound form an optionally substituted 6-membered heteroaryl group such as a pyridyl group.

In some embodiments wherein A is $A_2$, $R_8$ is H or methyl, and $R_9$ is H, hydroxy, $NH_2$ or halo (e.g., Cl).

In some embodiments wherein A is $A_3$, $R_{10}$ is H or methyl, and $R_{11}$ and $R_{12}$ together with the atoms to which they are bound form an optionally substituted 5-membered heterocyclic group.

In some embodiments wherein A is $A_4$, $R_{16}$ and $R_{17}$ together with the atoms to which they are bound form an optionally substituted 6-membered aryl ring. In some embodiments, $R_{17}$ and $R_{18}$ together with the atoms to which they are bound form an optionally substituted 6-membered aryl ring. In some embodiments, $R_{18}$ and $R_{19}$ together with the atoms to which they are bound form an optionally substituted 6-membered aryl ring. In some embodiments, the aryl group formed by $R_{16}$ and $R_{17}$, or by $R_{17}$ and $R_{18}$, or by $R_{18}$ and $R_{19}$ is a phenyl group. In some embodiments, the 6-membered aryl group is unsubstituted.

In some embodiments, wherein A is $A_5$, $R_{20}$ is H, methyl, phenyl or benzyl, and $R_{21}$, $R_{22}$, and $R_{23}$ are H.

In some embodiments, wherein A is $A_1$, X is C and $X_1$ is N, and the compound of formula (I) is represented by formula (Ia):

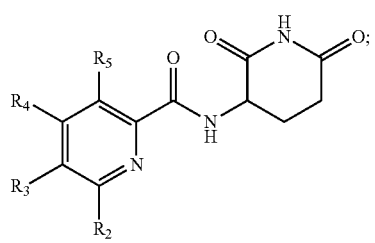

(Ia)

or a pharmaceutically acceptable salt or stereoisomer thereof.

In some embodiments, wherein A is $A_1$, X is C and $X_1$ is N, one of $R_2$, $R_3$, $R_4$, and $R_5$ represents C5-C6 heterocyclic substituted benzyl or 1-benzyl-4-piperidinoxy.

In some embodiments, wherein A is $A_1$, and X and $X_1$ are both C, and the compound of formula (I) is represented by formula (Ib):

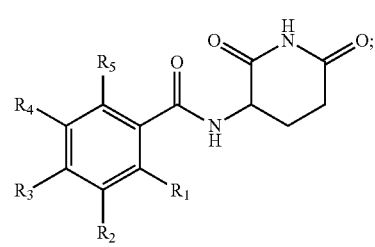

(Ib)

or a pharmaceutically acceptable salt or stereoisomer thereof.

In some embodiments, wherein A is $A_1$, and X and $X_1$ are both N, and the compound of formula I is represented by formula (Ic):

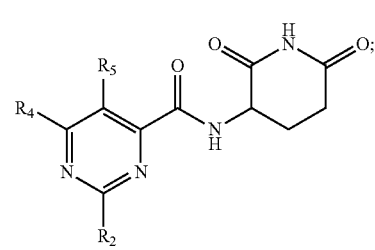

(Ic)

or a pharmaceutically acceptable salt or stereoisomer thereof.

In some embodiments, compounds of formula (I) of the present invention are represented by the following structures:

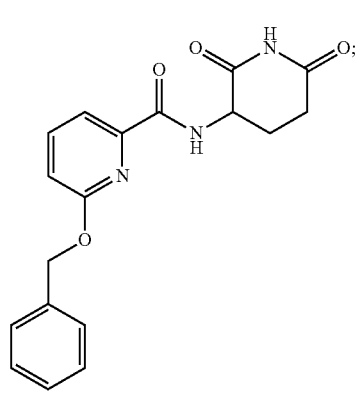

(1)

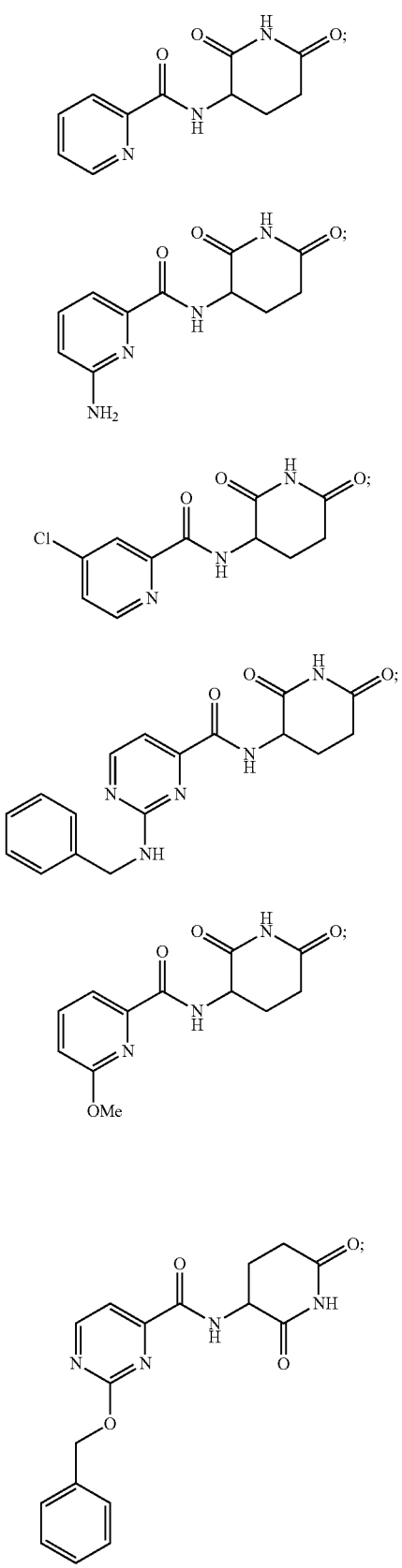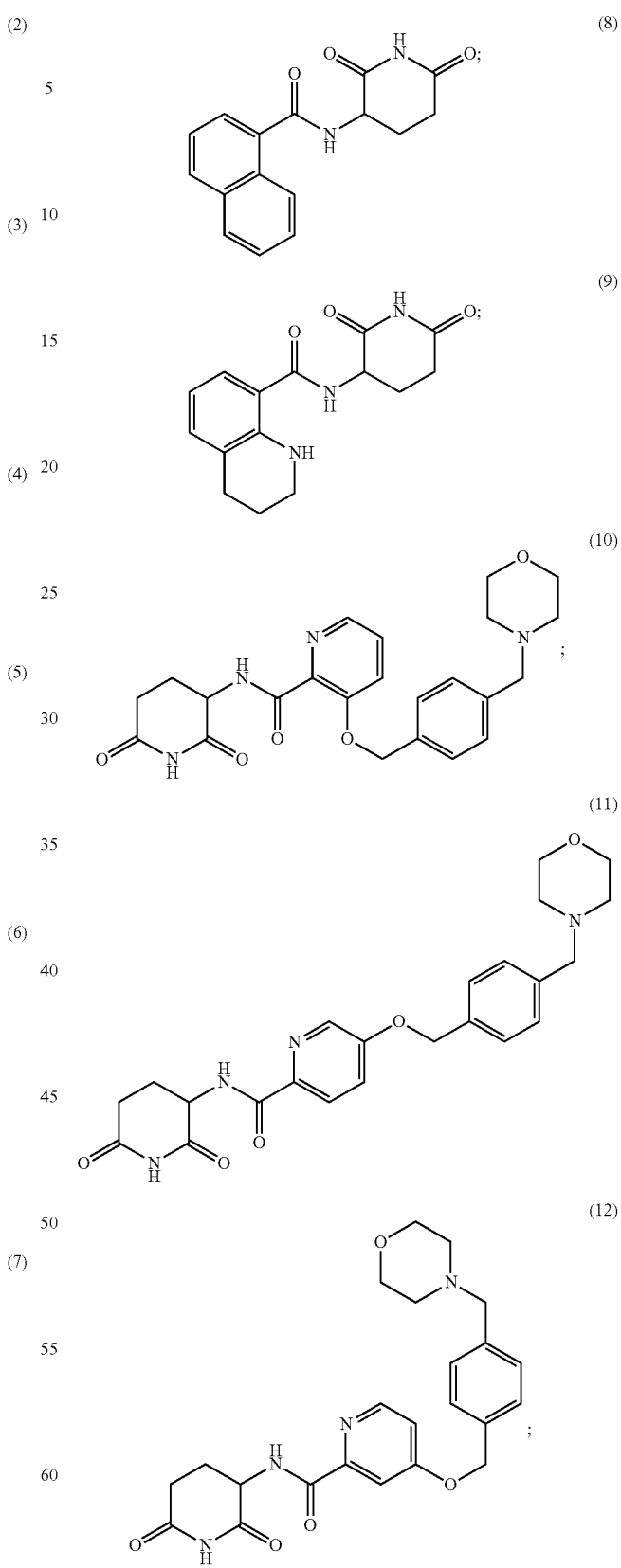

-continued
(13) 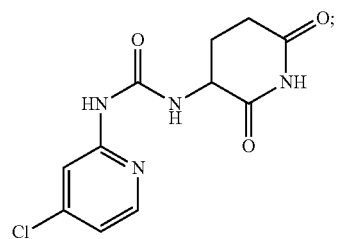
(14) 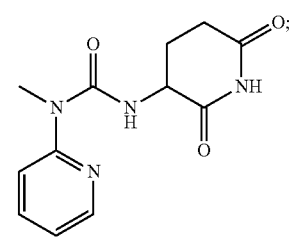
(15) 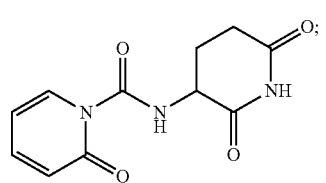
(16) 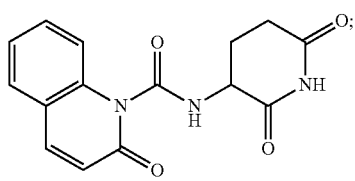
(17) 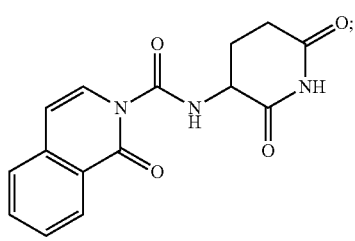
(18) 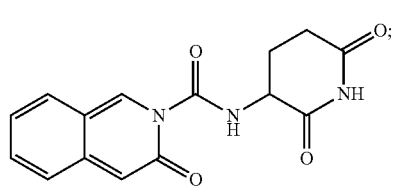
(19) 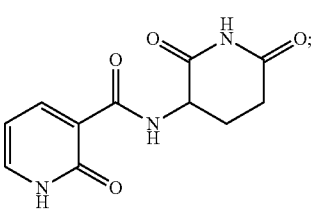
-continued
(20) 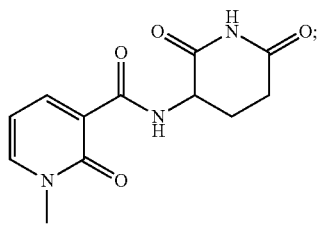
(21) 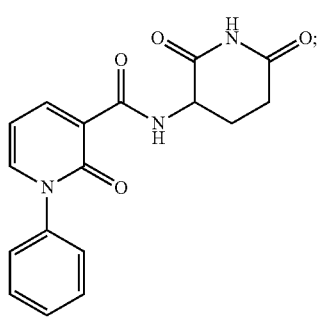
(22) 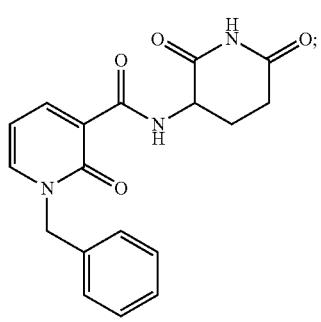
(23) 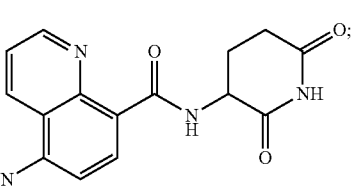
(24) 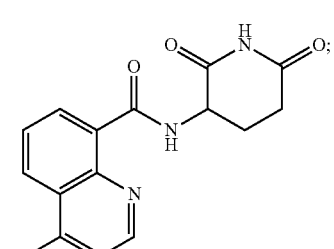
(25) 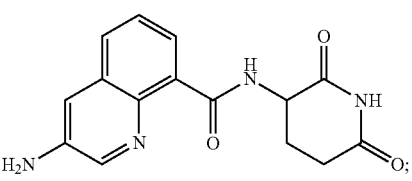

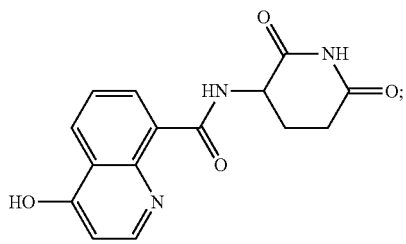(26)
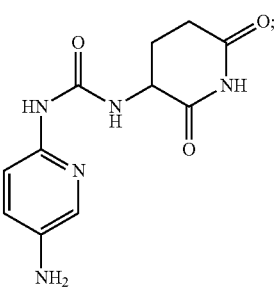(27)
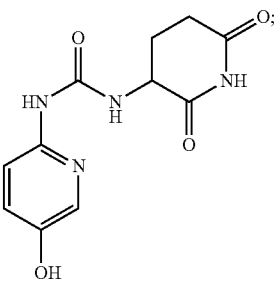(28)
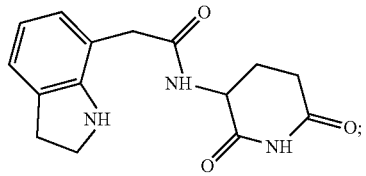(29)
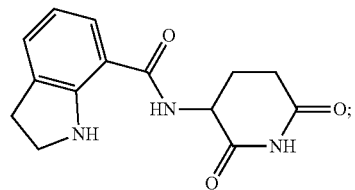(30)
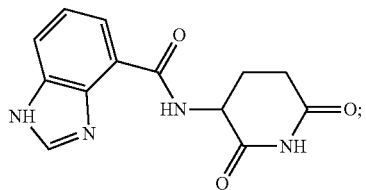(31)
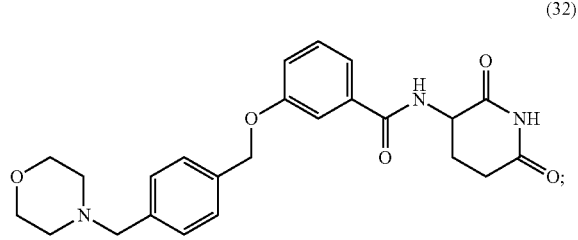(32)
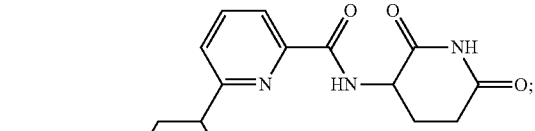(33)
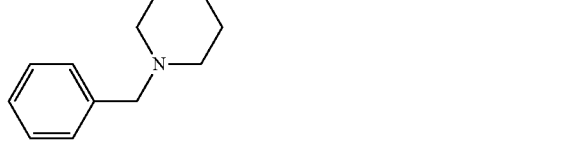(34)
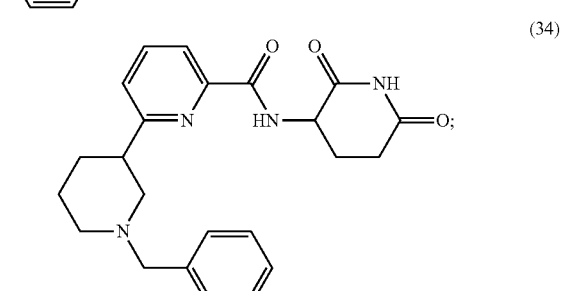(35)
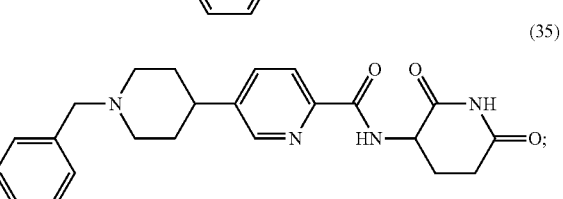(36)
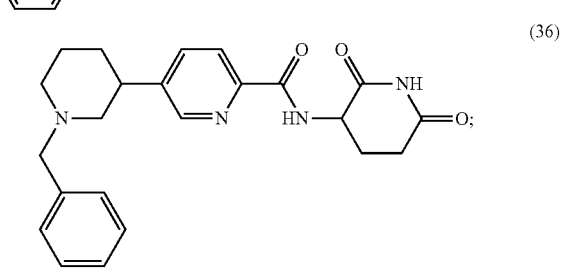(37)
; and
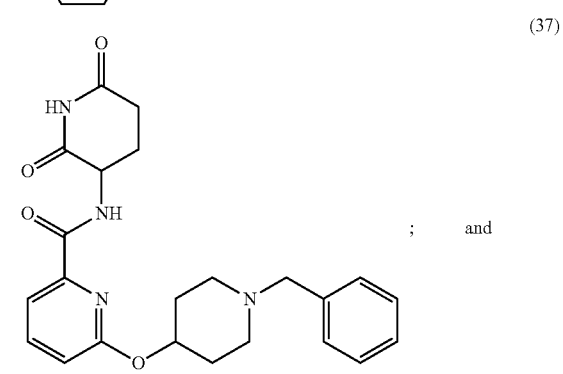(38)

or pharmaceutically acceptable salts or stereoisomers thereof.

Compounds of the present invention may be in the form of a free acid or free base, or a pharmaceutically acceptable salt. As used herein, the term "pharmaceutically acceptable" refers to a material which does not abrogate the biological activity or properties of the compound, and is relatively non-toxic, i.e., the material may be administered to a subject without causing undesirable biological effects (such as dizziness or gastric upset) or interacting in a deleterious manner with any of the components of the composition in which it is contained. The term "pharmaceutically acceptable salt" refers to a product obtained by reaction of the compound of the present invention with a suitable acid or a base. Examples of pharmaceutically acceptable salts of the compounds of this invention include those derived from suitable inorganic bases such as Li, Na, K, Ca, Mg, Fe, Cu, Al, Zn and Mn salts. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the invention can form pharmaceutically acceptable salts with various organic bases such as lysine, arginine, guanidine, diethanolamine or metformin.

In some embodiments, the compound of formula (I) is an isotopic derivative in that it has at least one desired isotopic substitution of an atom, at an amount above the natural abundance of the isotope, i.e., enriched. In one embodiment, the compound includes deuterium or multiple deuterium atoms. Substitution with heavier isotopes such as deuterium, i.e. $^2H$, may afford certain therapeutic advantages resulting from greater metabolic stability, for example, increased in vivo half-life or reduced dosage requirements, and thus may be advantageous in some circumstances.

Compounds of the present invention may have at least one chiral center and thus may be in the form of a stereoisomer, which as used herein, embraces all isomers of individual compounds that differ only in the orientation of their atoms in space. The term stereoisomer includes mirror image isomers (enantiomers which include the (R-) or (S-) configurations of the compounds), mixtures of mirror image isomers (physical mixtures of the enantiomers, and racemates or racemic mixtures) of compounds, geometric (cis/trans or E/Z, R/S) isomers of compounds and isomers of compounds with more than one chiral center that are not mirror images of one another (diastereoisomers). The chiral centers of the compounds may undergo epimerization in vivo; thus, for these compounds, administration of the compound in its (R-) form is considered equivalent to administration of the compound in its (S-) form. Accordingly, the compounds of the present invention may be made and used in the form of individual isomers and substantially free of other isomers, or in the form of a mixture of various isomers, e.g., racemic mixtures of stereoisomers.

In addition, the compounds of the present invention embrace the use of N-oxides, crystalline forms (also known as polymorphs), active metabolites of the compounds having the same type of activity, tautomers, and unsolvated as well as solvated forms with pharmaceutically acceptable solvents such as water, ethanol, and the like, of the compounds. The solvated forms of the conjugates presented herein are also considered to be disclosed herein.

Methods of Synthesis

In another aspect, the present invention is directed to a method for making a compound of formula (I), or a pharmaceutically acceptable salt or stereoisomer thereof. Broadly, the inventive compounds or pharmaceutically-acceptable salts or stereoisomers thereof, may be prepared by any process known to be applicable to the preparation of chemically related compounds. The compounds of the present invention will be better understood in connection with the synthetic schemes that are described in various working examples and which illustrate nonlimiting methods by which the compounds of the invention may be prepared.

Pharmaceutical Compositions

Another aspect of the present invention is directed to a pharmaceutical composition that includes a therapeutically effective amount of the compound of formula (I) or a pharmaceutically acceptable salt or stereoisomer thereof, and a pharmaceutically acceptable carrier. The term "pharmaceutically acceptable carrier," as known in the art, refers to a pharmaceutically acceptable material, composition or vehicle, suitable for administering compounds of the present invention to mammals. Suitable carriers may include, for example, liquids (both aqueous and non-aqueous alike, and combinations thereof), solids, encapsulating materials, gases, and combinations thereof (e.g., semi-solids), and gases, that function to carry or transport the compound from one organ, or portion of the body, to another organ, or portion of the body. A carrier is "acceptable" in the sense of being physiologically inert to and compatible with the other ingredients of the formulation and not injurious to the subject or patient. Depending on the type of formulation, the composition may include one or more pharmaceutically acceptable excipients.

Broadly, compounds of formula (I) may be formulated into a given type of composition in accordance with conventional pharmaceutical practice such as conventional mixing, dissolving, granulating, dragee-making, levigating, emulsifying, encapsulating, entrapping and compression processes (see, e.g., Remington: *The Science and Practice of Pharmacy* (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York). The type of formulation depends on the mode of administration which may include enteral (e.g., oral, buccal, sublingual and rectal), parenteral (e.g., subcutaneous (s.c.), intravenous (i.v.), intramuscular (i.m.), and intrasternal injection, or infusion techniques, intra-ocular, intra-arterial, intramedullary, intrathecal, intraventricular, transdermal, interdermal, intravaginal, intraperitoneal, mucosal, nasal, intratracheal instillation, bronchial instillation, and inhalation) and topical (e.g., transdermal). In general, the most appropriate route of administration will depend upon a variety of factors including, for example, the nature of the agent (e.g., its stability in the environment of the gastrointestinal tract), and/or the condition of the subject (e.g., whether the subject is able to tolerate oral administration). For example, parenteral (e.g., intravenous) administration may also be advantageous in that the compound may be administered relatively quickly such as in the case of a single-dose treatment and/or an acute condition.

In some embodiments, the compositions are formulated for oral or intravenous administration (e.g., systemic intravenous injection).

Accordingly, compounds of the present invention may be formulated into solid compositions (e.g., powders, tablets, dispersible granules, capsules, cachets, and suppositories), liquid compositions (e.g., solutions in which the compound is dissolved, suspensions in which solid particles of the compound are dispersed, emulsions, and solutions containing liposomes, micelles, or nanoparticles, syrups and elixirs); semi-solid compositions (e.g., gels, suspensions and creams); and gases (e.g., propellants for aerosol compositions). Compounds may also be formulated for rapid, intermediate or extended release.

Solid dosage forms for oral administration include capsules, tablets, pills, powders, and granules. In such solid dosage forms, the active compound is mixed with a carrier such as sodium citrate or dicalcium phosphate and an additional carrier or excipient such as a) fillers or extenders such as starches, lactose, sucrose, glucose, mannitol, and silicic acid, b) binders such as, for example, methylcellulose, microcrystalline cellulose, hydroxypropylmethylcellulose, carboxymethylcellulose, sodium carboxymethylcellulose, alginates, gelatin, polyvinylpyrrolidinone, sucrose, and acacia, c) humectants such as glycerol, d) disintegrating agents such as crosslinked polymers (e.g., crosslinked polyvinylpyrrolidone (crospovidone), crosslinked sodium carboxymethyl cellulose (croscarmellose sodium), sodium starch glycolate, agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also include buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings. They may further contain an opacifying agent.

In some embodiments, compounds of the present invention may be formulated in a hard or soft gelatin capsule. Representative excipients that may be used include pregelatinized starch, magnesium stearate, mannitol, sodium stearyl fumarate, lactose anhydrous, microcrystalline cellulose and croscarmellose sodium. Gelatin shells may include gelatin, titanium dioxide, iron oxides and colorants.

Liquid dosage forms for oral administration include solutions, suspensions, emulsions, micro-emulsions, syrups and elixirs. In addition to the compound, the liquid dosage forms may contain an aqueous or non-aqueous carrier (depending upon the solubility of the compounds) commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Oral compositions may also include an excipients such as wetting agents, suspending agents, coloring, sweetening, flavoring, and perfuming agents.

Injectable preparations may include sterile aqueous solutions or oleaginous suspensions. They may be formulated according to standard techniques using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The effect of the compound may be prolonged by slowing its absorption, which may be accomplished by the use of a liquid suspension or crystalline or amorphous material with poor water solubility. Prolonged absorption of the compound from a parenterally administered formulation may also be accomplished by suspending the compound in an oily vehicle.

In certain embodiments, compounds of formula (I) may be administered in a local rather than systemic manner, for example, via injection of the conjugate directly into an organ, often in a depot preparation or sustained release formulation. In specific embodiments, long acting formulations are administered by implantation (for example subcutaneously or intramuscularly) or by intramuscular injection. Injectable depot forms are made by forming microencapsule matrices of the compound in a biodegradable polymer, e.g., polylactide-polyglycolides, poly(orthoesters) and poly(anhydrides). The rate of release of the compound may be controlled by varying the ratio of compound to polymer and the nature of the particular polymer employed. Depot injectable formulations are also prepared by entrapping the compound in liposomes or microemulsions that are compatible with body tissues. Furthermore, in other embodiments, the compound is delivered in a targeted drug delivery system, for example, in a liposome coated with organ-specific antibody. In such embodiments, the liposomes are targeted to and taken up selectively by the organ.

The inventive compounds may be formulated for buccal or sublingual administration, examples of which include tablets, lozenges and gels.

The compounds may be formulated for administration by inhalation. Various forms suitable for administration by inhalation include aerosols, mists or powders. Pharmaceutical compositions may be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In some embodiments, the dosage unit of a pressurized aerosol may be determined by providing a valve to deliver a metered amount. In some embodiments, capsules and cartridges including gelatin, for example, for use in an inhaler or insufflator, may be formulated containing a powder mix of the compound and a suitable powder base such as lactose or starch.

Bispecific compounds of formula (I) may be formulated for topical administration which as used herein, refers to administration intradermally by application of the formulation to the epidermis. These types of compositions are typically in the form of ointments, pastes, creams, lotions, gels, solutions and sprays.

Representative examples of carriers useful in formulating compositions for topical application include solvents (e.g., alcohols, poly alcohols, water), creams, lotions, ointments, oils, plasters, liposomes, powders, emulsions, microemulsions, and buffered solutions (e.g., hypotonic or buffered saline). Creams, for example, may be formulated using saturated or unsaturated fatty acids such as stearic acid, palmitic acid, oleic acid, palmito-oleic acid, cetyl, or oleyl alcohols. Creams may also contain a non-ionic surfactant such as polyoxy-40-stearate.

In some embodiments, the topical formulations may also include an excipient, an example of which is a penetration enhancing agent. These agents are capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, Ill. (1997). Representative examples of penetration enhancing agents include triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Representative examples of yet other excipients that may be included in topical as well as in other types of formulations (to the extent they are compatible), include preservatives, antioxidants, moisturizers, emollients, buffering agents, solubilizing agents, skin protectants, and surfactants. Suitable preservatives include alcohols, quaternary amines, organic acids, parabens, and phenols. Suitable antioxidants include ascorbic acid and its esters, sodium bisulfite, butylated hydroxytoluene, butylated hydroxyanisole, tocopherols, and chelating agents like EDTA and citric acid. Suitable moisturizers include glycerine, sorbitol, polyethylene glycols, urea, and propylene glycol. Suitable buffering agents include citric, hydrochloric, and lactic acid buffers. Suitable solubilizing agents include quaternary ammonium chlorides, cyclodextrins, benzyl benzoate, lecithin, and polysorbates. Suitable skin protectants include vitamin E oil, allatoin, dimethicone, glycerin, petrolatum, and zinc oxide.

Transdermal formulations typically employ transdermal delivery devices and transdermal delivery patches wherein the compound is formulated in lipophilic emulsions or buffered, aqueous solutions, dissolved and/or dispersed in a polymer or an adhesive. Patches may be constructed for continuous, pulsatile, or on demand delivery of pharmaceutical agents. Transdermal delivery of the compounds may be accomplished by means of an iontophoretic patch. Transdermal patches may provide controlled delivery of the compounds wherein the rate of absorption is slowed by using rate-controlling membranes or by trapping the compound within a polymer matrix or gel. Absorption enhancers may be used to increase absorption, examples of which include absorbable pharmaceutically acceptable solvents that assist passage through the skin.

Ophthalmic formulations include eye drops.

Formulations for rectal administration include enemas, rectal gels, rectal foams, rectal aerosols, and retention enemas, which may contain conventional suppository bases such as cocoa butter or other glycerides, as well as synthetic polymers such as polyvinylpyrrolidone, PEG, and the like. Compositions for rectal or vaginal administration may also be formulated as suppositories which can be prepared by mixing the compound with suitable non-irritating carriers and excipients such as cocoa butter, mixtures of fatty acid glycerides, polyethylene glycol, suppository waxes, and combinations thereof, all of which are solid at ambient temperature but liquid at body temperature and therefore melt in the rectum or vaginal cavity and release the compound.

Dosage Amounts

As used herein, the term "therapeutically effective amount" refers to an amount of a compound of formula (I) or a pharmaceutically acceptable salt or a stereoisomer thereof that is effective in producing the desired therapeutic response. The term "therapeutically effective amount" thus includes the amount of the compound of formula (I) or a pharmaceutically acceptable salt or a stereoisomer thereof, that when administered, induces a positive modification in the disease or disorder to be treated, or is sufficient to prevent development or progression of the disease or disorder, or alleviate to some extent, one or more of the symptoms of the disease or disorder being treated in a subject, or which simply kills or inhibits the growth of diseased (e.g., cancer) cells.

The total daily dosage of the compounds and usage thereof may be decided in accordance with standard medical practice, e.g., by the attending physician using sound medical judgment. The specific therapeutically effective dose for any particular subject will depend upon a variety of factors including the disease or disorder being treated and the severity thereof (e.g., its present status); the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed; and like factors well known in the medical arts (see, for example, Goodman and Gilman's, "The Pharmacological Basis of Therapeutics", 10th Edition, A. Gilman, J. Hardman and L. Limbird, eds., McGraw-Hill Press, 155-173, 2001).

Compounds of the present invention may be effective over a wide dosage range. In some embodiments, the total daily dosage (e.g., for adult humans) may range from about 0.001 to about 1600 mg, from 0.01 to about 1600 mg, from 0.01 to about 500 mg, from about 0.01 to about 100 mg, from about 0.5 to about 100 mg, from 1 to about 100-400 mg per day, from about 1 to about 50 mg per day, and from about 5 to about 40 mg per day, and in yet other embodiments from about 10 to about 30 mg per day. Individual dosage may be formulated to contain the desired dosage amount depending upon the number of times the compound is administered per day. By way of example, capsules may be formulated with from about 1 to about 200 mg of compound (e.g., 1, 2, 2.5, 3, 4, 5, 10, 15, 20, 25, 50, 100, 150, and 200 mg). In some embodiments, individual dosages may be formulated to contain the desired dosage amount depending upon the number of times the compound is administered per day.

Methods of Use

In some aspects, the compounds of the present invention may be useful in the treatment of diseases and disorders characterized or mediated by an aberrant (e.g., dysfunctional or dysregulated) protein that can be targeted for degradation by cereblon, and which participates in the inception, manifestation of one or more symptoms or markers, severity or progression of the disease or disorder), and where the degradation of the targeted protein may confer a therapeutic benefit. The diseases or disorders may be said to be characterized or mediated by aberrant protein activity (e.g., expression of mutated form of the protein or elevated levels of wild-type protein relative to a non-pathological state). The disease may also be characterized by a particular dependence/sensitivity to the removal of the protein, in this case by proteasomal degradation, while itself not necessarily being mutated or over expressed. A "disease" is generally regarded as a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the animal's state of health.

The term "subject" (or "patient") as used herein includes all members of the animal kingdom prone to or suffering from the indicated disease or disorder. In some embodiments, the subject is a mammal, e.g., a human or a non-human mammal. The methods are also applicable to companion animals such as dogs and cats as well as livestock such as cows, horses, sheep, goats, pigs, and other domesticated and wild animals. A subject "in need of" treatment according to the present invention may be "suffering from or suspected of suffering from" a specific disease or disorder may have been positively diagnosed or otherwise presents with a sufficient number of risk factors or a sufficient number or combination of signs or symptoms such that a medical professional could diagnose or suspect that the subject was suffering from the disease or disorder. Thus, subjects suffering from, and suspected of suffering from, a specific disease or disorder are not necessarily two distinct groups.

In some embodiments, compounds of formula (I) may be useful in the treatment of cell proliferative diseases and disorders characterized or mediated by a protein selected from the group consisting of casein kinase 1 alpha (CK1α)-, family with sequence similarity 83 member F (FAM83F)-, DTW domain containing 1 (DTWD1)-, zinc finger protein 91 homolog (ZFP91)-, ZFP62-, ZFP36 ring finger protein like (ZFP36L2)-, ring finger protein 166 (RNF166)-, Ikaros family zinc finger protein 1 (IKZF1)-, IKZF2-, IKZF3-, IKZF4-, IKZF5-, Ras-related protein Rab-28 (RAB28)-, glutathione S-transferase pi 1 (GSTP1)-, GSPT2-, mitochondrial import inner membrane translocase subunit Tim10 (TIMM10)-, GDNF inducible zinc finger protein 1 (GZF1)-, early growth response 1 (EGR1)-, hypermethylated in cancer 1 (HIC1)-, HIC2-, insulinoma-associated protein 2 (INSM2)-, odd-skipped related transcription factor 2 (OSR2)-, protein polybromo-1 (PB1)-, PR domain zinc finger protein 15 (PRD15)-, spalt like transcription factor 1 (SALL1)-, SALL3-, SALL4-, WIZ-, zinc finger and BTB domain-containing protein 17 (ZBT17)-, ZBT41-, ZBT49-, ZBT7A-, ZBT7B-, ZBTB2-, ZBTB39-, zinc finger protein interacting with K protein 1 (ZIK1)-, zinc finger protein 3 (ZNF3)-, ZNF217-, ZNF276-, ZNF316-, ZNF324B-, ZNF335-, ZNF397-, ZNF407-, ZNF408-, ZNF462-, ZNF483-, SNF517-, ZNF526-, ZNF581-, ZNF587-, ZNF589-, ZNF618-, ZNF644-, ZNF646-, ZNF653-, ZNF654-, ZNF692, ZNF724-, ZNF771-, ZNF782-, ZNF784-, ZNF814-, zinc finger and SCAN domain containing 10 (ZSC10)-, ZSC22-, ZC827-, or zinc finger with UFM1-specific peptidase domain (ZUFSP). As disclosed above, these proteins are believed to bind a complex formed between cereblon and the compound of formula (I).

In some embodiments, compounds of formula (I) may be useful in the treatment of cell proliferative diseases and disorders (e.g., cancer or benign neoplasms). As used herein, the term "cell proliferative disease or disorder" refers to the conditions characterized by unregulated or abnormal cell growth, or both, including noncancerous conditions, precancerous conditions and cancer.

Exemplary types of non-cancerous (e.g., cell proliferative) diseases or disorders that may be amenable to treatment with the compounds of the present invention include inflammatory diseases and conditions, autoimmune diseases, neurodegenerative diseases, heart diseases, viral diseases, chronic and acute kidney diseases or injuries, metabolic diseases, and allergic and genetic diseases.

Representative examples of specific non-cancerous diseases and disorders include rheumatoid arthritis, alopecia areata, lymphoproliferative conditions, autoimmune hematological disorders (e.g. hemolytic anemia, aplastic anemia, anhidrotic ectodermal dysplasia, pure red cell anemia and idiopathic thrombocytopenia), cholecystitis, acromegaly, rheumatoid spondylitis, osteoarthritis, gout, scleroderma, sepsis, septic shock, dacryoadenitis, cryopyrin associated periodic syndrome (CAPS), endotoxic shock, endometritis, gram-negative sepsis, keratoconjunctivitis sicca, toxic shock syndrome, asthma, adult respiratory distress syndrome, chronic obstructive pulmonary disease, chronic pulmonary inflammation, chronic graft rejection, hidradenitis suppurativa, inflammatory bowel disease, Crohn's disease, Behcet's syndrome, systemic lupus erythematosus, glomerulonephritis, multiple sclerosis, juvenile-onset diabetes, autoimmune uveoretinitis, autoimmune vasculitis, thyroiditis, Addison's disease, lichen planus, appendicitis, bullous pemphigus, pemphigus vulgaris, pemphigus foliaceus, paraneoplastic pemphigus, myasthenia gravis, immunoglobulin A nephropathy, autoimmune thyroiditis or Hashimoto's disease, Sjogren's syndrome, vitiligo, Wegener granulomatosis, granulomatous orchitis, autoimmune oophoritis, sarcoidosis, rheumatic carditis, ankylosing spondylitis, Grave's disease, autoimmune thrombocytopenic purpura, psoriasis, psoriatic arthritis, eczema, dermatitis herpetiformis, ulcerative colitis, pancreatic fibrosis, hepatitis, hepatic fibrosis, CD14 mediated sepsis, non-CD14 mediated sepsis, acute and chronic renal disease, irritable bowel syndrome, pyresis, restenosis, cerebral malaria, cervicitis, stroke and ischemic injury, neural trauma, acute and chronic pain, allergic rhinitis, allergic conjunctivitis, chronic heart failure, congestive heart failure, acute coronary syndrome, cachexia, malaria, leprosy, leishmaniasis, Lyme disease, Reiter's syndrome, acute synovitis, muscle degeneration, bursitis, tendonitis, tenosynovitis, herniated, ruptured, or prolapsed intervertebral disk syndrome, osteopetrosis, rhinosinusitis, thrombosis, silicosis, pulmonary sarcosis, bone resorption diseases, such as osteoporosis, graft-versus-host reaction, fibromyalgia, AIDS and other viral diseases such as Herpes Zoster, Herpes Simplex I or II, influenza virus and cytomegalovirus, diabetes Type I and II, obesity, insulin resistance and diabetic retinopathy, 22q11.2 deletion syndrome, Angelman syndrome, Canavan disease, celiac disease, Charcot-Marie-Tooth disease, color blindness, Cri du chat, Down syndrome, cystic fibrosis, Duchenne muscular dystrophy, haemophilia, Klinefleter's syndrome, neurofibromatosis, phenylketonuria, Prader-Willi syndrome, sudden infant death syndrome, sickle cell disease, Tay-Sachs disease, Turner syndrome, urea cycle disorders, thalassemia, otitis, pancreatitis, parotitis, pericarditis, peritonitis, pharyngitis, pleuritis, phlebitis, pneumonitis, cystic fibrosis, uveitis, polymyositis, proctitis, interstitial lung fibrosis, dermatomyositis, arteriosclerosis, amyotrophic lateral sclerosis, asocality, immune response, varicosis, vaginitis, including chronic recurrent yeast vaginitis, depression, and Sudden Infant Death Syndrome.

In other embodiments, the methods are directed to treating subjects having cancer. Broadly, the compounds of the present invention may be effective in the treatment of carcinomas (solid tumors including both primary and metastatic tumors), sarcomas, melanomas, and hematological cancers (cancers affecting blood including lymphocytes, bone marrow and/or lymph nodes) including leukemia, lymphoma and multiple myeloma. Adult tumors/cancers and pediatric tumors/cancers are included. The cancers may be vascularized, or not yet substantially vascularized, or non-vascularized tumors.

Representative examples of cancers includes adenocortical carcinoma, AIDS-related cancers (e.g., Kaposi's and AIDS-related lymphoma), appendix cancer, childhood cancers (e.g., childhood cerebellar astrocytoma, childhood cerebral astrocytoma), basal cell carcinoma, skin cancer (non-melanoma), biliary cancer, extrahepatic bile duct cancer, intrahepatic bile duct cancer, bladder cancer, urinary bladder cancer, brain cancer (e.g., gliomas and glioblastomas such as brain stem glioma, cerebellar astrocytoma, cerebral astrocytoma/malignant glioma, ependymoma, medulloblastoma, supratentorial primitive neuroectodeimal tumors, visual pathway and hypothalamic glioma), breast cancer, bronchial adenomas/carcinoids, carcinoid tumor, nervous system cancer (e.g., central nervous system cancer, central nervous system lymphoma), cervical cancer, chronic myeloproliferative disorders, colorectal cancer (e.g., colon cancer, rectal cancer), lymphoid neoplasm, mycosis fungoids, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastrointestinal cancer (e.g., stomach cancer, small intestine cancer, gastrointestinal carcinoid tumor, gastrointestinal stromal tumor (GIST)), cholangiocarcinoma, germ cell tumor, ovarian germ cell tumor, gestational trophoblastic tumor glioma, head and neck cancer, neuroendocrine tumors, Hodgkin's lymphoma, Ann Arbor stage III and stage IV childhood Non-Hodgkin's lymphoma, ROS1-positive refractory Non-Hodgkin's lymphoma, leukemia, lymphoma, multiple myeloma, hypopharyngeal cancer, intraocular melanoma, ocular cancer, islet cell tumors (endocrine pancreas), renal cancer (e.g., Wilm's Tumor, renal cell carcinoma), liver cancer, lung cancer (e.g., non-small cell lung cancer and small cell lung cancer), ALK-positive anaplastic large cell lymphoma, ALK-positive advanced malignant solid neoplasm, Waldenstrom's macroglobulinema, melanoma, intraocular (eye) melanoma, merkel cell carcinoma, mesothelioma, metastatic squamous neck cancer with occult primary, multiple endocrine neoplasia (MEN), myelodysplastic syndromes, myelodysplastic/myeloproliferative diseases, nasopharyngeal cancer, neuroblastoma, oral cancer (e.g., mouth cancer, lip cancer, oral cavity cancer, tongue cancer, oropharyngeal cancer, throat cancer, laryngeal cancer), ovarian cancer (e.g., ovarian epithelial cancer, ovarian germ cell tumor, ovarian low malignant potential tumor), pancreatic cancer, islet cell pancreatic cancer, paranasal sinus and nasal cavity cancer, parathyroid cancer, penile cancer, pharyngeal cancer, pheochromocytoma, pineoblastoma, metastatic anaplastic thyroid cancer, undifferentiated thyroid cancer, papillary thyroid cancer, pituitary tumor, plasma cell neoplasm/multiple myeloma, pleuropulmonary blastoma, prostate cancer, retinoblastoma rhabdomyosarcoma, salivary gland cancer, uterine cancer (e.g., endometrial uterine cancer, uterine sarcoma, uterine corpus cancer), squamous cell carcinoma, testicular cancer, thymoma, thymic carcinoma, thyroid cancer, juvenile xanthogranuloma, transitional cell cancer of the renal pelvis and ureter and other urinary organs, urethral cancer, gestational trophoblastic tumor, vaginal cancer, vulvar cancer, hepatoblastoma, rhabdoid tumor, and Wilms tumor.

Sarcomas that may be treatable with compounds of the present invention include both soft tissue and bone cancers alike, representative examples of which include osteosarcoma or osteogenic sarcoma (bone) (e.g., Ewing's sarcoma), chondrosarcoma (cartilage), leiomyosarcoma (smooth muscle), rhabdomyosarcoma (skeletal muscle), mesothelial sarcoma or mesothelioma (membranous lining of body cavities), fibrosarcoma (fibrous tissue), angiosarcoma or hemangioendothelioma (blood vessels), liposarcoma (adipose tissue), glioma or astrocytoma (neurogenic connective tissue found in the brain), myxosarcoma (primitive embryonic connective tissue), mesenchymous or mixed mesodermal tumor (mixed connective tissue types), and histiocytic sarcoma (immune cancer).

In some embodiments, methods of the present invention entail treatment of subjects having cell proliferative diseases or disorders of the hematological system, liver (hepatocellular), brain, lung, colorectal (e.g., colon), pancreas, prostate, skin, ovary, breast, skin (e.g., melanoma), and endometrium.

As used herein, "cell proliferative diseases or disorders of the hematologic system" include lymphoma, leukemia, myeloid neoplasms, mast cell neoplasms, myelodysplasia, benign monoclonal gammopathy, lymphomatoid papulosis, polycythemia vera, chronic myelocytic leukemia, agnogenic myeloid metaplasia, and essential thrombocythemia. Representative examples of hematologic cancers may thus include multiple myeloma, lymphoma (including T-cell lymphoma, Hodgkin's lymphoma, non-Hodgkin's lymphoma (diffuse large B-cell lymphoma (DLBCL), follicular lymphoma (FL), acute myeloid leukemia (AML), acute promyelocytic leukemia (APL), mantle cell lymphoma (MCL) and ALK+ anaplastic large cell lymphoma) (e.g., B-cell non-Hodgkin's lymphoma selected from diffuse large B-cell lymphoma (e.g., germinal center B-cell-like diffuse large B-cell lymphoma or activated B-cell-like diffuse large B-cell lymphoma), Burkitt's lymphoma/leukemia, mantle cell lymphoma, mediastinal (thymic) large B-cell lymphoma, follicular lymphoma, marginal zone lymphoma, lymphoplasmacytic lymphoma/Waldenstrom macroglobulinemia, refractory B-cell non-Hodgkin's lymphoma, and relapsed B-cell non-Hodgkin's lymphoma), childhood lymphomas, and lymphomas of lymphocytic and cutaneous origin, (e.g., small lymphocytic lymphoma), leukemia (including childhood leukemia, hairy-cell leukemia, acute lymphocytic leukemia, acute myelocytic leukemia, acute myeloid leukemia (e.g., acute monocytic leukemia), chronic lymphocytic leukemia, small lymphocytic leukemia, chronic myelocytic leukemia, chronic myelogenous leukemia, and mast cell leukemia), myeloid neoplasms and mast cell neoplasms.

As used herein, "cell proliferative diseases or disorders of the liver" include all forms of cell proliferative disorders affecting the liver. Cell proliferative disorders of the liver may include liver cancer (e.g., hepatocellular carcinoma, intrahepatic cholangiocarcinoma and hepatoblastoma), a precancer or precancerous condition of the liver, benign growths or lesions of the liver, and malignant growths or lesions of the liver, and metastatic lesions in tissue and organs in the body other than the liver. Cell proliferative disorders of the brain may include hyperplasia, metaplasia, and dysplasia of the liver.

As used herein, "cell proliferative diseases or disorders of the brain" include all forms of cell proliferative disorders affecting the brain. Cell proliferative disorders of the brain may include brain cancer (e.g., gliomas and glioblastomas), a precancer or precancerous condition of the brain, benign growths or lesions of the brain, and malignant growths or lesions of the brain, and metastatic lesions in tissue and organs in the body other than the brain. Cell proliferative disorders of the brain may include hyperplasia, metaplasia, and dysplasia of the brain.

As used herein, "cell proliferative diseases or disorders of the lung" include all forms of cell proliferative disorders affecting lung cells. Cell proliferative disorders of the lung include lung cancer, a precancer or precancerous condition of the lung, benign growths or lesions of the lung, and metastatic lesions in the tissue and organs in the body other than the lung. Lung cancer includes all forms of cancer of the lung, e.g., malignant lung neoplasms, carcinoma in situ, typical carcinoid tumors, and atypical carcinoid tumors. Lung cancer includes small cell lung cancer ("SLCL"), non-small cell lung cancer ("NSCLC"), squamous cell carcinoma, adenocarcinoma, small cell carcinoma, large cell carcinoma, squamous cell carcinoma, and mesothelioma. Lung cancer can include "scar carcinoma", bronchoalveolar carcinoma, giant cell carcinoma, spindle cell carcinoma, and large cell neuroendocrine carcinoma. Lung cancer also includes lung neoplasms having histologic and ultrastructural heterogeneity (e.g., mixed cell types).

As used herein, "cell proliferative diseases or disorders of the colon" include all forms of cell proliferative disorders affecting colon cells, including colon cancer, a precancer or precancerous conditions of the colon, adenomatous polyps of the colon and metachronous lesions of the colon. Colon cancer includes sporadic and hereditary colon cancer, malignant colon neoplasms, carcinoma in situ, typical carcinoid tumors, and atypical carcinoid tumors, adenocarcinoma, squamous cell carcinoma, and squamous cell carcinoma. Colon cancer can be associated with a hereditary syndrome such as hereditary nonpolyposis colorectal cancer, familiar adenomatous polyposis, MYH associated polyposis, Gardner's syndrome, Peutz-Jeghers syndrome, Turcot's syndrome and juvenile polyposis. Cell proliferative disorders of the colon may be characterized by hyperplasia, metaplasia, or dysplasia of the colon.

As used herein, "cell proliferative diseases or disorders of the pancreas" include all forms of cell proliferative disorders affecting pancreatic cells. Cell proliferative disorders of the pancreas may include pancreatic cancer, a precancer or precancerous condition of the pancreas, hyperplasia of the pancreas, and dysplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas, including ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma, and pancreatic neoplasms having histologic and ultrastructural heterogeneity (e.g., mixed cell types).

As used herein, "cell proliferative diseases or disorders of the prostate" include all forms of cell proliferative disorders affecting the prostate. Cell proliferative disorders of the prostate may include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate may include hyperplasia, metaplasia, and dysplasia of the prostate.

As used herein, "cell proliferative diseases or disorders of the ovary" include all forms of cell proliferative disorders affecting cells of the ovary. Cell proliferative disorders of the ovary may include a precancer or precancerous condition of the ovary, benign growths or lesions of the ovary, ovarian cancer, and metastatic lesions in tissue and organs in the body other than the ovary.

As used herein, "cell proliferative diseases or disorders of the breast" include all forms of cell proliferative disorders affecting breast cells. Cell proliferative disorders of the breast may include breast cancer, a precancer or precancerous condition of the breast, benign growths or lesions of the breast, and metastatic lesions in tissue and organs in the body other than the breast.

As used herein, "cell proliferative diseases or disorders of the skin" include all forms of cell proliferative disorders affecting skin cells. Cell proliferative disorders of the skin may include a precancer or precancerous condition of the skin, benign growths or lesions of the skin, melanoma, malignant melanoma or other malignant growths or lesions of the skin, and metastatic lesions in tissue and organs in the body other than the skin. Cell proliferative disorders of the skin may include hyperplasia, metaplasia, and dysplasia of the skin.

As used herein, "cell proliferative diseases or disorders of the endometrium" include all forms of cell proliferative disorders affecting the endometrium. Cell proliferative disorders of the endometrium may include endometrial cancer, a precancer or precancerous condition of the endometrium, benign growths or lesions of the endometrium, and malignant growths or lesions of the endometrium, and metastatic lesions in tissue and organs in the body other than the endometrium. Cell proliferative disorders of the endometrium may include hyperplasia, metaplasia, and dysplasia of the endometrium.

The compounds of the present invention may be administered to a patient, e.g., a cancer patient, as a monotherapy or by way of combination therapy, and as a front-line therapy or a follow-on therapy for patients who are unresponsive to front line therapy. Therapy may be "first-line", i.e., as an initial treatment in patients who have undergone no prior anti-cancer treatment regimens, either alone or in combination with other treatments; or "second-line", as a treatment in patients who have undergone a prior anti-cancer treatment regimen, either alone or in combination with other treatments; or as "third-line", "fourth-line", etc. treatments, either alone or in combination with other treatments. Therapy may also be given to patients who have had previous treatments which have been partially successful but are intolerant to the particular treatment.

Therapy may also be given as an adjuvant treatment, i.e., to prevent reoccurrence of cancer in patients with no currently detectable disease or after surgical removal of a tumor. Thus, in some embodiments, the compound may be administered to a patient who has received another therapy, such as chemotherapy, radioimmunotherapy, surgical therapy, immunotherapy, radiation therapy, targeted therapy or any combination thereof.

The methods of the present invention may entail administration of compounds of the invention or pharmaceutical compositions thereof to the patient in a single dose or in multiple doses (e.g., 1, 2, 3, 4, 5, 6, 7, 8, 10, 15, 20, or more doses). For example, the frequency of administration may range from once a day up to about once every eight weeks. In some embodiments, the frequency of administration ranges from about once a day for 1, 2, 3, 4, 5, or 6 weeks, and in other embodiments entails a 28-day cycle which includes daily administration for 3 weeks (21 days).

Combination Therapy

Compounds of formula (I) may be used in combination with at least one other active agent, e.g., anti-cancer agent or regimen, in treating diseases and disorders. The term "in combination" in this context means that the agents are co-administered, which includes substantially contemporaneous administration, by the same or separate dosage forms, or sequentially, e.g., as part of the same treatment regimen or by way of successive treatment regimens. Thus, if given sequentially, at the onset of administration of the second compound, the first of the two compounds is in some cases still detectable at effective concentrations at the site of treatment. The sequence and time interval may be determined such that they can act together (e.g., synergistically to provide an increased benefit than if they were administered otherwise). For example, the therapeutics may be administered at the same time or sequentially in any order at different points in time; however, if not administered at the same time, they may be administered sufficiently close in time so as to provide the desired therapeutic effect, which may be in a synergistic fashion. Thus, the terms are not limited to the administration of the active agents at exactly the same time.

In some embodiments, the treatment regimen may include administration of a compound of formula (I) in combination with one or more additional therapeutics known for use in treating the disease or condition (e.g., cancer). The dosage of the additional anticancer therapeutic may be the same or even lower than known or recommended doses. See, Hardman et al., eds., *Goodman & Gilman's The Pharmacological Basis Of Therapeutics*, 10th ed., McGraw-Hill, New York, 2001; Physician's Desk Reference 60th ed., 2006. Anticancer agents that may be used in combination with the inventive compounds are known in the art. See, e.g., U.S. Pat. No. 9,101,622 (Section 5.2 thereof) and U.S. Pat. No. 9,345,705 B2 (Columns 12-18 thereof). Representative examples of additional active agents and treatment regimens include radiation therapy, chemotherapeutics (e.g., mitotic inhibitors, angiogenesis inhibitors, antihormones, autophagy inhibitors, alkylating agents, intercalating antibiotics, growth factor inhibitors, anti-androgens, signal transduction pathway inhibitors, anti-microtubule agents, platinum coordination complexes, HDAC inhibitors, proteasome inhibitors, and topoisomerase inhibitors), immunomodulators, therapeutic antibodies (e.g., mono-specific and bispecific antibodies) and CAR-T therapy.

In some embodiments, the compound of the invention and the additional (e.g., anticancer) therapeutic may be administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. The two or more therapeutics may be administered within the same patient visit In some embodiments, the compound of the present invention and the additional agent or therapeutic (e.g., an anti-cancer therapeutic) are cyclically administered. Cycling therapy involves the administration of one anticancer therapeutic for a period of time, followed by the administration of a second anti-cancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies. In one example in the context of cancer treatment, cycling therapy involves the administration of a first anticancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

Pharmaceutical Kits

The present compositions may be assembled into kits or pharmaceutical systems. Kits or pharmaceutical systems according to this aspect of the invention include a carrier or package such as a box, carton, tube or the like, having in close confinement therein one or more containers, such as vials, tubes, ampoules, or bottles, which contain a compound of formula (I) or a pharmaceutical composition that contains a therapeutically effective amount of the compound of formula (I) and a pharmaceutically acceptable carrier. The kits or pharmaceutical systems of the invention may also include printed instructions for using the compound and composition.

These and other aspects of the present invention will be further appreciated upon consideration of the following Examples, which are intended to illustrate certain particular embodiments of the invention but are not intended to limit its scope, as defined by the claims.

EXAMPLES

Example 1: Synthesis of 6-(benzyloxy)-N-(2,6-dioxopiperidin-3-yl)picolinamide (1)

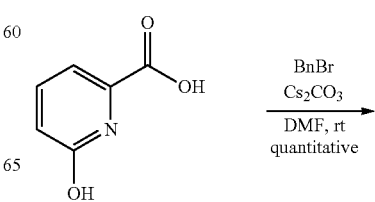

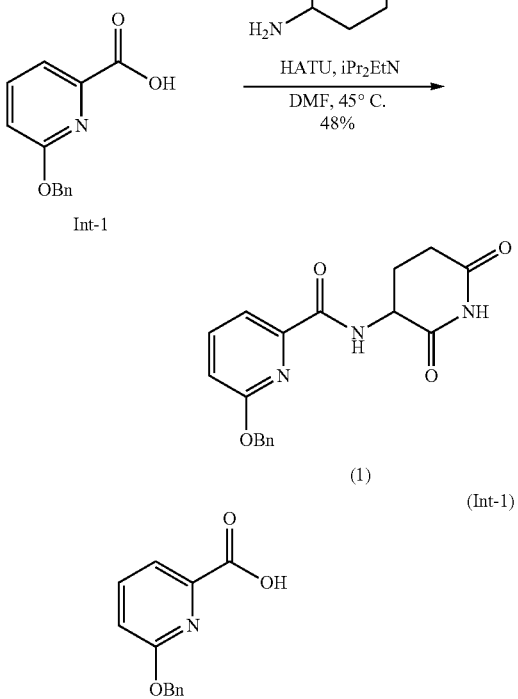

In a 40-mL vial, 6-hydroxypyridine-2-carboxylic acid (370 mg, 2.7 mmol) was dissolved in N,N-dimethylformamide (DMF) (0.3 M). Cesium carbonate (2.6 g, 8.0 mmol, 3.0 equiv) was added, followed by benzyl bromide (475 μL, 4.0 mmol, 1.5 equiv). The reaction mixture was stirred at room temperature (rt) overnight. The reaction was quenched with 1 M HCl, and extracted with EtOAc 3×. The organic layer was collected, washed with water 3×, brine, dried over Na$_2$SO$_4$, filtered, and concentrated by rotary evaporation to afford the crude benzyl-protected picolinic acid (Int-1) in quantitative yield, which was used without further purification.

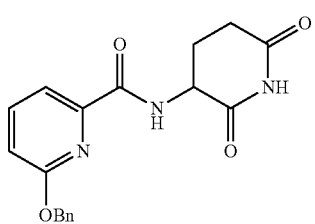

In an 8-mL vial, crude benzyl-protected picolinic acid (Int-1) (100 mg, 0.44 mmol) was dissolved in DMF (1.5 mL, 0.3 M). Diisopropylethylamine (230 μL, 1.3 mmol, 3.0 equiv) and 1-[bis(dimethylamino)methylene]-1H-1,2,3-triazolo[4,5-b]pyridinium 3-oxid hexafluorophosphate, (HATU) (182 mg, 0.48 mmol, 1.1 equiv), and amino glutarimide (3) (79 mg, 0.48 mmol, 1.1 equiv) were added sequentially. The reaction mixture was stirred at 45° C. for 2 days. Upon cooling to rt, the reaction mixture was diluted with CH$_2$Cl$_2$, washed with saturated aq. NH$_4$Cl, saturated aq. NaHCO$_3$, water, and brine. The organic layer was collected, dried over Na$_2$SO$_4$, filtered, and concentrated by rotary evaporation. Purification by silica flash chromatography (0-80% EtOAc/CH$_2$Cl$_2$) yielded partially purified picolinamide compound 1. Further purification by HPLC, then silica flash chromatography (0-20% 1.5 N NH$_3$ in MeOH/CH$_2$Cl$_2$) yielded compound 1 (72 mg, 48%) as a white solid.

$^1$H NMR (500 MHz, DMSO-d$_6$) δ 10.92 (s, 1H), 8.90 (dd, J=8.4, 3.1 Hz, 1H), 7.90 (td, J=7.9, 2.8 Hz, 1H), 7.66 (dd, J=7.3, 2.8 Hz, 1H), 7.52 (dd, J=7.8, 2.2 Hz, 2H), 7.39 (td, J=7.5, 2.2 Hz, 2H), 7.36-7.27 (m, 1H), 7.09 (dd, J=8.3, 2.9 Hz, 1H), 5.59-5.36 (m, 2H), 4.92-4.67 (m, 1H), 2.83 (tdd, J=17.0, 5.5, 2.7 Hz, 1H), 2.55 (dt, J=17.0, 3.9 Hz, 1H), 2.25 (qt, J=13.1, 3.7 Hz, 1H), 2.07-1.96 (m, 1H).

LC-MS m/z (rel int): (pos) 339.9 ([M+H]$^+$.

Example 2: Synthesis of N-(2,6-dioxopiperidin-3-yl)picolinamide (2)

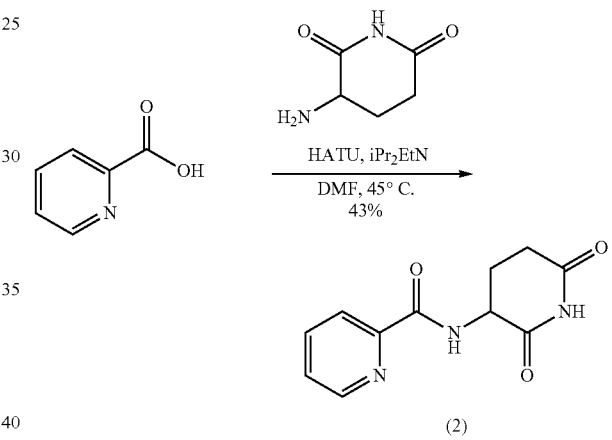

In an 8-mL vial, picolinic acid (115 mg, 0.93 mmol) was dissolved in DMF (0.5 M). Diisopropylethylamine (487 μL, 2.8 mmol, 3.0 equiv) and HATU (389 mg, 1.02 mmol, 1.1 equiv), and amino glutarimide (168 mg, 1.02 mmol, 1.1 equiv) were added sequentially. The reaction mixture was stirred at 45° C. overnight. Upon cooling to rt, the reaction mixture was diluted with CH$_2$Cl$_2$, washed with saturated. aq. NH$_4$Cl, saturated. aq. NaHCO$_3$, water, and brine. The organic layer was collected, dried over Na$_2$SO$_4$, filtered, and concentrated by rotary evaporation. Purification by silica flash chromatography (0-80% EtOAc/CH$_2$Cl$_2$, then 0-20% MeOH/CH$_2$Cl$_2$) yielded partially purified picolinamide 2. Further purification by HPLC, then silica flash chromatography (0-20% 1.5 N NH$_3$ in MeOH/CH$_2$Cl$_2$), yielded compound 2 (95 mg, 44%) as a white solid.

$^1$H NMR (500 MHz, DMSO-d$_6$) δ 10.87 (s, 1H), 9.08 (d, J=8.4 Hz, 1H), 8.68 (dt, J=4.7, 1.3 Hz, 1H), 8.16-7.91 (m, 2H), 7.64 (ddd, J=7.3, 4.8, 1.3 Hz, 1H), 4.80 (ddd, J=13.2, 8.3, 5.4 Hz, 1H), 2.81 (ddd, J=17.3, 13.7, 5.5 Hz, 1H), 2.54 (m, J=3.8 Hz, 1H), 2.22 (qd, J=12.9, 4.5 Hz, 1H), 2.01 (dtd, J=12.9, 5.4, 2.5 Hz, 1H).

LC-MS m/z (rel int): (pos) 233.0 ([M+H]$^+$.

Example 3: Synthesis of 6-amino-N-(2,6-dioxopiperidin-3-yl)picolinamide (3)

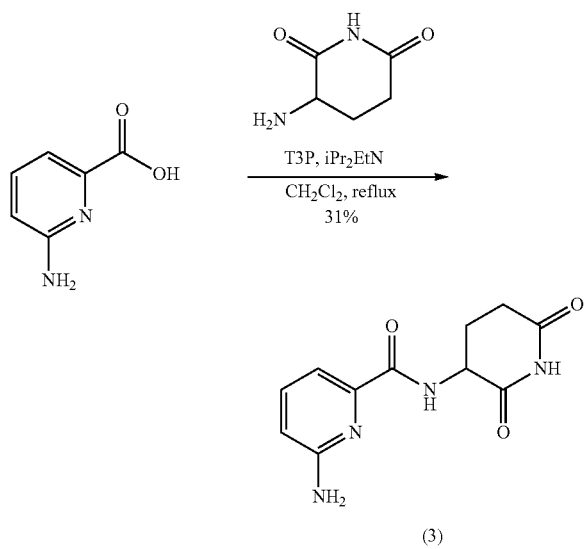

In an 8-mL vial, 6-aminopyridine-2-carboxylic acid (125 mg, 0.91 mmol) was dissolved in $CH_2Cl_2$ (0.3 M). Diisopropylethylamine (477 μL, 2.7 mmol, 3.0 equiv) and propylphosphonic anhydride (T3P, >50 wt %, 1.1 mmol, 1.2 equiv), and amino glutarimide (180 mg, 1.1 mmol, 1.2 equiv) were added sequentially. The reaction mixture was stirred at 45° C. overnight. Upon cooling to rt, the reaction mixture was diluted with water and extracted with $CH_2Cl_2$ 3×. The organic layer was collected, dried over $Na_2SO_4$, filtered, and concentrated by rotary evaporation. Purification by HPLC yielded compound 3 (70 mg, 31%).

LC-MS m/z (rel int): (pos) 249.0 ([M+H]$^+$.

Example 4: 4-chloro-N-(2,6-dioxopiperidin-3-yl)picolinamide (4)

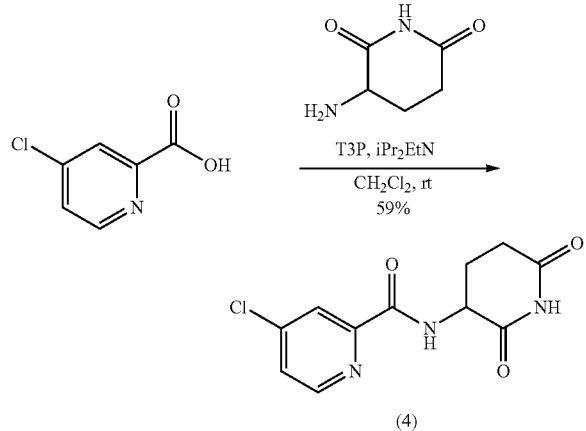

In an 8-mL vial, 4-chloropyridine-2-carboxylic acid (199 mg, 1.27 mmol) was dissolved in $CH_2Cl_2$ (0.3 M). Diisopropylethylamine (286 μL, 1.65 mmol, 1.3 equiv) and propylphosphonic anhydride (T3P, >50 wt %, 1.52 mmol, 1.2 equiv), and amino glutarimide (250 mg, 1.52 mmol, 1.2 equiv) were added sequentially. The reaction mixture was stirred at rt for 3 h. The reaction mixture was diluted with water and extracted with $CH_2Cl_2$ 3×. The organic layer was collected, dried over $Na_2SO_4$, filtered, and concentrated by rotary evaporation. Purification by silica flash chromatography (0-20% MeOH/$CH_2Cl_2$) yielded compound 4 (200 mg, 59%).

$^1$H NMR (500 MHz, DMSO-$d_6$) δ 10.88 (s, 1H), 9.16 (d, J=8.5 Hz, 1H), 8.67 (d, J=5.2 Hz, 1H), 8.06 (d, J=2.1 Hz, 1H), 7.81 (dd, J=5.2, 2.1 Hz, 1H), 4.80 (ddd, J=13.2, 8.5, 5.3 Hz, 1H), 2.81 (ddd, J=17.3, 13.8, 5.5 Hz, 1H), 2.56-2.51 (m, 1H), 2.22 (qd, J=13.0, 4.5 Hz, 1H), 2.00 (dtd, J=12.9, 5.5, 2.5 Hz, 1H).

LC-MS m/z (rel int): (pos) 267.9 ([M+H]$^+$.

Example 5: 2-(benzylamino)-N-(2,6-dioxopiperidin-3-yl)pyrimidine-4-carboxamide (5)

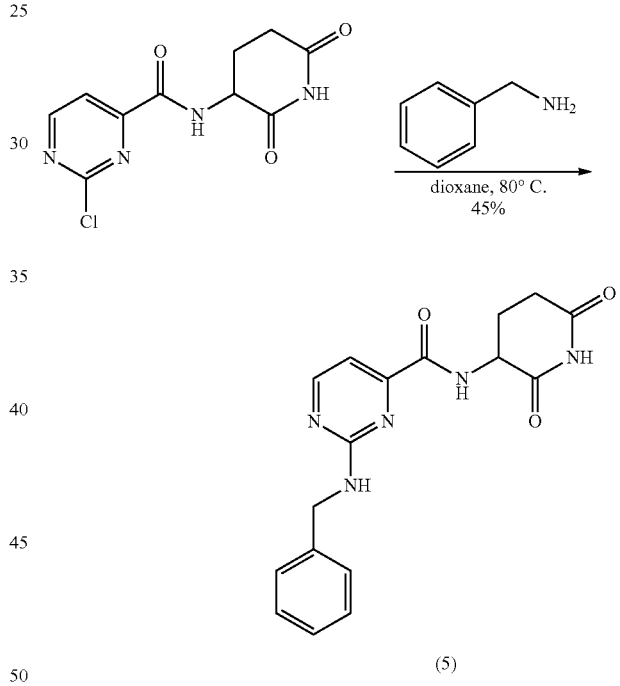

To a solution of chloropyrimidine (19 mg, 0.071 mmol) in dioxane (0.05 M) was added benzylamine (7.8 μL, 0.071 mmol, 1.0 equiv). The reaction was stirred at 80° C. for 2 h. Upon cooling to rt, the reaction mixture was diluted with 1 N NaOH and extracted with $CH_2Cl_2$ 3×. The organic layer was collected, dried over $Na_2SO_4$, filtered, and concentrated by rotary evaporation. Purification by HPLC provided compound 5 (11 mg, 45%).

$^1$H NMR (500 MHz, DMSO-$d_6$) δ 10.93 (s, 1H), 8.51 (d, J=4.8 Hz, 1H), 7.38 (m, 2H), 7.30 (t, J=7.6 Hz, 2H), 7.25-7.16 (m, 1H), 7.09 (d, J=4.8 Hz, 1H), 4.76 (ddd, J=13.0, 8.2, 5.4 Hz, 1H), 4.61 (m, 2H), 2.80 (ddd, J=17.3, 13.7, 5.5 Hz, 1H), 2.54 (m, J=5.1 Hz, 1H), 2.25-2.08 (m, 1H), 2.07-1.96 (m, 1H).

LC-MS m/z (rel int): (pos) 340.0 ([M+H]+.

Example 6: Synthesis of N-(2,6-dioxopiperidin-3-yl)-6-methoxypicolinamide (6)

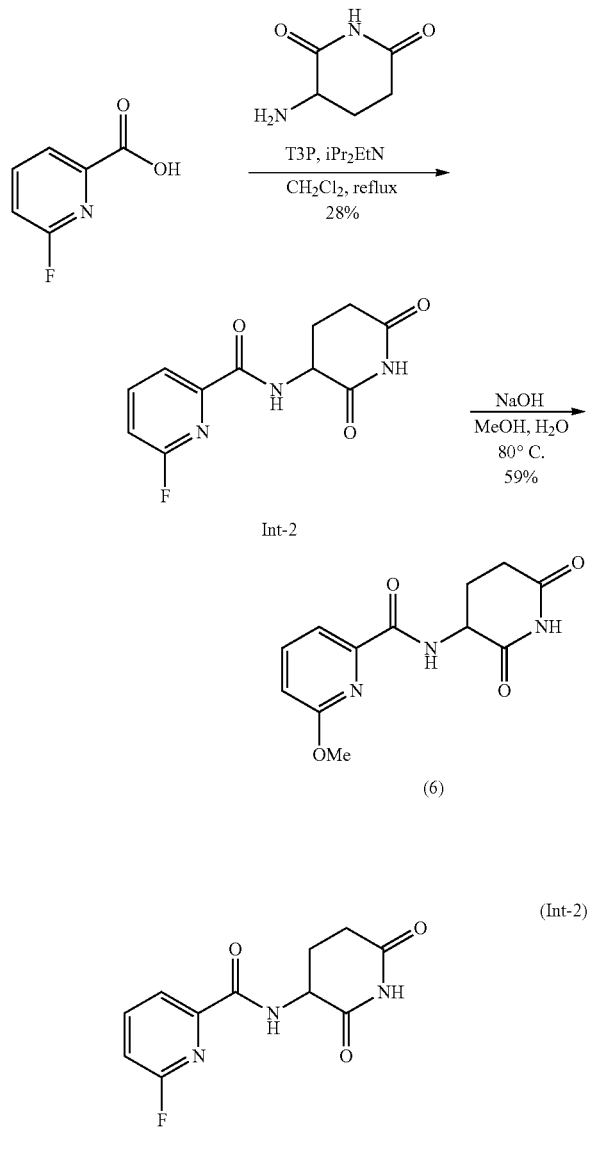

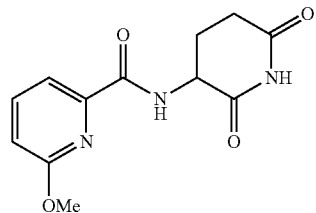

To a solution of fluoropyridine Int-2 (37 mg, 0.27 mmol) in MeOH (0.3 M) was added 10 N NaOH (500 µL). The reaction was stirred at 80° C. for 2 h. Upon cooling to rt, the reaction mixture was diluted with saturated. aq. NH$_4$Cl and extracted with CH$_2$Cl$_2$ 3×. The organic layer was collected, dried over Na$_2$SO$_4$, filtered, and concentrated by rotary evaporation. Purification by silica flash chromatography (0-80% EtOAc/CH$_2$Cl$_2$, then 0-20% MeOH/CH$_2$Cl$_2$) yielded compound 6 (41 mg, 59%).

LC-MS m/z (rel int): (pos) 263.0 ([M+H]$^+$.

Example 7: Synthesis of 2-(benzyloxy)-N-(2,6-dioxopiperidin-3-yl)pyrimidine-4-carboxamide (7)

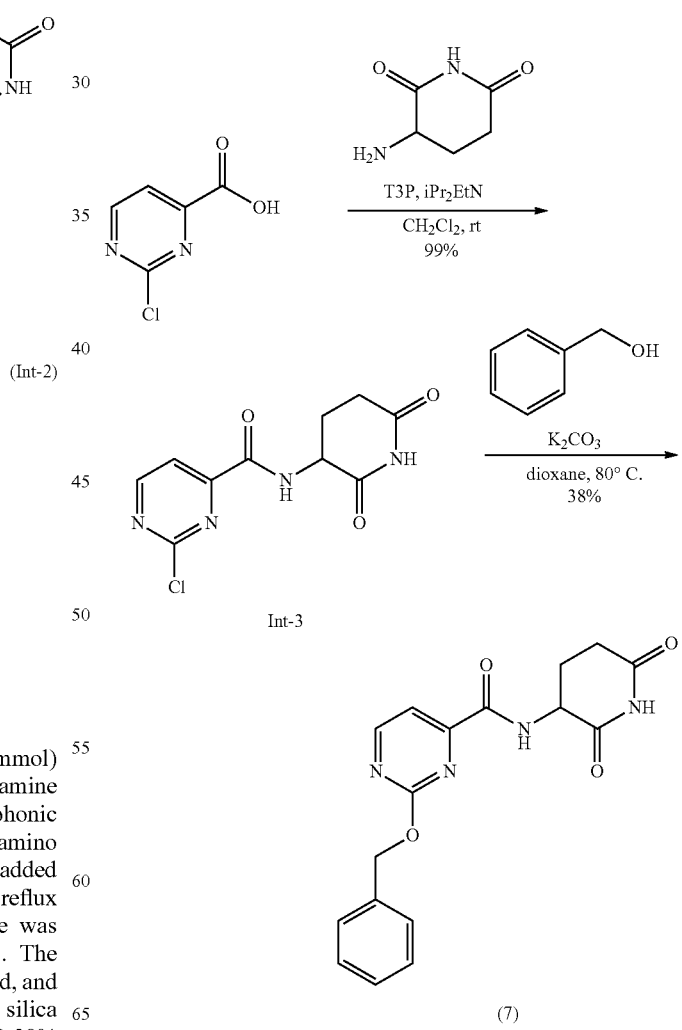

In an 8-mL vial, 6-fluoropicolinic acid (1.5 g, 10.9 mmol) was dissolved in CH$_2$Cl$_2$ (0.5 M). Diisopropylethylamine (5.7 mL, 32.6 mmol, 3.0 equiv) and propylphosphonic anhydride (T3P, >50 wt %, 13 mmol, 1.2 equiv), and amino glutarimide (2.14 g, 13 mmol, 1.2 equiv) were added sequentially. The reaction mixture was stirred at reflux overnight. Upon cooling to rt, the reaction mixture was diluted with water and extracted with CH$_2$Cl$_2$ 3×. The organic layer was collected, dried over Na$_2$SO$_4$, filtered, and concentrated by rotary evaporation. Purification by silica flash chromatography (0-80% EtOAc/CH$_2$Cl$_2$, then 0-20% MeOH/CH$_2$Cl$_2$) yielded compound Int-2 (755 mg, 28%).

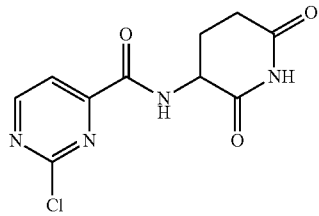

(Int-3)

In a 20-mL vial, 2-chloropyrimidine-4-carboxylic acid (430 mg, 2.7 mmol) was dissolved in CH$_2$Cl$_2$ (0.3 M). Diisopropylethylamine (1.42 mL, 8.1 mmol, 3.0 equiv) and propylphosphonic anhydride (T3P, >50 wt %, 3.3 mmol, 1.2 equiv), and amino glutarimide (536 mg, 3.3 mmol, 1.2 equiv) were added sequentially. The reaction mixture was stirred at rt overnight. The reaction mixture was diluted with water and extracted with CH$_2$Cl$_2$ 3×. The organic layer was collected, dried over Na$_2$SO$_4$, filtered, and concentrated by rotary evaporation. Purification by silica flash chromatography (0-80% EtOAc/CH$_2$Cl$_2$) yielded imide Int-3 (719 mg, 99%).

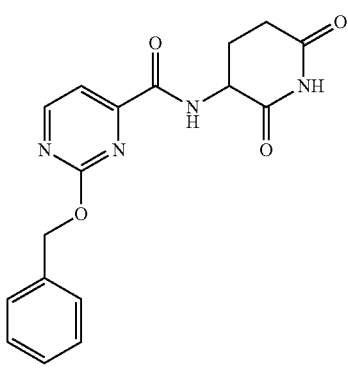

(7)

To a solution of chloropyrimidine Int-3 (94 mg, 0.35 mmol) in dioxane (0.35 M) was added benzyl alcohol (181 μL, 1.74 mmol, 5.0 equiv) and potassium carbonate (241 mg, 1.74 mmol, 5.0 equiv). The reaction was stirred at 80° C. overnight. Upon cooling to rt, the reaction mixture was diluted with saturated. aq. NH$_4$Cl and extracted with CH$_2$Cl$_2$ 3×. The organic layer was collected, washed with water, dried over Na$_2$SO$_4$, filtered, and concentrated by rotary evaporation. Purification by HPLC provided compound 7 (45 mg, 38%).

$^1$H NMR (500 MHz, DMSO-d$_6$) δ 10.93 (s, 1H), 8.51 (d, J=4.8 Hz, 1H), 7.38 (m, 2H), 7.30 (t, J=7.6 Hz, 2H), 7.21 (t, J=7.2 Hz, 1H), 7.09 (d, J=4.8 Hz, 1H), 4.76 (ddd, J=13.1, 8.2, 5.4 Hz, 1H), 4.61 (m, 1H), 2.80 (ddd, J=17.3, 13.7, 5.6 Hz, 1H), 2.57-2.52 (m, 1H), 2.24-2.10 (m, 1H), 2.08-2.00 (m, 1H).

LC-MS m/z (rel int): (pos) 339.9 ([M+H]$^+$.

Example 8: Synthesis of N-(2,6-dioxopiperidin-3-yl)quinoline-8-carboxamide (8)

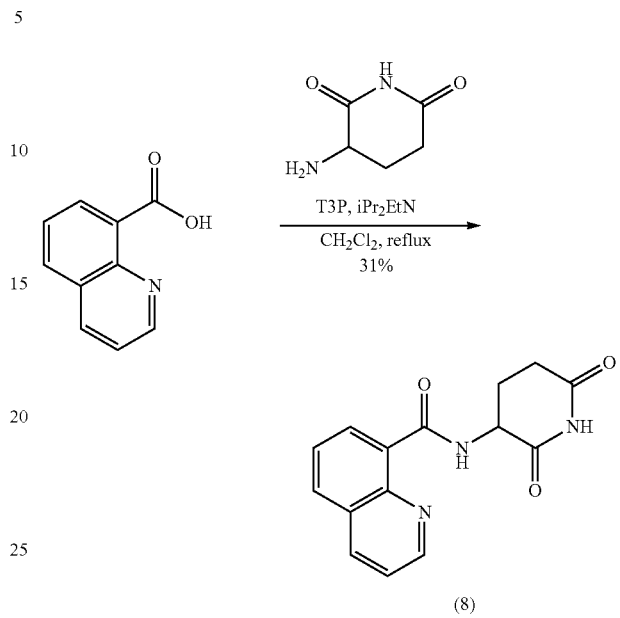

(8)

In an 8-mL vial, quinoline-8-carboxylic acid (210 mg, 1.2 mmol) was dissolved in CH$_2$—Cl$_2$ (0.4 M). Diisopropylethylamine (630 mL, 3.6 mmol, 3.0 equiv) and propylphosphonic anhydride (T3P, >50 wt %, 1.5 mmol, 1.2 equiv), and amino glutarimide (2.14 g, 1.5 mmol, 1.2 equiv) were added sequentially. The reaction mixture was stirred at reflux for 5 h. Upon cooling to rt, the reaction mixture was diluted with water and extracted with CH$_2$Cl$_2$ 3×. The organic layer was collected, dried over Na$_2$SO$_4$, filtered, and concentrated by rotary evaporation. Purification by silica flash chromatography (0-80% EtOAc/CH$_2$Cl$_2$, then 0-20% MeOH/CH$_2$Cl$_2$) yielded compound 8 (105 mg, 31%).

$^1$H NMR (500 MHz, DMSO-d$_6$) δ 11.55 (d, J=7.1 Hz, 1H), 10.94 (s, 1H), 9.04 (dd, J=4.2, 1.6 Hz, 1H), 8.64 (dd, J=7.3, 1.6 Hz, 1H), 8.60 (dd, J=8.3, 1.5 Hz, 1H), 8.25 (dd, J=8.2, 1.2 Hz, 1H), 7.79 (t, J=7.7 Hz, 1H), 7.71 (dd, J=8.3, 4.3 Hz, 1H), 4.92 (ddd, J=12.4, 7.1, 5.3 Hz, 1H), 2.83 (ddd, J=17.4, 13.6, 5.5 Hz, 1H), 2.58 (dt, J=17.3, 3.5 Hz, 1H), 2.29 (dtd, J=13.1, 5.4, 2.3 Hz, 1H), 2.16 (qd, J=12.9, 4.4 Hz, 1H).

LC-MS m/z (rel int): (pos) 283.9 ([M+H]$^+$.

Example 9: Synthesis of N-(2,6-dioxopiperidin-3-yl)-1,2,3,4-tetrahydroquinoline-8-carboxamide (9)

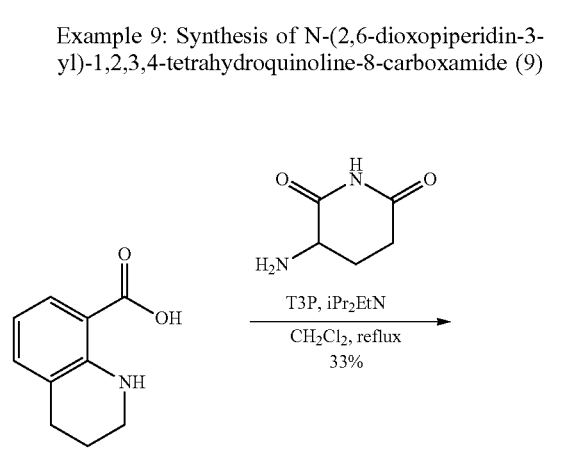

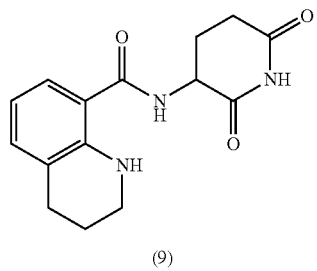

(9)

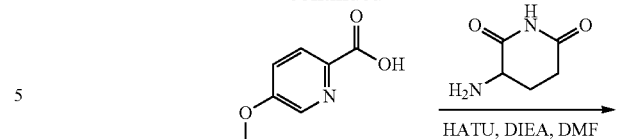

Exact Mass: 328.14
Int-6

In an 8-mL vial, 1,2,3,4-tetrahydroquinoline-8-carboxylic acid (45 mg, 0.25 mmol) was dissolved in $CH_2Cl_2$ (0.25 M). Diisopropylethylamine (132 µL, 0.76 mmol, 3.0 equiv) and propylphosphonic anhydride (T3P, >50 wt %, 1.2 mmol, 1.2 equiv), and amino glutarimide (50 mg, 0.30 mmol, 1.2 equiv) were added sequentially. The reaction mixture was stirred at reflux for 12 h. Upon cooling to rt, the reaction mixture was diluted with water and extracted with $CH_2Cl_2$ 3×. The organic layer was collected, dried over $Na_2SO_4$, filtered, and concentrated by rotary evaporation. Purification by silica flash chromatography (0-80% EtOAc/$CH_2Cl_2$, then 0-20% MeOH/$CH_2Cl_2$) yielded compound 9 (24 mg, 33%).

LC-MS m/z (rel int): (pos) 288.1 ([M+H]$^+$).

Example 10: Synthesis of N-(2,6-dioxopiperidin-3-yl)-5-((4-(morpholinomethyl)benzyl)oxy)picolinamide (11)

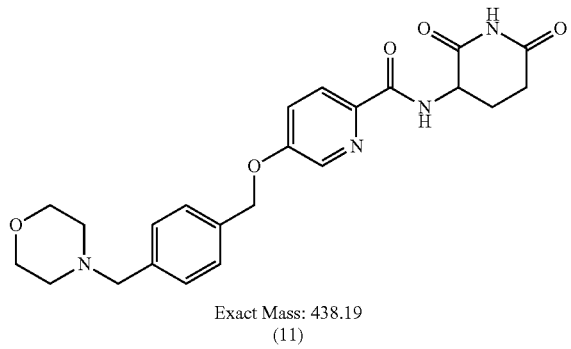

Exact Mass: 438.19
(11)

4-(4-(Chloromethyl)benzyl)morpholine (Int-4)

A solution of (4-(morpholinomethyl)phenyl)methanol (1 g, 4.83 mmol, 1.0 eq), $SOCl_2$ (2 mL) in dichloromethane (8 mL) was stirred at room temperature for 3 h. Thin layer chromatography (TLC) showed that the reaction reached completion. The reaction mixture was diluted with water and extracted with EtOAc. The combined organic layers were washed with water, aqueous NaOH (1 N) and brine, dried and concentrated by rotary evaporation to give compound Int-4 (1 g, 92%) as off-white solid.

ESI-MS (EI$^+$, m/z): 226.1.

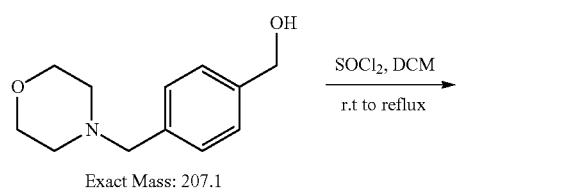

Exact Mass: 207.1

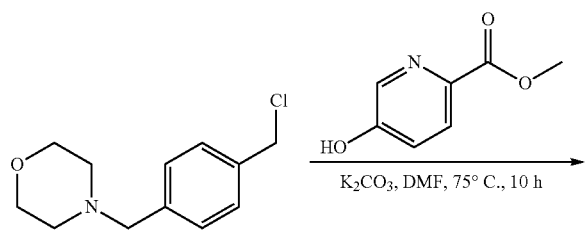

Exact Mass: 225.09
Int-4

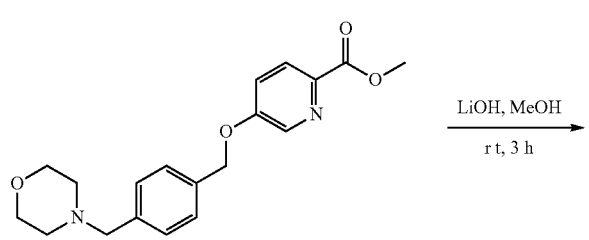

Exact Mass: 342.16
Int-5

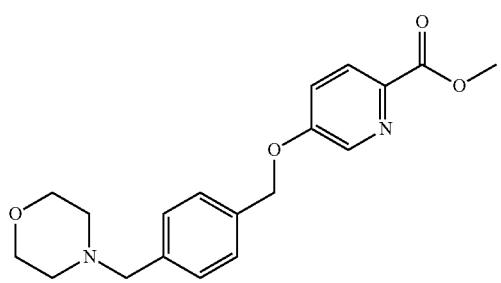 [SMILES: COC(=O)c1ccc(OCc2ccc(CN3CCOCC3)cc2)cn1]

Methyl 5-((4-(morpholinomethyl)benzyl)oxy)picolinate (Int-5)

A solution of compound Int-4 (741 mg, 3.27 mmol, 1.0 eq), methyl 5-hydroxypicolinate (500 mg, 3.27 mmol), and K$_2$CO$_3$ (900 mg, 6.54 mmol, 1.0 eq) in DMF (6 mL) was stirred at 70° C. for 16 h. TLC showed that the reaction reached completion. H$_2$O (10 mL) was added and the mixture was extracted with EtOAc (2×20 mL). The combined organic layers were washed with water (20 mL) and brine (20 mL), dried over Na$_2$SO$_4$ and concentrated by rotary evaporation. The residue was purified by column chromatography (dichloromethane/MeOH:40/1) to afford compound Int-5 (960 mg, 86%) as a white solid.

$^1$H NMR (400 MHz, DMSO-d$_6$): δ 8.44 (d, J=2.8 Hz, 1H), 8.04 (d, J=8.7 Hz, 1H), 7.59 (dd, J=8.8, 2.9 Hz, 1H), 7.43 (d, J=8.0 Hz, 2H), 7.34 (d, J=8.0 Hz, 2H), 5.25 (s, 2H), 3.84 (s, 3H), 3.59-3.53 (m, 4H), 3.46 (s, 2H), 2.39-2.30 (m, 4H).

ESI-MS (EI$^+$, m/z): 343.2.

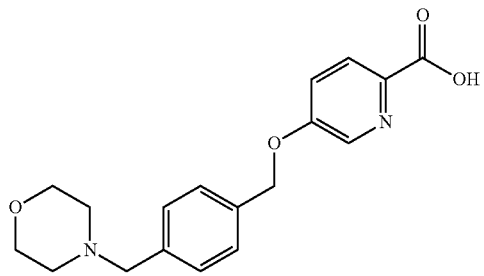 [SMILES: O=C(O)c1ccc(OCc2ccc(CN3CCOCC3)cc2)cn1]

5-((4-(Morpholinomethyl)benzyl)oxy)picolinic acid (Int-6)

To a mixture of compound Int-5 (500 mg, 1.46 mmol) in MeOH (2 mL) and H$_2$O (1 mL) was added LiOH·H$_2$O (122 mg, 2.92 mmol, 2.0 eq). The reaction mixture was stirred at room temperature for 3 h. The crude mixture was concentrated by rotary evaporation and the pH was adjusted to 3-4 with aqueous HCl (1 M). The obtained suspension was filtered and the solid was dried to afford compound Int-6 (430 mg, 89.6%) as a white solid.

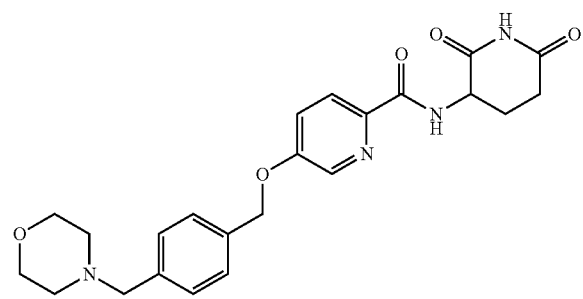 [SMILES: O=C1CCC(NC(=O)c2ccc(OCc3ccc(CN4CCOCC4)cc3)cn2)C(=O)N1]

N-(2,6-dioxopiperidin-3-yl)-5-((4-(morpholinomethyl)benzyl)oxy)picolinamide (11)

HATU (408 mg, 1.8 mmol, 1.2 eq) was added to a mixture of compound Int-6 (500 mg, 1.5 mmol, 1.0 eq), 3-aminopiperidine-2,6-dione hydrochloride (300 mg, 1.8 mmol, 1.2 eq) and DIEA (348 mg, 3.0 mmol, 2.0 eq) in DMF (2 mL) at 0-5° C. The resulting mixture was allowed to warm to room temperature and was stirred for 1 h. Water was added and the mixture was extracted with EtOAc (2×15 mL). The combined organic layers were washed with water (15 mL) and brine (15 mL), dried over Na$_2$SO$_4$ and concentrated by rotary evaporation. The residue was purified by prep-HPLC to afford compound 11 (80 mg, 12%) as a white solid.

$^1$H NMR (400 MHz, DMSO-d$_6$): δ 10.85 (s, 1H), 10.02 (s, 1H), 8.87 (d, J=8.4 Hz, 1H), 8.41 (d, J=2.8 Hz, 1H), 8.03 (d, J=8.8 Hz, 1H), 7.64 (dd, J=3.2, 8.8 Hz, 1H), 7.60 (d, J=8.0 Hz, 2H), 7.54 (d, J=8.0 Hz, 2H), 5.33 (s, 2H), 4.72-4.79 (m, 1H), 4.36 (s, 2H), 3.96 (d, J=13.0 Hz, 2H), 3.68-3.56 (m, 2H), 3.26 (m, 2H), 3.13 (m, 2H), 2.75-2.84 (m, 1H), 2.53-2.58 (m, 1H), 2.111-2.11 (m, 1H), 2.04-1.96 (m, 1H).

ESI-MS (EI$^+$, m/z): 439.25.

Example 11: Synthesis of N-(2,6-dioxopiperidin-3-yl)-2-oxo-1,2-dihydropyridine-3-carboxamide (19)

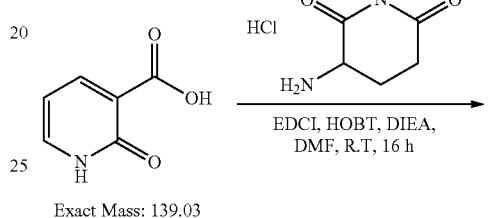

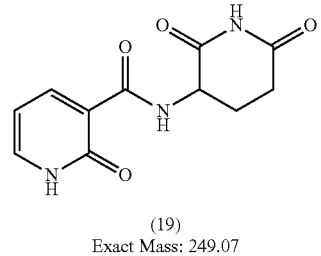

(19)
Exact Mass: 249.07

1-Ethyl-3-(3-dimethylaminopropyl)carbodiimide (EDCI) (1 g, 5.4 mmol, 1.5 eq) and hydroxybenzotriazole (HOBt) (729 mg, 5.4 mmol, 1.5 eq) were added to a mixture of 2-oxo-1,2-dihydropyridine-3-carboxylic acid (500 mg, 3.6 mmol, 1.0 eq), 3-aminopiperidine-2,6-dione hydrochloride (506 mg, 3.9 mmol, 1.1 eq) and diisopropylethylamine (DIEA) (1161 mg, 9.0 mmol, 2.5 eq) in DMF (6 mL) at 0-5° C. The resulting mixture was allowed to warm to room temperature and was stirred for 16 h. Water was added and the aqueous layer was extracted with EtOAc (2×50 mL). The combined organic layers were washed with H$_2$O and brine, and dried over Na$_2$SO$_4$. The solvent was removed by rotary evaporation and the residue was purified by prep-HPLC to afford the product (19) (23 mg) as a yellow solid.

$^1$H NMR (400 MHz, DMSO-d$_6$) δ2.04 (td, J=4.4, 12.8 Hz, 1H), 2.52-2.54 (m, 1H), 2.13-2.19 (m, 1H), 2.71-2.80 (m, 1H), 4.72-4.78 (m, 1H), 6.49 (t, J=6.4 Hz, 1H), 7.73 (td, J=2.0, 6.4 Hz, 1H), 8.35 (dd, J=2.4, 7.2 Hz, 1H), 10.19 (d, J=7.2 Hz, 1H), 10.87 (s, 1H), 12.53 (s, 1H).

ESI-MS (EI$^+$, m/z): 250.15.

Example 12: Synthesis of N-(2,6-dioxopiperidin-3-yl)-1-methyl-2-oxo-1,2-dihydropyridine-3-carboxamide (20)

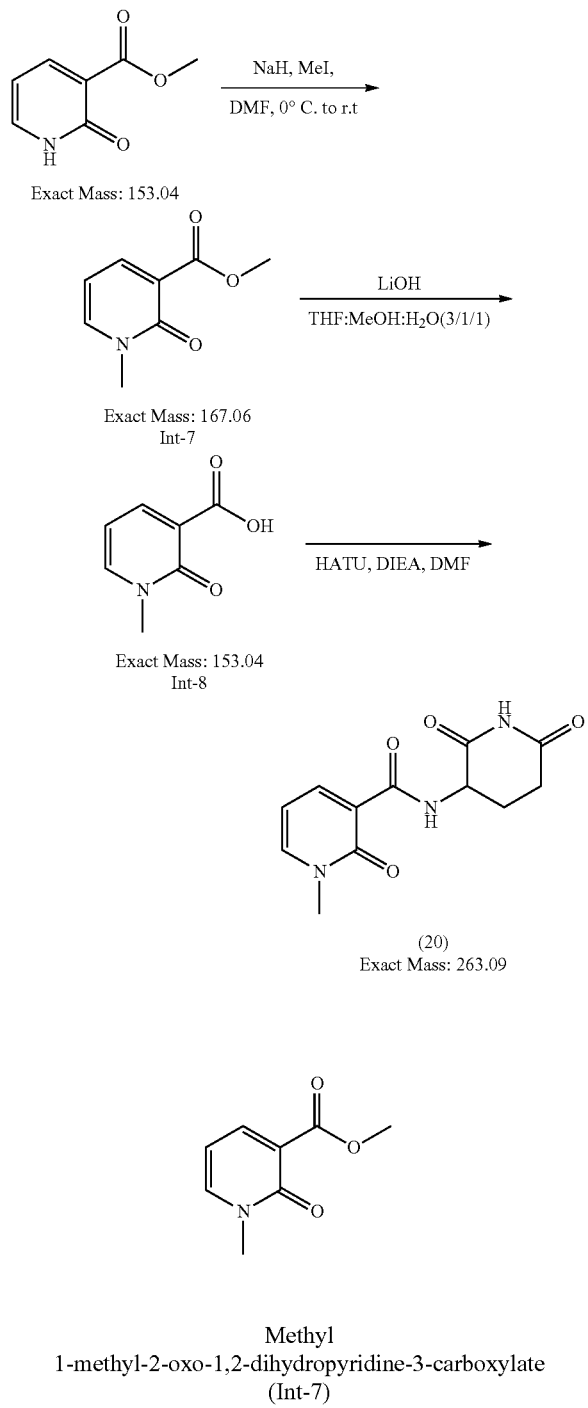

partitioned between ethyl acetate and water. The combined organic layers were washed with water and brine, dried over $Na_2SO_4$ and concentrated by rotary evaporation to afford compound Int-7 (500 mg, 50%) as a yellow solid.

ESI-MS (EI⁺, m/z): 168.15.

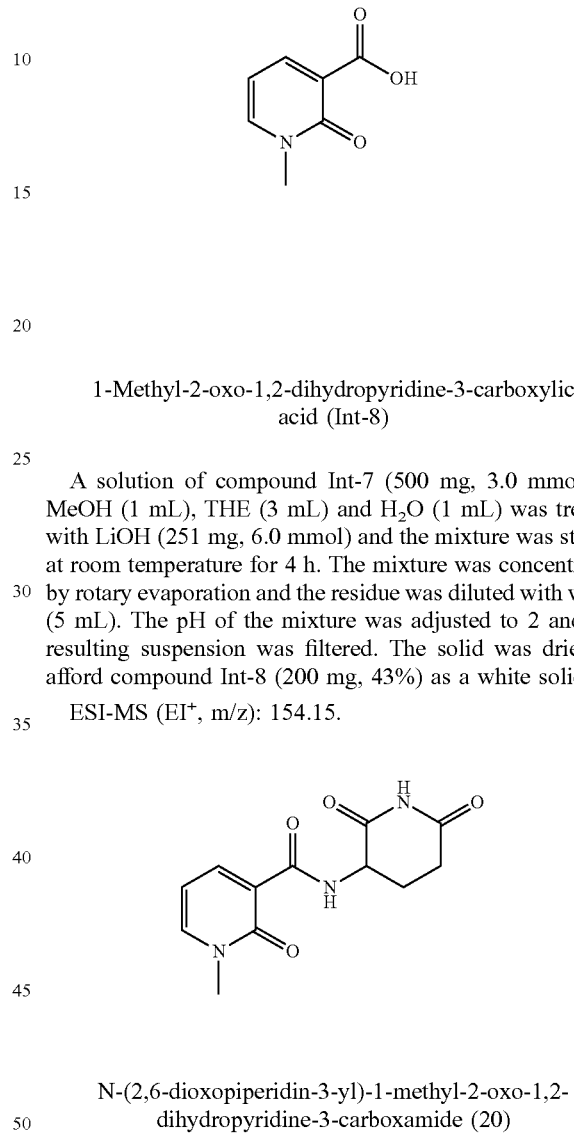

1-Methyl-2-oxo-1,2-dihydropyridine-3-carboxylic acid (Int-8)

A solution of compound Int-7 (500 mg, 3.0 mmol) in MeOH (1 mL), THF (3 mL) and $H_2O$ (1 mL) was treated with LiOH (251 mg, 6.0 mmol) and the mixture was stirred at room temperature for 4 h. The mixture was concentrated by rotary evaporation and the residue was diluted with water (5 mL). The pH of the mixture was adjusted to 2 and the resulting suspension was filtered. The solid was dried to afford compound Int-8 (200 mg, 43%) as a white solid.

ESI-MS (EI⁺, m/z): 154.15.

N-(2,6-dioxopiperidin-3-yl)-1-methyl-2-oxo-1,2-dihydropyridine-3-carboxamide (20)

To a solution of compound Int-8 (200 mg, 1.3 mmol) in DMF (5 mL) was added 3-aminopiperdine-2,6-dione (297 mg, 1.3 mmol and DIEA (387 mg, 1.3 mmol) at 0° C. HATU was then added slowly (456 mg, 1.8 mmol) at 0° C. The reaction was allowed to warm to room temperature and was stirred for 6 h. The mixture was filtered and the isolated solid was triturated with DMF (5 mL). The resulting suspension was filtered and the filtrate cake was dried to afford the product (20) (50 mg) as a white solid.

$^1$H NMR (400 MHz, DMSO-$d_6$) δ 10.89 (s, 1H), 10.25 (d, J=7.2 Hz, 1H), 8.33 (dd, J=2.4, 7.2 Hz, 1H), 8.08 (dd, J=2.8, 6.8 Hz, 1H), 6.52 (t, J=7.2 Hz, 1H), 4.72-4.78 (m, 1H), 3.57 (s, 3H), 2.74-2.81 (m, 1H), 2.52-2.55 (m, 1H), 2.14-2.21 (m, 1H), 1.96-2.05 (m, 1H).

ESI-MS (EI⁺, m/z): 264.20.

Methyl 1-methyl-2-oxo-1,2-dihydropyridine-3-carboxylate (Int-7)

NaH (313 mg, 13.1 mmol) was added in portions to a solution of methyl 2-oxo-1,2-dihydropyridine-3-carboxylate (1 g, 6.5 mmol) in DMF (8 mL) at 0° C. and the reaction mixture was stirred at 0° C. for 0.5 h. MeI (1.8 g, 13.1 mmol) was added dropwise at 0° C. and the resulting mixture was stirred at room temperature for 5 h. TLC showed that the reaction reached completion. The reaction mixture was

Example 13: Synthesis of N-(2,6-dioxopiperidin-3-yl)-2-oxo-1-phenyl-1,2-dihydropyridine-3-carboxamide (21)

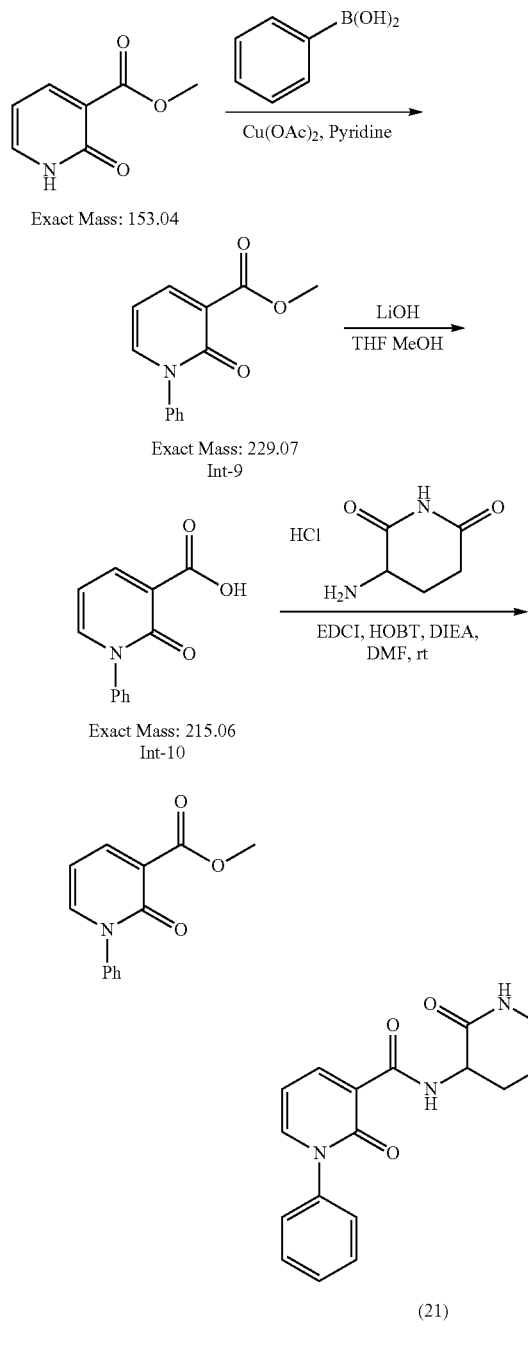

Methyl 2-oxo-1-phenyl-1,2-dihydropyridine-3-carboxylate (Int-9)

A mixture of methyl 2-oxo-1,2-dihydropyridine-3-carboxylate (1.53 g, 10 mmol), phenylboronic acid (3.6 g, 30 mmol), molecular sieves (2.8 g, 12 mmol) and Cu(OAc)$_2$ (3.6 g, 20 mmol) in DCM (60 ml) was treated with pyridine (2.4 ml, 30 mmol). The mixture was stirred at room temperature for 12 h. TLC showed that the reaction reached completion. The reaction mixture was filtered through a celite pad and the filtrate was concentrated by rotary evaporation to give the compound Int-9 (1.8 g, 78%) as a yellow solid.

ESI-MS (EI+, m/z): 230.15.

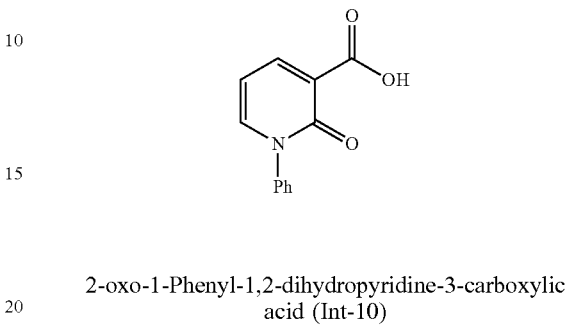

2-oxo-1-Phenyl-1,2-dihydropyridine-3-carboxylic acid (Int-10)

A solution of compound Int-9 (800 mg, 3.5 mmol) in MeOH (2 mL), THF (6 mL) and H$_2$O (2 mL) was treated with LiOH H$_2$O (293 mg, 7.0 mmol) and the mixture was stirred at room temperature for 4 h. Then the mixture was concentrated under reduced pressure and the residue was diluted with water (8 mL). The pH of mixture was adjusted to 2 and the resulting suspension was filtered. The isolated solid was dried to afford the compound Int-10 (650 mg, 86%) as a yellow solid.

ESI-MS (EI+, m/z): 216.10.

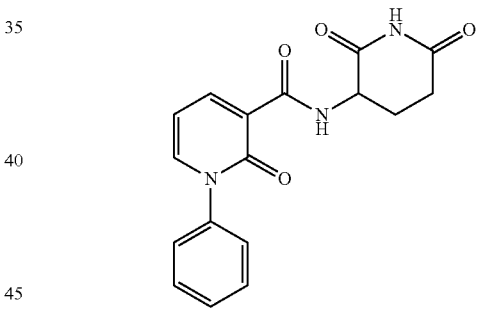

N-(2,6-dioxopiperidin-3-yl)-2-oxo-1-phenyl-1,2-dihydropyridine-3-carboxamide (21)

To a solution of compound Int-10 (450 mg, 2.1 mmol) in DMF (5 mL) was added 3-aminopiperdine-2,6-dione (413 mg, 2.5 mmol) and DIEA (542 mg, 4.2 mmol) at 0° C. HATU (951 mg, 2.5 mmol) was then added slowly at 0° C. The reaction was allowed to warm to room temperature and was stirred for 10 h. The mixture was filtered and the isolated solid was triturated with DMF (10 mL). The resulting mixture was filtered and the filtrate cake was dried to afford the product (21) (300 mg, 43%) as a white solid.

$^1$H NMR (400 MHz, DMSO-d$_6$) δ 10.89 (s, 1H), 10.06 (d, J=7.2 Hz, 1H), 8.465 (dd, J=2.0, 7.2 Hz, 1H), 8.03 (dd, J=1.6, 6.4 Hz, 1H), 7.46-7.58 (m, 5H), 6.627 (t, J=6.8 Hz, 1H), 4.72-4.78 (m, 1H), 2.72-2.80 (m, 1H), 2.48-2.54 (m, 1H), 2.14-2.20 (m, 1H), 1.93-2.04 (m, 1H).

ESI-MS (EI+, m/z): 326.15.

Example 14: Synthesis of 1-Benzyl-N-(2,6-dioxopiperidin-3-yl)-2-oxo-1,2-dihydropyridine-3-carboxamide (22)

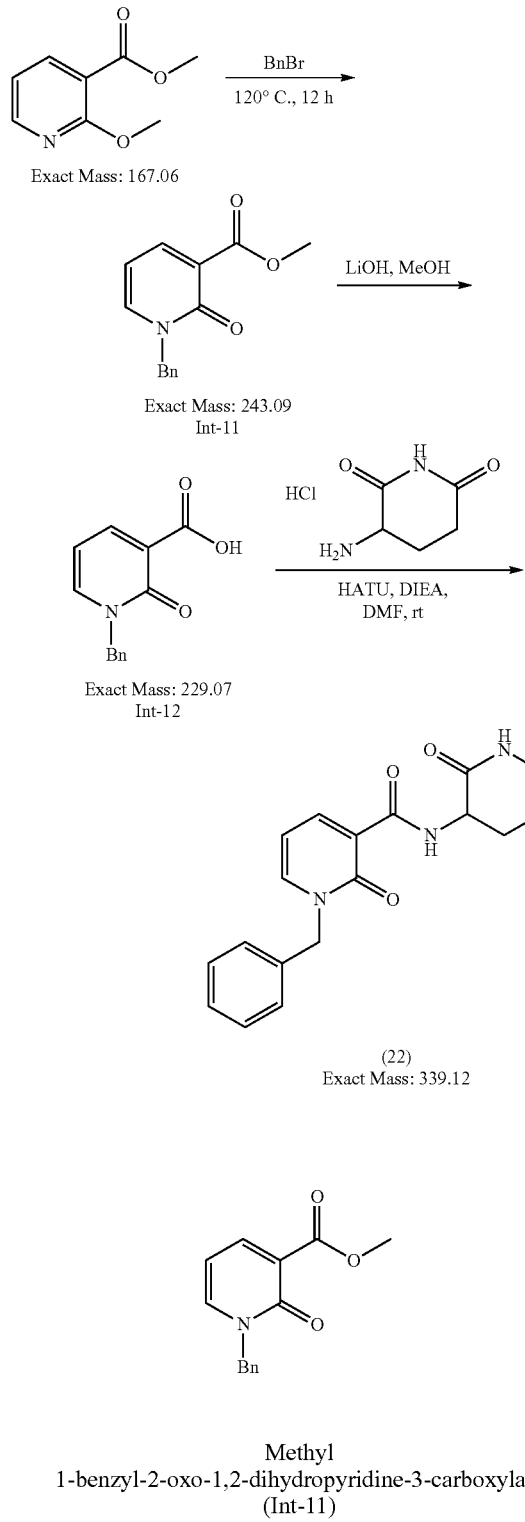

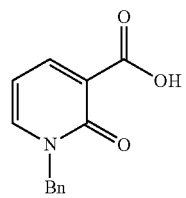 [SMILES: O=C(O)c1cccn(Cc2ccccc2)c1=O]

Methyl 1-benzyl-2-oxo-1,2-dihydropyridine-3-carboxylate (Int-11)

A solution of methyl 2-methoxynicotinate (2 g, 11.9 mmol) in BnBr (2.6 g, 15.2 mmol) was heated to 120° C. for 20 h. TLC showed that the reaction reached completion. The solvent was removed by rotary evaporation and the residue was purified by column chromatography (hexanes/ethyl acetate:3/1) to afford the compound Int-11 (1.6 g, 54.8%) as a yellow solid.

ESI-MS (EI+, m/z): 244.1.

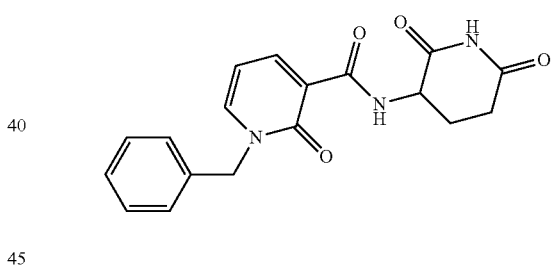

1-Benzyl-2-oxo-1,2-dihydropyridine-3-carboxylic acid (Int-12)

To a mixture of compound Int-11 (500 mg, 2.05 mmol) in MeOH (1 mL) and $H_2O$ (1 mL) was added LiOH $H_2O$ (172 mg, 4.10 mmol, 2.0 eq) and the mixture was stirred at room temperature for 4 h. The mixture was concentrated in vacuo and the pH was adjusted to 3-4 with aqueous HCl (1 M). The resulting suspension was filtered and the isolated solid was dried to afford compound Int-12 (460 mg, 97.6%) as a white solid.

ESI-MS (EI+, m/z): 230.1.

1-Benzyl-N-(2,6-dioxopiperidin-3-yl)-2-oxo-1,2-dihydropyridine-3-carboxamide (22)

HATU (988 mg, 2.6 mmol, 1.2 eq) was added to a mixture of compound Int-12 (460 mg, 2.1 mmol, 1.0 eq), 3-aminopiperidine-2,6-dione hydrochloride (429 mg, 2.6 mmol, 1.2 eq) and DIEA (703 mg, 5.5 mmol, 2.5 eq) in DMF (2 mL) at 0-5° C. The resulting mixture was allowed to warm to room temperature and was stirred for 3 h. Water was added and the resulting suspension was filtered. The filtrate cake was washed with $H_2O$ and was dried to afford compound 22 (578 mg, 78.1%) as an off-white powder.

$^1$H NMR (400 MHz, DMSO-$d_6$): δ 10.89 (s, 1H), 10.13 (d, J=6.8 Hz, 1H), 8.37 (d, J=6.8 Hz, 1H), 8.25 (d, J=6.4 Hz, 1H), 7.33-7.39 (m, 2H), 7.21-7.32 (m, 3H), 6.59 (t, J=6.8 Hz, 1H), 5.20-5.30 (m, 2H), 4.70-4.77 (m, 1H), 2.70-2.80 (m, 1H), 2.48-2.52 (m, 1H), 2.11-2.19 (m, 1H), 2.01 (qd, J=4.0, 12.8 Hz, 1H).

ESI-MS (EI+, m/z): 340.15.

Example 15: Synthesis of 5-Amino-N-(2,6-dioxopiperidin-3-yl) quinoline-8-carboxamide (23)

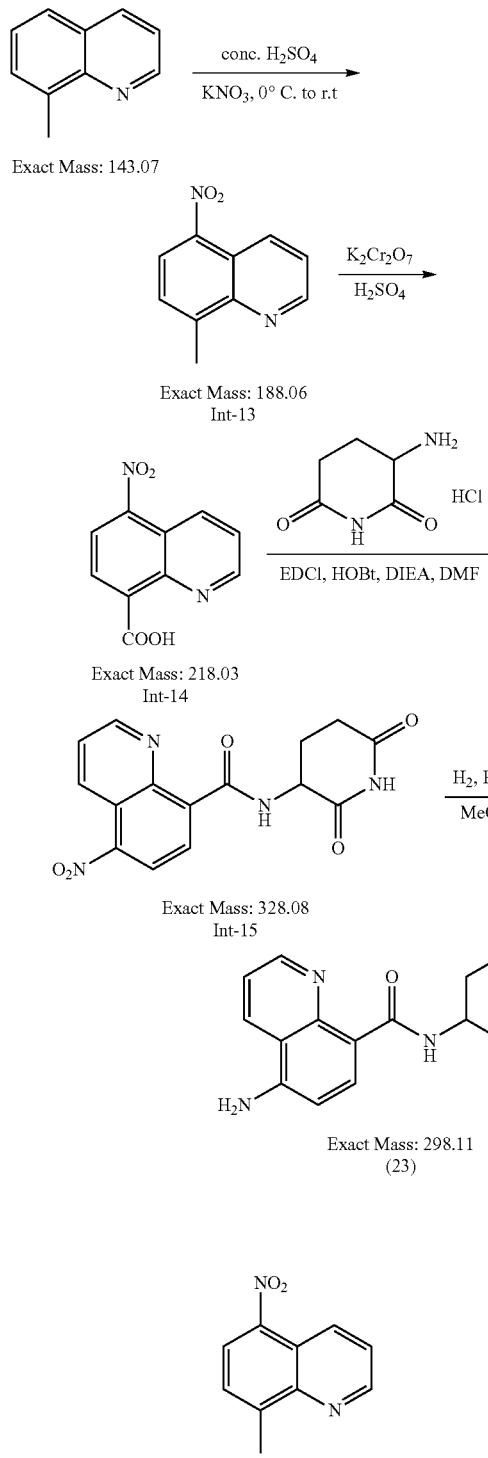

to the reaction mixture. The reaction was allowed to warm to room temperature and was stirred for 5 h. TLC showed that the reaction reached completion. The reaction mixture was basified to pH 9 with aqueous NaOH (2 N) and the resulting mixture was extracted with ethyl acetate. The combined organic layers were washed with water and brine, dried over $Na_2SO_4$ and concentrated under reduced pressure to give compound Int-13 (5.7 g, 86.8%) as a yellow solid.

$^1$H NMR (400 MHz, $CDCl_3$): δ 2.90 (s, 1H), 7.62-7.66 (m, 2H), 8.31 (d, J=8.0 Hz, 1H), 9.03-9.06 (m, 2H).

ESI-MS ($EI^+$, m/z): 189.10.

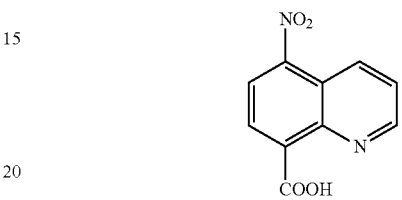

5-Nitroquinoline-8-carboxylic acid (Int-14)

A solution of compound Int-13 (1.5 g, 7.97 mmol) in conc. $H_2SO_4$ (12 mL) was stirred at 0° C. for about 30 minutes. Then $K_2Cr_2O_7$ (9.38 g, 31.88 mmol) was added slowly to the reaction mixture. The reaction was allowed to warm to room temperature and was stirred for 1 hour. TLC showed that the reaction reached completion. The reaction mixture was basified to pH 9 with NaOH aqueous (2 N) and then was acidified to pH 3 with HOAc, then extracted with ethyl acetate. The combined organic layers were washed with water and brine, dried over $Na_2SO_4$ and concentrated under reduced pressure to give the compound Int-14 (540 mg, 31.1%) as a yellow solid.

$^1$H NMR (400 MHz, $CDCl_3$): δ 7.89 (q, J=4.0 Hz, 1H), 8.50 (d, J=8.0 Hz, 1H), 8.93 (d, J=8.0 Hz, 1H), 9.09 (d, J=6.8 Hz, 1H), 9.20 (d, J=8.4 Hz, 1H).

ESI-MS ($EI^+$, m/z): 219.05.

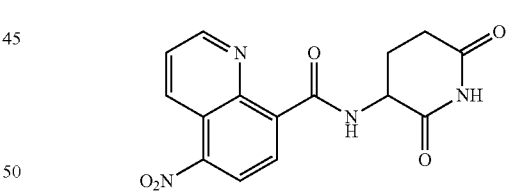

N-(2,6-dioxopiperidin-3-yl)-5-nitroquinoline-8-carboxamide (Int-15)

To a solution of compound Int-14 (540 mg, 2.47 mmol) and 3-aminopiperidine-2,6-dione hydrochloride (487 mg, 2.96 mmol) in DMF (5 mL) was added DIEA (957 mg, 7.41 mmol) and the mixture was stirred at 0° C. for 30 minutes. Then HOBt (400 mg, 2.96 mmol) and EDCI (567 mg, 2.96 mmol) were added slowly to the reaction mixture. The reaction was allowed to warm to room temperature and was stirred for 2 h. TLC showed that the reaction reached completion. The reaction mixture was partitioned between ethyl acetate and water. The combined organic layers were washed with water and brine, dried over $Na_2SO_4$ and con- 8-Methyl-5-nitroquinoline (Int-13)

A solution of 8-methylquinoline (5.0 g, 34.92 mmol) in conc. $H_2SO_4$ (18 mL) was stirred at 0° C. for about 30 minutes. Then $KNO_3$ (4.4 g, 43.65 mmol) was added slowly centrated under reduced pressure to give compound Int-15 (300 mg, 37.0%) as a gray solid.

¹H NMR (400 MHz, CDCl₃): δ 2.15-2.30 (m, 2H), 2.56-2.61 (m, 2H), 2.80-2.89 (m, 2H), 2.90-2.96 (m, 1H), 4.88-4.96 (m, 1H), 7.92 (q, J=4.0 Hz, 1H), 8.52 (dd, J=8.0 Hz, 1H), 8.58 (d, J=8.4 Hz, 1H), 8.92 (dd, J=1.6, 8.8 Hz, 1H), 9.174 (dd, J=1.6, 8.0 Hz, 1H), 10.93-10.96 (m, 1H).

ESI-MS (EI⁺, m/z): 329.10.

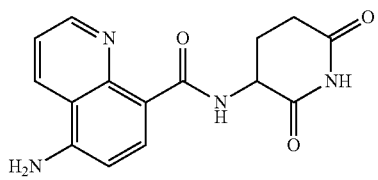

5-Amino-N-(2,6-dioxopiperidin-3-yl) quinoline-8-carboxamide (23)

To a solution of compound Int-15 (300 mg, 0.914 mmol) in MeOH (3 mL) was added 10% Pd/C (200 mg). The reaction mixture was stirred at room temperature overnight under hydrogen atmosphere. TLC showed that the reaction reached completion. The reaction mixture was filtered through diatomite and the filtrate was concentrated under reduced pressure to give the crude product (200 mg). The crude product was purified by prep-HPLC to afford compound 23 (30 mg, 11%) as an orange solid.

¹H NMR (400 MHz, DMSO-d₆): δ 2.10-2.20 (m, 2H), 2.58-2.61 (m, 2H), 2.76-2.85 (m, 1H), 4.79-4.86 (m, 1H), 6.83 (d, J=6.0 Hz, 1H), 7.65 (br, 1H), 8.39 (d, J=6.0 Hz, 2H), 9.00 (br, 2H), 10.90 (s, 1H).

ESI-MS (EI⁺, m/z): 299.15.

Example 16: Synthesis of 4-Amino-N-(2,6-dioxopiperidin-3-yl)quinoline-8-carboxamide (24)

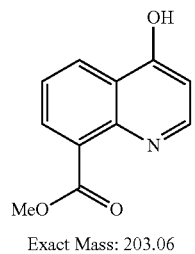

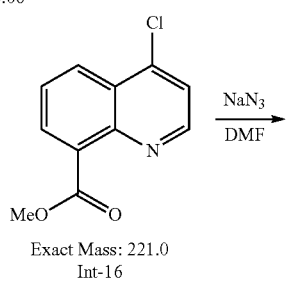

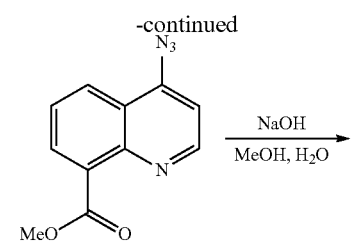

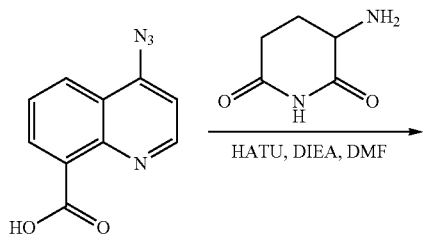

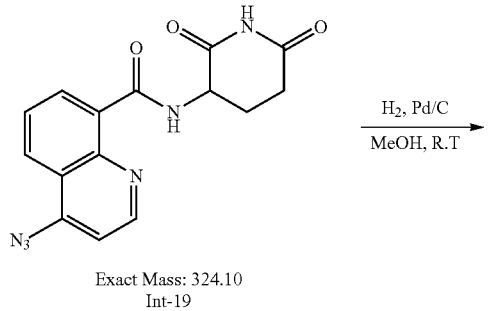

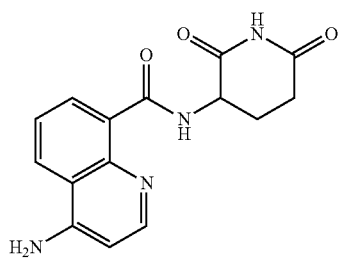

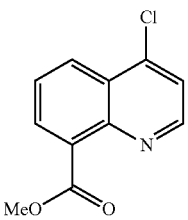 [SMILES: COC(=O)c1cccc2c(Cl)ccnc12]

Methyl 4-chloroquinoline-8-carboxylate (Int-16)

A solution of methyl 4-hydroxyquinoline-8-carboxylate (800 mg, 3.9 mmol) and POCl₃ (906 mg, 5.9 mmol) in dichloroethane (10 mL) was stirred at 90° C. for 3 h. TLC showed that the reaction reached completion. The solvent was evaporated under reduced pressure and the residue was purified by silica gel column chromatography (petroleum ether/ethyl acetate:2/1) to afford compound Int-16 (760 mg, 88%) as a yellow solid.

ESI-MS (EI⁺, m/z): 222.05.

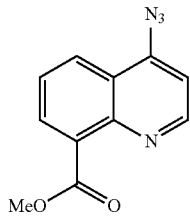 [SMILES: COC(=O)c1cccc2c(N=[N+]=[N-])ccnc12]

Methyl 4-azidoquinoline-8-carboxylate (Int-17)

A solution of compound I-16 (630 mg, 2.85 mmol), NaN$_3$ (241 mg, 3.70 mmol) in DMF (5 mL) was stirred at 80° C. overnight. The mixture was diluted with water and extracted with ethyl acetate. The combined organic layers were washed with water and brine, dried over Na$_2$SO$_4$ and concentrated under reduced pressure to afford compound Int-17 (600 mg, 92%) as a yellow solid.

ESI-MS (EI⁺, m/z): 229.10.

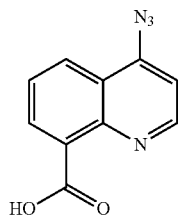 [SMILES: [N-]=[N+]=Nc1ccnc2c(C(=O)O)cccc12]

4-Azidoquinoline-8-carboxylic acid (Int-18)

A solution of compound Int-17 (300 mg, 1.3 mmol) and NaOH (105 mg, 2.6 mmol) in a mixture of THF (3 mL), MeOH (1 mL) and H$_2$O (1 mL) was stirred at room temperature for 6 h. The mixture was concentrated under reduced pressure and the residue was diluted with water (4 mL). The pH of the mixture was adjusted to 3-4 and the resulting suspension was filtered. The solid was dried to afford compound Int-18 (250 mg, 89%) as a white solid.

ESI-MS (EI⁺, m/z): 215.05.

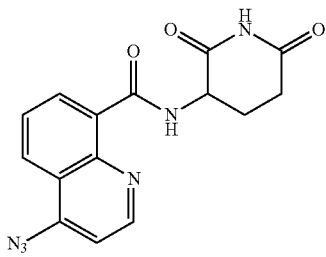 [SMILES: [N-]=[N+]=Nc1ccnc2c(C(=O)NC3CCC(=O)NC3=O)cccc12]

4-Azido-N-(2,6-dioxopiperidin-3-yl)quinoline-8-carboxamide (I-19)

HATU (646 mg, 1.7 mmol) was added slowly to a solution of compound Int-18 (250 mg, 1.2 mmol), 3-aminopiperdine-2,6-dione (275 mg, 1.7 mmol) and DIEA (61 mg, 2.8 mmol) in DMF (5 mL) at 0° C. in portions. The reaction was stirred at room temperature for 10 h. Water was added and the aqueous layer was extracted with EtOAc (2×50 mL). The combined organic layers were washed with H$_2$O and brine, and dried over Na$_2$SO$_4$. The solvent was removed under reduced pressure and the residue was purified by column chromatography (dichloromethane/methanol:30/1) to afford compound I-19 (300 mg) as a yellow solid.

ESI-MS (EI⁺, m/z): 325.10.

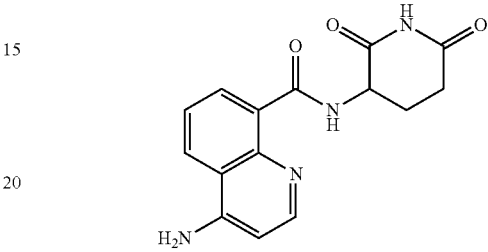

4-Amino-N-(2,6-dioxopiperidin-3-yl)quinoline-8-carboxamide (24)

To a solution of the compound I-19 (300 mg, 1.2 mmol) in MeOH (7 mL) was added with 10% Pd/C (60 mg). The reaction mixture was stirred at room temperature for 12 h under hydrogen atmosphere. TLC showed that the reaction reached completion. The reaction mixture was filtered through diatomite and the filtrate was concentrated under reduced pressure to give the crude product (200 mg). The crude product was purified by prep-HPLC to afford the product (24) (25 mg, 7% for 2 steps) as yellow solid.

$^1$H NMR (400 MHz, DMSO-d$_6$) δ 13.490 (s, 1H), 10.99 (s, 1H), 9.49 (d, J=8.0 Hz, 1H), 9.14 (d, J=26.8 Hz, 2H), 8.64 (d, J=8.4 Hz, 1H), 8.43 (d, J=6.4 Hz, 2H), 7.83 (t, J=7.6 Hz, 1H), 6.87 (d, J=6.8 Hz, 1H), 4.83-4.90 (m, 1H), 2.80-2.89 (m, 1H), 2.58-2.63 (m, 1H), 2.161-2.27 (m, 1H), 2.04-2.07 (m, 1H).

ESI-MS (EI⁺, m/z): 299.10.

Example 17: Synthesis of 3-Amino-N-(2,6-dioxopiperidin-3-yl)quinoline-8-carboxamide (25)

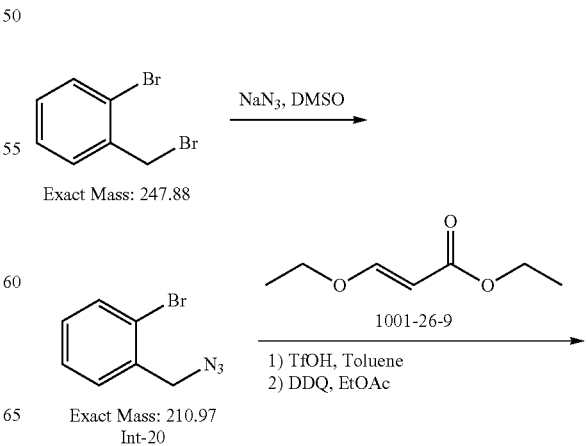

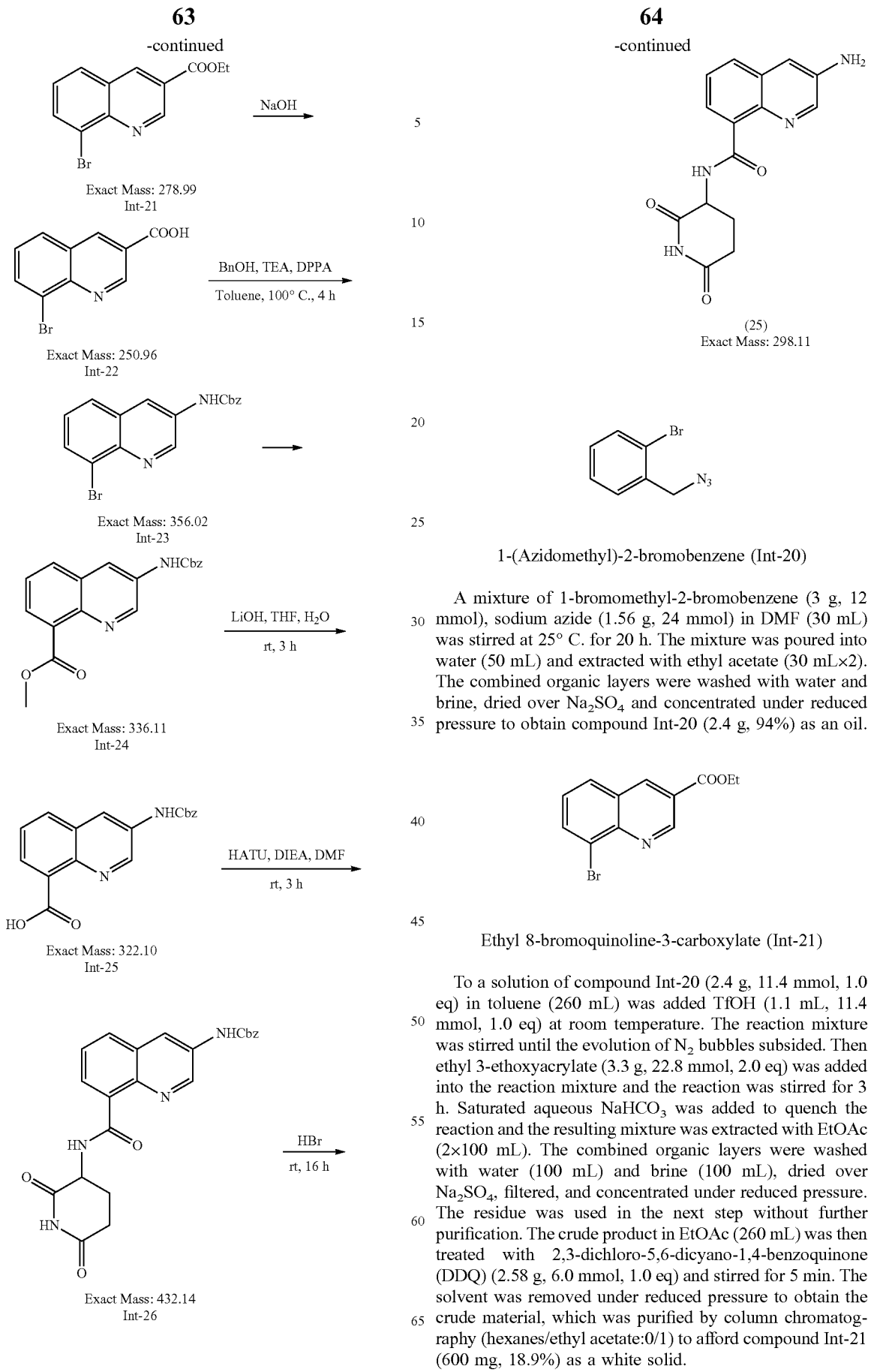

1-(Azidomethyl)-2-bromobenzene (Int-20)

A mixture of 1-bromomethyl-2-bromobenzene (3 g, 12 mmol), sodium azide (1.56 g, 24 mmol) in DMF (30 mL) was stirred at 25° C. for 20 h. The mixture was poured into water (50 mL) and extracted with ethyl acetate (30 mL×2). The combined organic layers were washed with water and brine, dried over $Na_2SO_4$ and concentrated under reduced pressure to obtain compound Int-20 (2.4 g, 94%) as an oil.

Ethyl 8-bromoquinoline-3-carboxylate (Int-21)

To a solution of compound Int-20 (2.4 g, 11.4 mmol, 1.0 eq) in toluene (260 mL) was added TfOH (1.1 mL, 11.4 mmol, 1.0 eq) at room temperature. The reaction mixture was stirred until the evolution of $N_2$ bubbles subsided. Then ethyl 3-ethoxyacrylate (3.3 g, 22.8 mmol, 2.0 eq) was added into the reaction mixture and the reaction was stirred for 3 h. Saturated aqueous $NaHCO_3$ was added to quench the reaction and the resulting mixture was extracted with EtOAc (2×100 mL). The combined organic layers were washed with water (100 mL) and brine (100 mL), dried over $Na_2SO_4$, filtered, and concentrated under reduced pressure. The residue was used in the next step without further purification. The crude product in EtOAc (260 mL) was then treated with 2,3-dichloro-5,6-dicyano-1,4-benzoquinone (DDQ) (2.58 g, 6.0 mmol, 1.0 eq) and stirred for 5 min. The solvent was removed under reduced pressure to obtain the crude material, which was purified by column chromatography (hexanes/ethyl acetate:0/1) to afford compound Int-21 (600 mg, 18.9%) as a white solid.

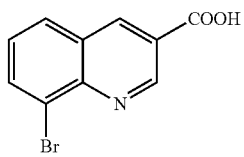 [SMILES: O=C(O)c1cnc2c(Br)cccc2c1]

8-bromoquinoline-3-carboxylic acid (Int-22)

Aqueous NaOH (2 N, 2 mL) was added to a mixture of compound Int-21 (558 mg, 2.0 mmol) in MeOH (4 mL) and the resulting mixture was stirred at room temperature for 2 h. The mixture was concentrated under reduced pressure and the residue was diluted with water (4 mL). The pH of the mixture was adjusted to 2 and the resulting suspension was filtered. The obtained solid was dried to afford the compound Int-22 (300 mg, 60%) as a yellow solid.

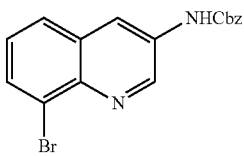 [SMILES: O=C(Nc1cnc2c(Br)cccc2c1)OCc1ccccc1]

Benzyl (8-bromoquinolin-3-yl)carbamate (Int-23)

A solution of compound Int-22 (168 mg, 0.66 mmol), BnOH (108 mg, 1.0 mmol), diphenylphosphoryl azide (DPPA) (275 mg, 1.0 mmol), and triethylamine (TEA) (101 mg, 1.0 mmol) in toluene (5 mL) was stirred at 100° C. for 4 h under $N_2$ atmosphere. The solvent was evaporated under reduced pressure. The residue was extracted with water and EtOAc (2×10 mL). The combined organic layers were washed with water (10 mL) and brine (10 mL), dried over $Na_2SO_4$, and filtered. The filtrate was concentrated under reduced pressure to afford the compound Int-23 (200 mg) as a yellow solid.

ESI-MS (EI$^+$, m/z): 357.0, 359.0.

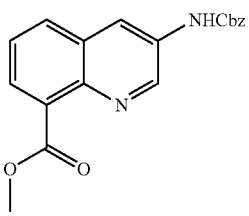 [SMILES: COC(=O)c1cccc2cc(NC(=O)OCc3ccccc3)cnc12]

Methyl 3-(((benzyloxy)carbonyl)amino)quinoline-8-carboxylate (Int-24)

A solution of compound Int-23 (410 mg, 1.15 mmol), Pd(dppf)Cl$_2$ (84 mg, 0.12 mmol), and TEA (232 mg, 2.3 mmol) in MeOH (10 mL) was stirred at 60° C. for 16 h under CO atmosphere.

The solution was filtered, the filtrate was concentrated in vacuo and the residue was purified by column chromatography (dichloromethane/MeOH:10/1) to afford compound Int-24 (223 mg, 57% for two steps) as a solid.

$^1$H NMR (400 MHz, DMSO-d$_6$): δ 10.39 (s, 1H), 8.90 (d, J=2.4 Hz, 1H), 8.55 (s, 1H), 8.07 (d, J=8.4 Hz, 1H), 7.78 (d, J=6.8 Hz, 1H), 7.60 (t, J=7.6 Hz, 1H), 7.47 (d, J=7.4 Hz, 2H), 7.40 (dt, J=7.2, 14.8 Hz, 3H), 7.30-7.32 (m, 2H), 5.23 (s, 2H), 3.90 (s, 3H).

ESI-MS (EI$^+$, m/z): 337.15.

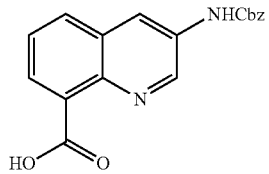 [SMILES: O=C(Nc1cnc2c(C(=O)O)cccc2c1)OCc1ccccc1]

3-(((Benzyloxy)carbonyl)amino)quinoline-8-carboxylic acid (Int-25)

To a mixture of compound Int-24 (223 mg, 0.66 mmol) in THF (2 mL) and H$_2$O (2 mL) was added LiOH H$_2$O (56 mg, 1.32 mmol, 2.0 eq) and the mixture was stirred at room temperature for 4 h. The mixture was concentrated in vacuo and the pH was adjusted to 4 with aqueous HCl (1 M). The resulting suspension was filtered and the obtained solid was dried to afford compound Int-25 (200 mg, 93.5%) as a white solid.

ESI-MS (EI$^+$, m/z): 323.10.

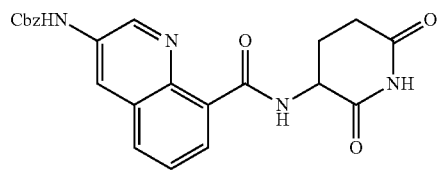 [SMILES: O=C1CCC(NC(=O)c2cccc3cc(NC(=O)OCc4ccccc4)cnc23)C(=O)N1]

Benzyl (8-((2,6-dioxopiperidin-3-yl)carbamoyl)quinolin-3-yl)carbamate (Int-26)

HATU (258 mg, 0.68 mmol, 1.0 eq) was added to a mixture of compound Int-25 (220 mg, 0.68 mmol, 1.0 eq), 3-aminopiperidine-2,6-dione hydrochloride (110 mg, 0.68 mmol, 1.0 eq) and DIEA (175 mg, 1.36 mmol, 2.0 eq) in DMF (5 mL) at 0-5° C. The resulting mixture was allowed to warm to room temperature for 3 h. Water was added to the reaction mixture and the resulting suspension was filtered. The filtrate cake was washed with H$_2$O and was dried to afford compound Int-26 (202 mg, 70.6%) as an off-white solid.

$^1$H NMR (400 MHz, DMSO-d$_6$): δ 11.29 (d, J=7.6 Hz, 1H), 10.93 (s, 1H), 10.48 (s, 1H), 9.00 (d, J=2.8 Hz, 1H), 8.67 (d, J=2.8 Hz, 1H), 8.45 (dd, J=1.2, 7.2 Hz, 1H), 8.16 (dd, J=1.6, 8.4 Hz, 1H), 7.71 (t, J=8.0 Hz, 1H), 7.49 (dd, J=8.1, 1.5 Hz, 2H), 7.40-7.47 (m, 2H), 7.32-7.39 (m, 1H), 5.25 (s, 2H), 4.87-4.93 (m, 1H), 2.77-2.87 (m, 1H), 2.53-2.60 (m, 1H), 2.22-2.30 (m, 1H), 2.09-2.28 (m, 1H).

ESI-MS (EI$^+$, m/z): 433.20.

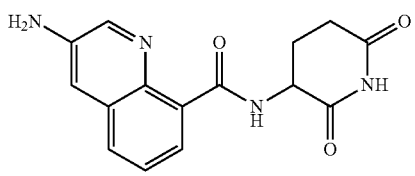 [SMILES: Nc1cnc2c(C(=O)NC3CCC(=O)NC3=O)cccc2c1]

3-Amino-N-(2,6-dioxopiperidin-3-yl)quinoline-8-carboxamide (25)

A solution of compound Int-26 (60 mg, 0.14 mmol) in HBr (3 mL) was stirred at room temperature for 16 hours. TLC showed that the reaction reached completion. The reaction mixture was added a solution of aqueous NaHCO$_3$ to adjust the pH to 9. The mixture was then extracted with EtOAc (2×10 mL), and the combined organic layers were washed with water (10 mL) and brine (10 mL), dried over Na$_2$SO$_4$ and concentrated in vacuo. The residue was purified by prep-TLC (dichloromethane/MeOH:15/1) to afford the product (25) (30 mg, 72.6%) as an off-white solid.

$^1$H NMR (400 MHz, DMSO-d$_6$): δ 11.51 (d, J=6.8 Hz, 1H), 10.93 (s, 1H), 8.54 (d, J=2.4 Hz, 1H), 8.20 (d, J=7.2 Hz, 1H), 7.85 (d, J=8.4 Hz, 1H), 7.52 (t, J=7.6 Hz, 1H), 7.32 (d, J=2.4 Hz, 1H), 5.90 (s, 2H), 4.83-4.89 (m, 1H), 2.77-2.86 (m, 1H), 2.53-2.58 (m, 1H), 2.22-2.31 (m, 1H), 2.14-2.19 (m, 1H).

ESI-MS (EI$^+$, m/z): 299.15.

Example 18: Synthesis of N-(2,6-dioxopiperidin-3-yl)-4-hydroxyquinoline-8-carboxamide (26)

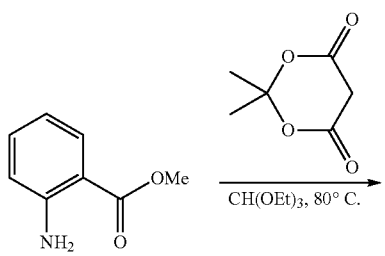

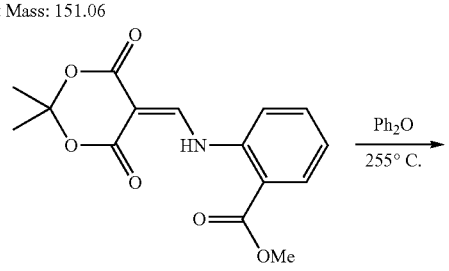

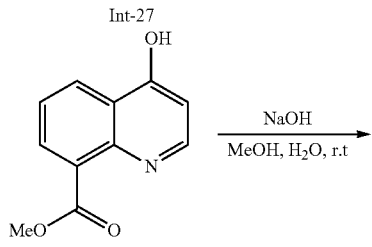

Exact Mass: 203.06
Int-28

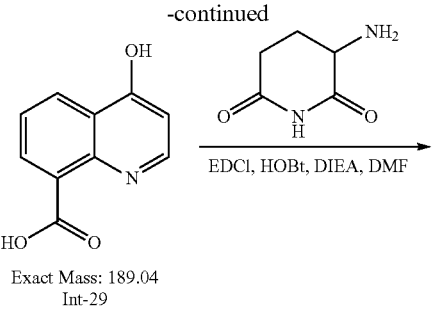

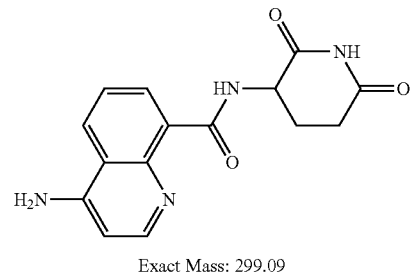

Exact Mass: 299.09

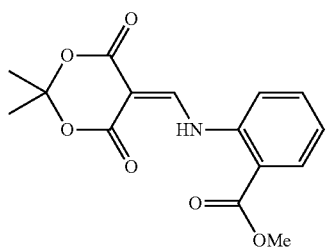 [SMILES: COC(=O)c1ccccc1NC=C1C(=O)OC(C)(C)OC1=O]

Methyl 2-(((2,2-dimethyl-4,6-dioxo-1,3-dioxan-5-ylidene)methyl)amino)benzoate (Int-27)

A solution of methyl 2-aminobenzoate (3.0 g, 20.83 mmol) and 2,2-dimethyl-1,3-dioxane-4,6-dione (6.3 g, 41.67 mmol) in triethyl orthoformate (18.5 g, 124.98 mmol) was stirred at 80° C. for about 4 h. TLC showed that the reaction reached completion. The reaction mixture was cooled down to room temperature and filtered through diatomite. The recovered solid was washed with diethyl ether and dried to give compound Int-27 (5.8 g, 91%).

$^1$H NMR (400 MHz, CDCl$_3$): δ 1.75 (s, 6H), 4.03 (s, 3H), 7.27-7.31 (m, 1H), 7.52 (d, J=8.4 Hz, 1H), 7.61-7.66 (m, 1H), 8.13 (dd, J=1.2, 8.0 Hz, 1H), 8.75 (d, J=14.0 Hz, 1H), 13.18 (d, J=14.0 Hz, 1H).

ESI-MS (EI$^-$, m/z): 304.10.

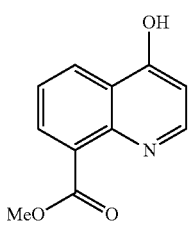 [SMILES: COC(=O)c1cccc2c(O)ccnc12]

Methyl 4-hydroxyquinoline-8-carboxylate (Int-28)

A solution of the compound Int-27 (3.0 g, 9.83 mmol) in Ph₂O (30 mL) was stirred at 255° C. under nitrogen atmosphere for 1.5 h. TLC showed that the reaction reached completion. The reaction mixture was cooled to room temperature and purified by column chromatography (dichloromethane/methanol:30/1) to give compound Int-28 (1.90 g, 95%).

¹H NMR (400 MHz, CDCl₃): δ 3.99 (s, 3H), 6.34 (d, J=7.6 Hz, 1H), 7.35 (t, J=8.0 Hz, 1H), 7.68 (t, J=6.8 Hz, 1H), 8.37 (d, J=7.6 Hz, 1H), 8.63 (d, J=8.0 Hz, 1H), 11.69 (s, 1H).
ESI-MS (EI⁺, m/z): 204.10.

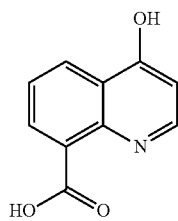 [SMILES: O=C(O)c1cccc2c(O)ccnc12]

4-Hydroxyquinoline-8-carboxylic acid (Int-29)

A solution of compound Int-28 (508 mg, 2.50 mmol) in MeOH (6 mL) was stirred at room temperature for about 30 minutes. Aqueous NaOH (2 N, 3 mL) was added to the reaction mixture. The reaction was allowed to warm to room temperature and was stirred for 3 hours. TLC showed that the reaction reached completion. The reaction mixture was concentrated under reduced pressure and the residue was acidified to pH 3 with aqueous HCl (1 N). The resulting suspension was filtered and the isolated solid was washed with water. The filter cake was dried to give compound Int-29 (390 mg, 82.5%) as a gray solid.

ESI-MS (EI⁻, m/z): 188.15.

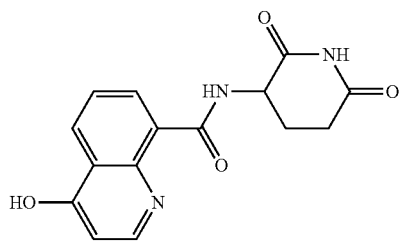 [SMILES: O=C1CCC(NC(=O)c2cccc3c(O)ccnc23)C(=O)N1]

N-(2,6-dioxopiperidin-3-yl)-4-hydroxyquinoline-8-carboxamide (26)

To a mixture of compound Int-29 (200 mg, 1.06 mmol) and 3-aminopiperidine-2,6-dione hydrochloride (209 mg, 1.27 mmol) in 3 mL of DMF was added DIEA (411 mg, 3.18 mmol). The reaction mixture was stirred at 0° C. for 30 minutes. HOBt (172 mg, 1.27 mmol) and EDCI (243 mg, 1.27 mmol) were added slowly into the reaction mixture before allowing the reaction to warm to room temperature. The mixture was then stirred for 3 h. TLC showed that the reaction reached completion. The reaction mixture was diluted with water and extracted with EtOAc (2×30 mL). The combined organic layers were washed with water and brine, dried over Na₂SO₄ and concentrated under reduced pressure. The residue was purified by prep-HPLC to give compound (26) (20 mg) as an orange solid.

¹H NMR (400 MHz, DMSOd₆): δ 2.02-2.09 (m, 1H), 2.15-2.26 (m, 1H), 2.57-2.61 (m, 1H), 2.79-2.88 (m, 1H), 4.81-4.87 (m, 1H), 6.20 (d, J=7.6 Hz, 1H), 7.47 (t, J=8.0 Hz, 1H), 8.04 (d, J=7.2 Hz, 1H), 8.19 (d, J=6.8 Hz, 1H), 8.34 (dd, J=1.2, 8.0 Hz, 1H), 9.27 (s, 1H), 10.96 (s, 1H), 12.20 (s, 1H).
ESI-MS (EI⁺, m/z): 300.10.

Example 19: Synthesis of 1-(5-aminopyridin-2-yl)-3-(2,6-dioxopiperidin-3-yl)urea (27)

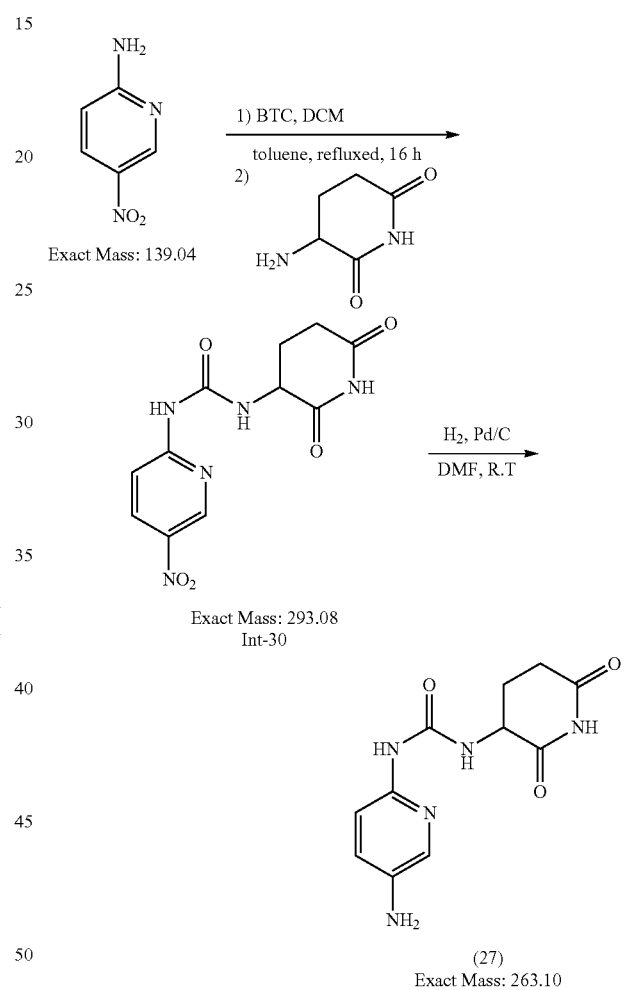

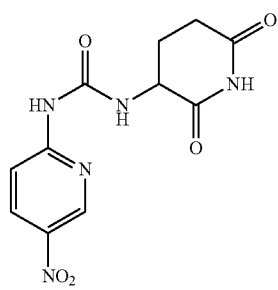 [SMILES: O=C1CCC(NC(=O)Nc2ccc([N+](=O)[O-])cn2)C(=O)N1]

1-(2,6-Dioxopiperidin-3-yl)-3-(5-nitropyridin-2-yl)urea (Int-30)

To a stirring solution of triphosgene (2.1 g, 7.1 mmol, 1.0 eq) in dichloromethane (25 mL) at 0° C. was added 5-nitropyridin-2-amine (2 g, 14.3 mmol, 2.0 eq) and Et₃N (2 mL, 14.3 mmol, 2.0 eq). The mixture was stirred at room temperature for 6 h. TLC showed that the reaction reached completion. The reaction mixture was concentrated in vacuo, and the residue was used in the next step without further purification. The crude product was dissolved in a toluene (15 mL) and 3-aminopiperidine-2,6-dione hydrochloride (1.16 g, 7.1 mmol, 1.0 eq) before adding Et₃N (3 ml, 21.3 mmol, 3 eq). The resulting mixture was stirred at 110° C. for 16 h under N₂ atmosphere. The solvent was removed under reduced pressure and the residue was washed with water and brine, and triturated with EtOAc. The resulting suspension was filtered and the solid was dried to afford the compound Int-30 (1.8 g, 42%) as a black solid.

ESI-MS (EI⁺, m/z): 294.15.

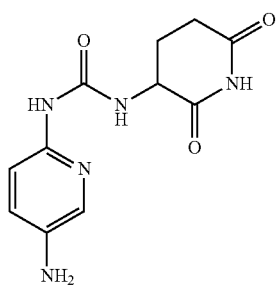 [SMILES: Nc1ccc(NC(=O)NC2CCC(=O)NC2=O)nc1]

1-(5-aminopyridin-2-yl)-3-(2,6-dioxopiperidin-3-yl)urea (27)

A solution of compound Int-30 (100 mg, 0.34 mmol) in MeOH (5 mL) was treated with 10% Pd/C (15 mg). The mixture was stirred at room temperature for 16 h under hydrogen atmosphere. LC-MS was used to confirm that the reaction was completed. The reaction mixture was filtered through diatomite and the filtrate was concentrated under reduced pressure. The obtained residue was purified by prep-HPLC to afford the product (27) (23 mg, 26%).

¹H NMR (400 MHz, D₂O): δ 7.28-7.86 (m, 2H), 7.26-7.32 (m, 1H), 4.73 (dd, J=6.0, 12.4 Hz, 1H), 2.83-2.90 (m, 2H), 2.23-2.32 (m, 2H).

ESI-MS (EI⁺, m/z): 264.15.

Example 20: Synthesis of 1-(2,6-dioxopiperidin-3-yl)-3-(5-hydroxypyridin-2-yl)urea (28)

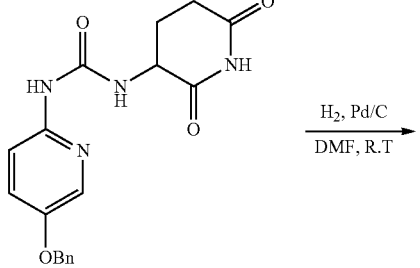

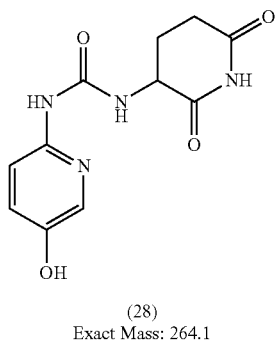

1-(5-(Benzyloxy)pyridin-2-yl)-3-(2,6-dioxopiperidin-3-yl)urea (Int-31)

To a stirring solution of triphosgene (296 mg, 1.0 mmol, 1.0 eq) in dichloromethane (4 mL) at 0° C. was added 5-(benzyloxy)pyridin-2-amine (400 mg, 2.0 mmol, 2.0 eq) and Et₃N (202 mg, 2.0 mmol, 2.0 eq). The mixture was stirred at room temperature for 2 hours. TLC showed that the reaction reached completion. The reaction mixture was concentrated in vacuo, and the residue was used in the next step without further purification. The crude product, dissolved in toluene (15 mL), was added to a mixture of 3-aminopiperidine-2,6-dione hydrochloride (328 mg, 2.0 mmol, 1.0 eq) and Et₃N (606 mg, 6.0 mmol, 3.0 eq). The resulting mixture was stirred at 120° C. for 16 hours under N₂ atmosphere. The solvent was evaporated under reduced pressure and the residue was washed with water and brine, and triturated with EtOAc. The observed suspension was filtered and the obtained solid was dried to afford compound Int-31 (370 mg, 70.6%) as a white solid.

¹H NMR (400 MHz, DMSO-d₆): δ 10.84 (s, 1H), 9.20 (s, 1H), 8.21 (br, 1H), 7.96 (d, J=2.8 Hz, 1H), 7.30-7.49 (m, 7H), 5.12 (s, 2H), 4.47-4.58 (m, 1H), 2.69-2.78 (m, 1H), 2.51-2.54 (m, 1H), 2.09-2.13 (m, 1H), 1.90-2.03 (m, 1H).

ESI-MS (EI⁺, m/z): 355.20.

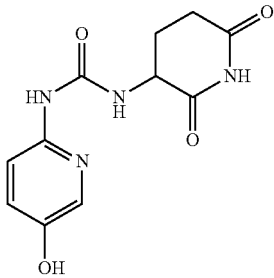 [SMILES: O=C1CCC(NC(=O)Nc2ccc(O)cn2)C(=O)N1]

1-(2,6-Dioxopiperidin-3-yl)-3-(5-hydroxypyridin-2-yl)urea (28)

A solution of compound Int-31 (200 mg, 0.56 mmol) in DMF (10 mL) was treated with 10% Pd/C (20 mg). The mixture was stirred at room temperature for 16 h under hydrogen atmosphere. LC-MS was used to confirm that the reaction was completed. The reaction mixture was filtered through diatomite and the filtrate was concentrated under reduced pressure. The residue was purified by prep-HPLC to afford compound 28 (70 mg, 46.9%).

$^1$H NMR (400 MHz, DMSO-d$_6$): δ 10.83 (s, 1H), 9.42 (s, 1H), 9.06 (s, 1H), 8.30 (br, 1H), 7.74 (d, J=2.8 Hz, 1H), 7.24 (d, J=8.8 Hz, 1H), 7.16 (dd, J=2.8, 8.8 Hz, 1H), 4.48-4.56 (m, 1H), 2.68-2.78 (m, 1H), 2.51-2.54 (m, 1H), 2.07-2.15 (m, 1H), 1.92-2.03 (m 1H).

ESI-MS (EI$^+$, m/z): 265.12.

Example 21: Synthesis of 1-(2,6-Dioxopiperidin-3-yl)-3-(indolin-7-yl)urea (29)

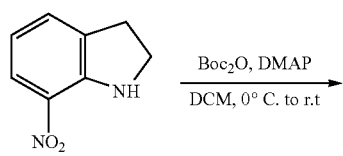

Exact Mass: 162.0

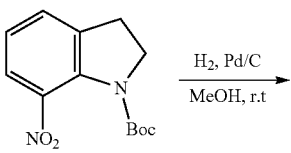

Exact Mass: 262.1
Int-32

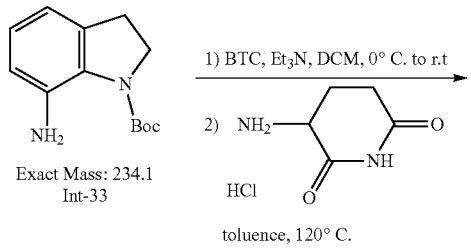

Exact Mass: 234.1
Int-33

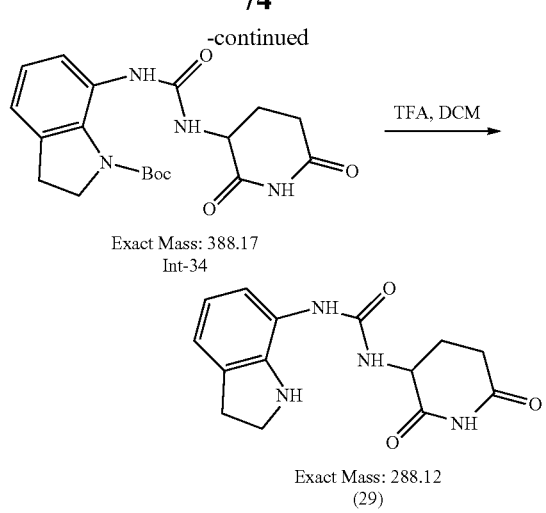

Exact Mass: 388.17
Int-34

Exact Mass: 288.12
(29)

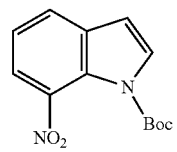 [SMILES: CC(C)(C)OC(=O)n1ccc2cccc([N+](=O)[O-])c21]

tert-Butyl 7-nitro-1H-indole-1-carboxylate (Int-32)

To a solution of tert-butyl 7-nitro-1H-indole-1-carboxylate (5 g, 30.8 mmol) in DCM (40 mL) at 0° C. was added 4-dimethylaminopyridine (DMAP) (76 mg, 0.62 mmol) and Boc$_2$O (7.4 g, 33.9 mmol) portion-wise. The reaction mixture was stirred at room temperature for 3.5 h. TLC showed that the reaction reached completion. The solvent was removed under reduced pressure and the residue was purified by column chromatography (petroleum ether/ethyl acetate:10/1) to afford compound Int-32 (7.6 g, 94%) as a yellow solid.

$^1$H NMR (400 MHz, DMSO-d$_6$): δ 1.54 (s, 9H), 6.94 (d, J=3.6 Hz, 1H), 7.44 (t, J=7.6 Hz, 1H), 7.83-7.87 (m, 2H), 8.02 (d, J=7.6 Hz, 1H).

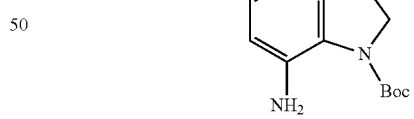

tert-Butyl 7-aminoindoline-1-carboxylate (Int-33)

A mixture of compound Int-32 (2.62 g, 10 mmol) in MeOH (15 mL) was treated with 10% Pd/C (450 mg). The mixture was stirred at room temperature for 20 h under hydrogen atmosphere. TLC was used to confirm that the reaction was completed. The reaction mixture was filtered through diatomite and the filtrate was concentrated under reduced pressure. The filtrate was concentrated under reduced pressure to give the product (Int-33) (2 g, 85%).

ESI-MS (EI$^+$, m/z): 235.151.

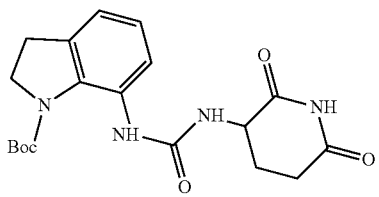 [SMILES: CC(C)(C)OC(=O)N1CCc2cccc(NC(=O)NC3CCC(=O)NC3=O)c21]

tert-Butyl 7-(3-(2,6-dioxopiperidin-3-yl)ureido)indoline-1-carboxylate (Int-34)

To a solution of triphosgene (698 mg, 2.35 mmol) in DCM (8 mL) at 0° C. was added compound Int-33 (1.1 g, 4.7 mmol) and Et$_3$N (0.7 mL, 4.7 mmol) portion-wise. The reaction mixture was allowed to warm to room temperature and was stirred for 4 h. The solvent was removed under reduced pressure. A mixture of 3-aminopiperidine-2,6-dione hydrochloride (774 mg, 4.7 mmol) and Et$_3$N (2 mL, 14.1 mmol, 3.0 eq) in toluene (10 mL) was added and the resulting mixture was heated to 120° C. overnight. The solvent was removed under reduced pressure and the residue was diluted with EtOAc (25 mL) and water (25 mL). The mixture was stirred for 2 h and then was filtered. The isolated solid was dried to afford the compound Int-34 (1.5 g, 82%) as a gray solid.

ESI-MS (EI$^+$, m/z): 389.15.

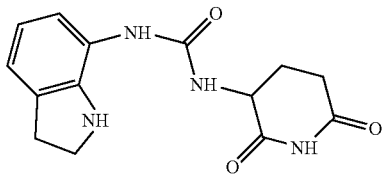 [SMILES: O=C1CCC(NC(=O)Nc2cccc3c2NCC3)C(=O)N1]

1-(2,6-Dioxopiperidin-3-yl)-3-(indolin-7-yl)urea (29)

To a solution compound Int-34 (300 mg, 0.77 mmol) in DCM (4 mL) was added trifluoroacetic acid (TFA) (2 mL). The mixture was stirred at room temperature for 1.5 h before removing the solvent under reduced pressure. The crude product (200 mg) was purified by prep-HPLC to afford compound 29 (60 mg, 27%) as a yellow solid.

$^1$H NMR (400 MHz, DMSO-d$_6$): δ 1.96-2.04 (m, 1H), 2.07-2.13 (1H), 2.53-2.55 (m, 1H), 2.69-2.78 (m, 1H), 3.14 (t, J=8.0 Hz, 2H), 3.63 (t, J=7.6 Hz, 2H), 4.43-4.50 (m, 1H), 7.07-7.14 (m, 3H), 7.18-7.22 (m, 1H), 9.07-9.18 (m, 1H), 10.90 (s, 1H).

ESI-MS (EI$^+$, m/z): 289.15.

Example 22: Synthesis of N-(2,6-dioxopiperidin-3-yl)indoline-7-carboxamide (30)

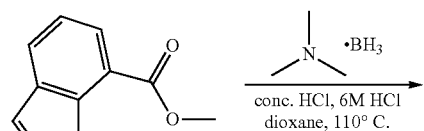

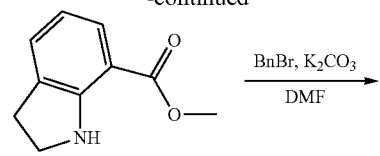

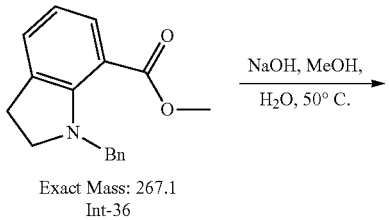

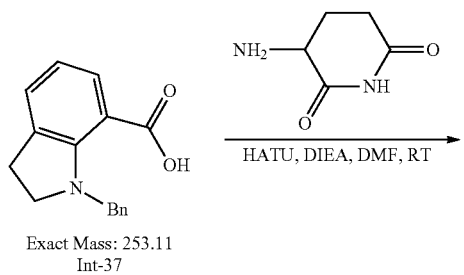

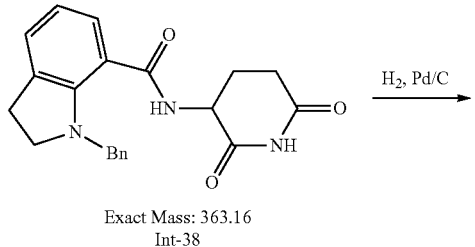

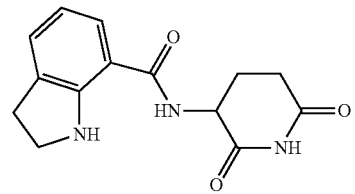

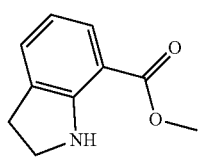

Methyl indoline-7-carboxylate (Int-35)

A solution of methyl 1H-indole-7-carboxylate (1.75 g, 10.0 mmol) and BH$_3$NMe$_3$ (2.92 g, 40 mmol) in 1,4-dioxane (10 mL) was treated with conc. HCl (2 mL). The reaction mixture was stirred at 110° C. for 0.5 h and then cooled to room temperature. HCl (10 mL, 6 M) was added, and the mixture was stirred at 110° C. for 15 min. LC-MS showed that the reaction reached completion. The reaction mixture was cooled to room temperature and the pH of the reaction mixture was adjusted to 8 with aqueous NaOH (4 M). The resulting mixture was extracted with EtOAc (3×50 mL), and the combined organic layers were dried over Na₂SO₄ and concentrated under reduced pressure. The crude product was purified by column chromatography (hexanes/ethyl acetate: 50/1) to afford compound Int-35 (1.35 g, 76%) as a white solid.

ESI-MS (EI⁺, m/z): 178.15.

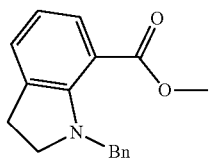 [SMILES: COC(=O)c1cccc2c1N(Cc1ccccc1)CC2]

Methyl 1-benzylindoline-7-carboxylate (Int-36)

A mixture of compound Int-35 (950 mg, 5.36 mmol) and (bromomethyl)benzene (1835 mg, 10.73 mmol) in DMF (12 mL) was treated with K₂CO₃ (1481 mg, 10.73 mmol) and the mixture was stirred at room temperature for 4 h. After addition of water, the mixture was extracted with ethyl acetate. The pooled organic layers were washed with water and brine, dried over Na₂SO₄ and concentrated under reduced pressure. The crude product was purified by column chromatography (hexanes/ethyl acetate:100/1) to afford compound Int-36 (1.24 g, 86.7%) as a colorless oil.

ESI-MS (EI⁺, m/z): 268.15.

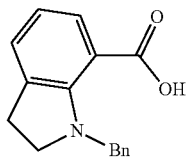 [SMILES: O=C(O)c1cccc2c1N(Cc1ccccc1)CC2]

1-Benzylindoline-7-carboxylic acid (Int-37)

Aqueous NaOH (2 M, 4 mL) was added to a solution of compound Int-36 (1.0 g, 3.74 mmol) in MeOH (15 mL) and the resulting mixture was stirred at room temperature overnight. The reaction mixture was concentrated and the residue was diluted with water (15 mL). The pH of the mixture was adjusted to 2 and the resulting mixture was extracted with ethyl acetate. The pooled organic layers were dried over Na₂SO₄ and concentrated under reduced pressure to afford compound Int-37 (700 mg, 74%) as a yellow solid.

ESI-MS (EI⁺, m/z): 254.15.

1-Benzyl-N-(2,6-dioxopiperidin-3-yl)indoline-7-carboxamide (Int-38)

HATU (1.26 g, 3.32 mmol, 1.2 eq) was added to a mixture of compound Int-37 (700 mg, 2.76 mmol, 1.0 eq), 3-aminopiperidine-2,6-dione hydrochloride (546 mg, 3.32 mmol, 1.2 eq) and DIEA (1070 mg, 8.30 mmol, 3.0 eq) in DMF (15 mL) at 0° C. The resulting mixture was allowed to warm to room temperature and was stirred for 3 h. Water was added and the aqueous layer was extracted with EtOAc (3×50 mL). The combined organic layers were washed with water and brine, dried over Na₂SO₄. The solvent was removed under reduced pressure and the residue was purified by column chromatography (dichloromethane/methanol:50/1) to afford compound Int-38 (730 mg, 73%) as a yellow solid.

ESI-MS (EI⁺, m/z): 364.15.

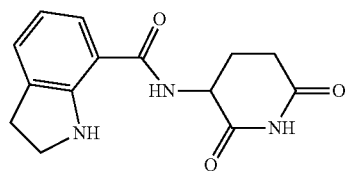 [SMILES: O=C1CCC(NC(=O)c2cccc3c2NCC3)C(=O)N1]

N-(2,6-dioxopiperidin-3-yl)indoline-7-carboxamide (30)

A solution of the compound Int-38 (600 mg, 1.65 mmol) in MeOH (15 mL) was treated with 10% Pd/C (70 mg) and the mixture was stirred at room temperature for 3 h under hydrogen atmosphere. TLC showed that the reaction reached completion. The reaction mixture was filtered through diatomite and the filtrate was concentrated under reduced pressure. The residue was triturated with a mixture of dichloromethane/methanol (V/V: 10/1, 22 mL) and was stirred at room temperature for 30 min. The mixture was filtered and the obtained solid was dried to afford the product (30) (280 mg, 62.0%) as a white solid.

¹H NMR (400 MHz, DMSO-d₆): δ 10.80 (s, 1H), 8.39 (d, J=8.4 Hz, 1H), 7.39 (d, J=8.0 Hz, 1H), 7.12 (d, J=6.8 Hz, 1H), 6.55 (s, 1H), 6.50 (t, J=7.6 Hz, 1H), 4.67-4.73 (m, 1H), 3.55 (t, J=8.4 Hz, 2H), 2.93 (t, J=8.4 Hz, 2H), 2.73-2.82 (m, 1H), 2.52-2.56 (m, 1H), 2.07-2.18 (m, 1H), 1.92-1.97 (m, 1H).

ESI-MS (EI⁺, m/z): 274.10.

Example 23: Synthesis of N-(2,6-dioxopiperidin-3-yl)-1H-benzo[d]imidazole-4-carboxamide (31)

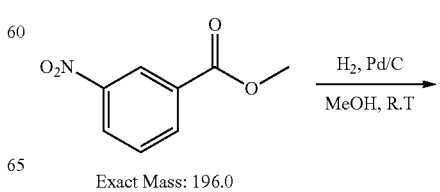

Exact Mass: 196.0

-continued

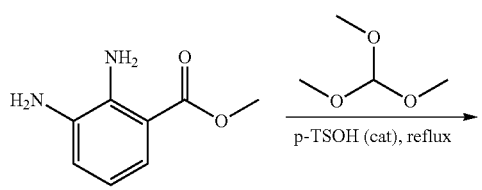

Exact Mass: 166.1
Int-39

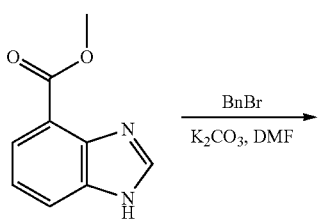

Exact Mass: 176.1
Int-40

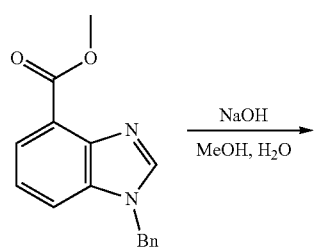

Exact Mass: 266.11
Int-41

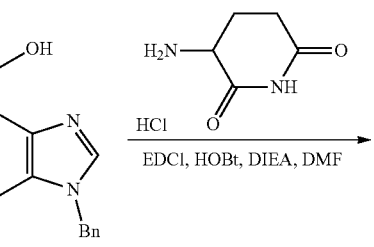

Exact Mass: 252.09
Int-42

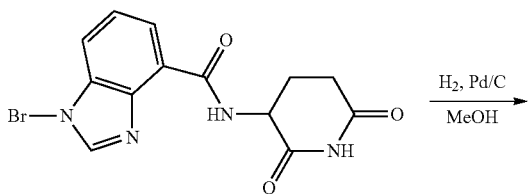

Exact Mass: 362.14
Int-43

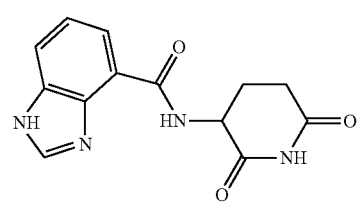

Exact Mass: 272.09
(31)

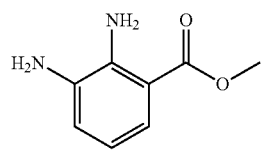

Methyl 2,3-diaminobenzoate (Int-39)

A solution of methyl 2-amino-3-nitrobenzoate (2 g, 10.2 mmol) in MeOH (15 mL) was treated with 10% Pd/C (200 mg) and the reaction mixture was stirred at room temperature for 3 h under hydrogen atmosphere. TLC showed the reaction reached completion. The reaction mixture was filtered through diatomite and the filtrate was concentrated under reduced pressure to give compound Int-39 (1.6 g, 94%) as a yellow solid, which used in next step without further purification.

ESI-MS (EI$^+$, m/z): 167.1.

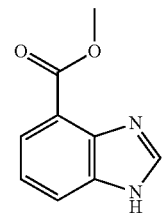

Methyl 1H-benzo[d]imidazole-4-carboxylate (Int-40)

A mixture of compound Int-39 (1.6 g, 9.64 mmol) in trimethyl orthoformate (24 mL) was treated with p-TsOH (91 g, 0.5 mmol, 0.05 eq) and the mixture was heated to reflux under N$_2$ for 2 h. The mixture was cooled to room temperature and filtered. The filtrate cake was washed with some Et$_2$O and dried to afford the compound Int-40 (1.3 g, 76.6%) as a yellow oil.

$^1$H NMR (400 MHz, CDCl$_3$): δ 3.94 (s, 3H), 2.45 (s, 3H), 7.32 (t, J=8 Hz, 2H) 7.85 (t, J=7.6 Hz, 2H), 7.96 (d, J=8.0 Hz, 2H), 8.32 (s, 1H), 12.58 (br, 1H).

ESI-MS (EI$^+$, m/z): 177.1.

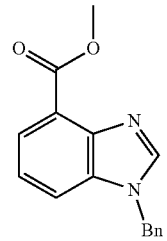 [SMILES: COC(=O)c1cccc2c1ncn2Cc1ccccc1]

Methyl 1-benzyl-1H-benzo[d]imidazole-4-carboxylate (Int-41)

A solution of BnBr (1.11 g, 6.6 mmol) in DMF (1.5 mL) was added dropwise to a solution of the compound Int-40 (880 mg, 5 mmol) in DMF (10 mL) at 0-5° C. The reaction was allowed to warm to room temperature and was stirred for 15 h. The mixture was partitioned between ethyl acetate and water. The organic phase was washed with water and brine, dried over Na$_2$SO$_4$ and concentrated under reduced pressure. The crude product was purified by column chromatography (hexanes/ethyl acetate:3/1) to afford the compound Int-41 (600 mg, 45%) as a yellow solid.

$^1$H NMR (400 MHz, CDCl$_3$): δ 3.74 (s, 3H), 5.75 (s, 2H), 6.93-6.95 (m, 2H), 7.20-7.24 (m, 3H), 7.28 (t, J=8.0 Hz, 1H), 7.71 (dd, J=0.8, 8.0 Hz, 1H), 8.00 (dd, J=0.8, 8.0 Hz, 1H), 8.07 (s, 1H).

ESI-MS (EI$^+$, m/z): 267.15.

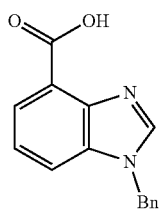 [SMILES: O=C(O)c1cccc2c1ncn2Cc1ccccc1]

1-Benzyl-1H-benzo[d]imidazole-4-carboxylic acid (Int-42)

Aqueous NaOH (2 N, 3 mL) was added to a mixture of the compound Int-41 (600 mg, 2.25 mmol) in MeOH (8 mL) and the resulting mixture was stirred at room temperature for 2 h. The mixture was concentrated under reduced pressure and the residue was diluted with water (4 mL). The pH of mixture was adjusted to 2 and the resulting suspension was filtered. The solid was dried to afford the compound Int-42 (320 mg, 53%) as a yellow solid.

$^1$H NMR (400 MHz, DMSO-d$_6$): δ 5.84 (s, 2H), 6.93-6.95 (m, 2H), 6/95-6.97 (m, 2H), 7.20-7.29 (m, 4H), 7.28 (t, J=8.0 Hz, 1H), 7.66 (dd, J=0.8, 7.6 Hz, 1H), 7.91 (dd, J=0.8, 8.0 Hz, 1H), 8.54 (s, 1H).

ESI-MS (EI$^+$, m/z): 253.1.

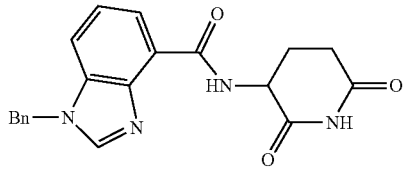 [SMILES: O=C1CCC(NC(=O)c2cccc3c2ncn3Cc2ccccc2)C(=O)N1]

1-Benzyl-N-(2,6-dioxopiperidin-3-yl)-1H-benzo[d]imidazole-4-carboxamide (Int-43)

EDCI (210 mg, 1.1 mmol, 1.2 eq) and HOBt (149 mg, 1.1 mmol, 1.2 eq) was added to a mixture of the compound Int-42 (230 mg, 0.91 mmol, 1.0 eq), 3-aminopiperidine-2,6-dione hydrochloride (181 mg, 1.1 mmol, 1.2 eq) and DIEA (353 mg, 2.73 mmol, 3.0 eq) in DMF (8 mL) at 0-5° C. The resulting mixture was allowed to warm to room temperature and was stirred for 2 h. Water was added and the aqueous layer was extracted with EtOAc (2×50 mL). The combined organic layers were washed with H$_2$O and brine, and dried over Na$_2$SO$_4$. The solvent was removed under reduced pressure and the residue was purified by column chromatography (dichloromethane/methanol: 30/1) to afford the compound Int-43 (310 mg) as a yellow powder.

$^1$H NMR (400 MHz, DMSO-d$_6$): δ 2.06-2.17 (m, 1H), 2.24-2.27 (m, 1H), 2.54-2.59 (m, 1H), 2.78-2.87 (m, 1H), 4.88-4.95 (m, 1H), 5.61 (s, 2H), 7.28-7.39 (m, 5H), 7.78 (d, J=8.4 Hz, 1H), 7.91 (d, J=7.6 Hz, 1H), 8.72 (s, 1H), 10.18 (d, J=7.2 Hz, 1H), 10.93 (s, 1H).

ESI-MS (EI$^+$, m/z): 363.15.

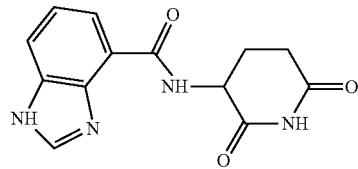 [SMILES: O=C1CCC(NC(=O)c2cccc3[nH]cnc23)C(=O)N1]

N-(2,6-dioxopiperidin-3-yl)-1H-benzo[d]imidazole-4-carboxamide (31)

A solution of compound Int-43 (310 mg, 0.82 mol) in MeOH (7 mL) was treated with 10% Pd/C (60 mg) and the reaction mixture was stirred at room temperature for 5 h under hydrogen atmosphere. TLC showed the reaction reached completion. The reaction mixture was filtered through diatomite and the filtrate was concentrated under reduced pressure to give the crude product (200 mg), which was purified by prep-HPLC to afford the product (31) (30 mg, 12% for 2 steps) as a yellow solid.

$^1$H NMR (400 MHz, DMSO-d$_6$): δ 2.15-2.24 (m, 2H), 2.55-2.60 (m, 1H), 2.79-2.87 (m, 1H), 4.83-4.90 (m, 1H), 7.54 (t, J=8.4 Hz, 1H), 7.93 (d, J=8.4 Hz, 1H), 8.01 (d, J=7.2 Hz, 1H), 9.04 (s, 1H), 9.75 (br, 1H), 10.95 (s, 1H).

ESI-MS (EI$^+$, m/z): 273.15.

Example 24: Synthesis of N-(2,6-dioxopiperidin-3-yl)-6-((4-(morpholinomethyl)benzyl)oxy)picolinamide (32)

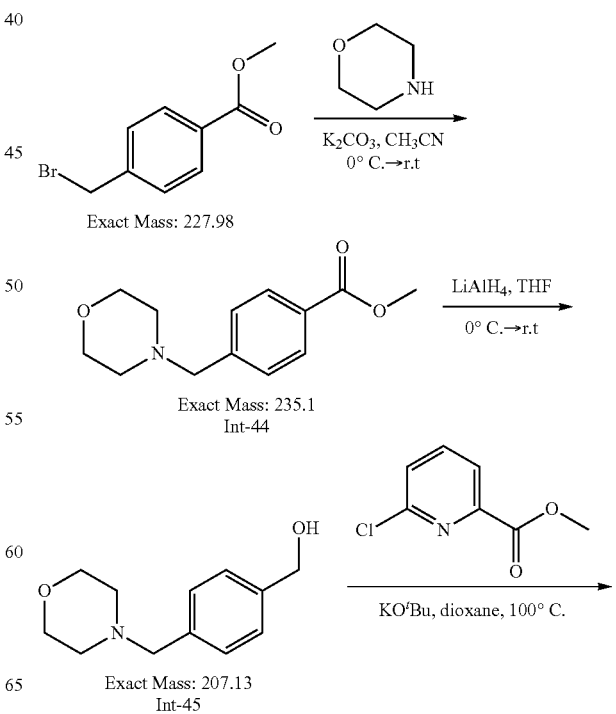

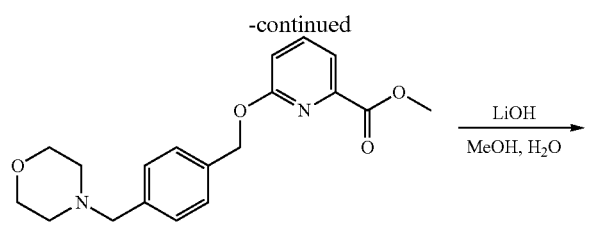

Exact Mass: 342.16
Int-46

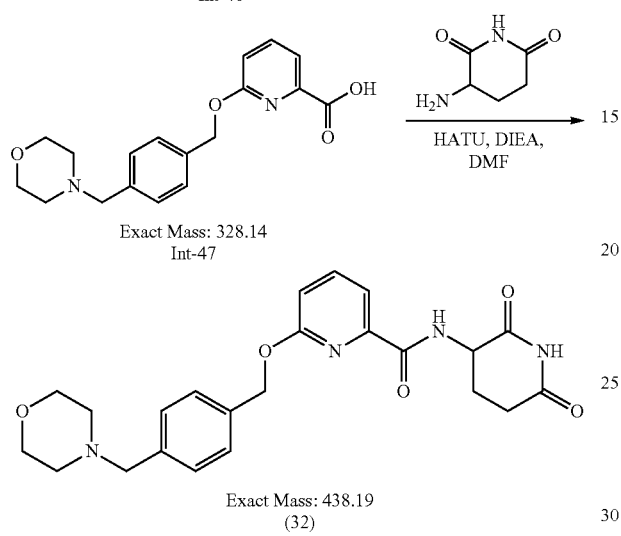

Exact Mass: 328.14
Int-47

Exact Mass: 438.19
(32)

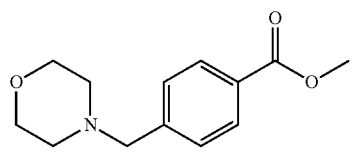 [SMILES: COC(=O)c1ccc(CN2CCOCC2)cc1]

Methyl 4-(morpholinomethyl)benzoate (Int-44)

To a solution of methyl 4-(bromomethyl)benzoate (10 g, 42.6 mmol, 1.0 eq), K₂CO₃ (10.22 g, 74.12 mmol, 1.7 eq) in CH₃CN (95 mL) at 0° C. was added morpholine (4.16 g, 48 mmol, 1.0 eq). The reaction mixture was stirred at room temperature for 3 h. TLC showed that the reaction reached completion. The reaction mixture was filtered through diatomite and the filtrate was concentrated under reduced pressure to give compound Int-44 (9 g, 87%) as a colorless oil.
ESI-MS (EI⁺, m/z): 236.1.

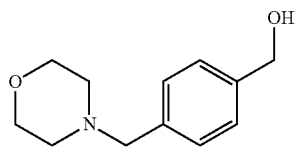 [SMILES: OCc1ccc(CN2CCOCC2)cc1]

(4-(Morpholinomethyl)phenyl)methanol (Int-45)

To a solution of compound Int-44 (9 g, 38.3 mmol, 1.0 eq) in THF (45 mL) was added LiAlH₄ (2.9 g, 76.6 mmol, 2.0 eq) at 0° C. and the mixture was stirred at room temperature for 2 h. TLC showed that the reaction reached completion. The mixture was cooled to 0° C. and quenched with H₂O (2.9 mL), 15% aqueous NaOH. MgSO₄ was added and the mixture was filtered through diatomite. The filter cake was washed with EtOAc (50 mL) and the filtrate was concentrated under reduced pressure to afford compound Int-45 (6.76 g, 85%) as a white solid.

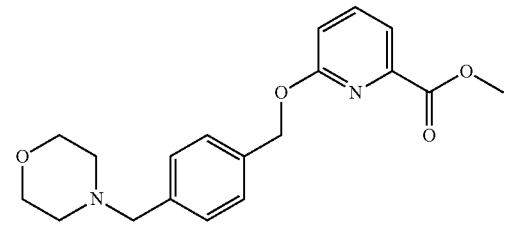 [SMILES: COC(=O)c1cccc(OCc2ccc(CN3CCOCC3)cc2)n1]

Methyl 6-((4-(morpholinomethyl)benzyl)oxy)picolinate (Int-46)

A solution of compound Int-45 (1.5 g, 7.24 mmol, 1.0 eq), methyl 6-chloropicolinate (1.24 g, 7.24 mmol, 1.0 eq), and t-BuOK (810 mg, 7.96 mmol, 1.1 eq) in dioxane (5 mL) was heated to 100° C. for 3 h. TLC showed the reaction reached completion. The solvent was evaporated under reduced pressure and the residue was purified by column chromatography (hexanes/ethyl acetate 30/1) to afford Int-46 (500 mg) as a yellow oil.

¹H NMR (400 MHz, CDCl₃): δ7.63-7.77 (m, 2H), 7.46 (d, J=78.0 Hz, 2H), 7.34 (d, J=8.0 Hz, 2H), 6.97 (d, J=7.8, 1H), 5.44 (s, 2H), 3.97 (s, 3H), 3.70 (t, J=4.8 Hz, 4H), 3.50 (s, 2H), 2.44 (t, J=4.8 Hz, 4H).

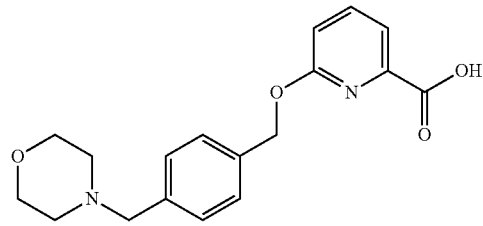 [SMILES: O=C(O)c1cccc(OCc2ccc(CN3CCOCC3)cc2)n1]

6-((4-(Morpholinomethyl)benzyl)oxy)picolinic acid (Int-47)

To a mixture of compound Int-46 (500 mg, 1.46 mmol) in MeOH (2 mL) and H₂O (1 mL) was added LiOH·H₂O (122 mg, 2.92 mmol, 2.0 eq) and the mixture was stirred at room temperature for 4 h. The mixture was concentrated in vacuo and the pH was adjusted to 3-4 with aqueous HCl (1 M). The resulting suspension was filtered and the solid was dried to afford the compound Int-47 (450 mg, 94%) as a white solid.

ESI-MS (EI⁺, m/z): 329.2.

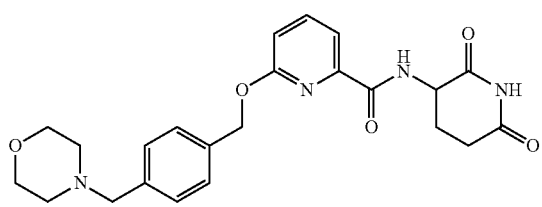 [SMILES: O=C1CCC(NC(=O)c2cccc(OCc3ccc(CN4CCOCC4)cc3)n2)C(=O)N1]

N-(2,6-dioxopiperidin-3-yl)-6-((4-(morpholinomethyl)benzyl)oxy)picolinamide (32)

HATU (136 mg, 0.36 mmol, 1.0 eq) was added to a mixture of the compound Int-47 (100 mg, 0.36 mmol, 1.0 eq), 3-aminopiperidine-2,6-dione hydrochloride (60 mg, 0.36 mmol, 1.0 eq) and DIEA (116 mg, 0.9 mmol, 3.0 eq) in DMF (2 mL) at 0-5° C. The resulting mixture was allowed to warm to room temperature for 1 h. Water was added and the mixture was extracted with EtOAc (2×20 mL). The combined organic layers were washed with water (20 mL) and brine (20 mL), dried over $Na_2SO_4$, and concentrated under reduced pressure. The obtained residue was purified by prep-HPLC to afford compound 32 (72 mg, 54%).

$^1$H NMR (400 MHz, DMSO-$d_6$): δ 10.93 (s, 1H), 10.32 (s, 1H), 8.89 (d, J=8.4 Hz, 1H), 7.91 (t, J=8.0 Hz, 1H), 7.66 (d, J=7.2 Hz, 1H), 7.63 (d, J=8.0 Hz, 2H), 7.54 (d, J=7.6 Hz, 2H), 7.09 (d, J=8.4 Hz, 1H), 5.51-5.61 (m, 2H), 4.78-4.83 (m, 1H), 4.33 (s, 2H), 3.94 (d, J=12.8 Hz, 2H), 3.66 (t, J=12.0 Hz, 2H), 3.24 (d, J=12.8 Hz, 2H), 3.10 (m, 2H), 2.79-2.89 (m, 1H), 2.58 (m, 1H), 2.19-2.30 (m, 1H), 1.98-2.06 (m, 1H).

ESI-MS (EI$^+$, m/z): 439.25.

Example 25: Lenalidomide Displacement Assay

Compounds in Atto565-Lenalidomide displacement assay were dispensed in a 384-well microplate (Corning, 4514) using D300e Digital Dispenser (HP) normalized to 1% DMSO into 10 nM Atto565-Leanlidomide, 100 nM DDB1AB-CRBN, 50 mM Tris pH 7.5, 200 mM NaCl, 0.1% Pluronic® F-68 solution (Sigma). Compound titrations were incubated for 60 min at RT. The change in fluorescence polarization was monitored using a PHERAstar® FS microplate reader (BMG Labtech) for 1 h in 120 s cycles. Data from two independent replicates (n=2) was used to estimate $IC_{50}$ values using variable slope equation in GraphPad Prism 7. The $K_i$ was calculated with probe $K_d$ of 40 nM for the conditions described above following equations described in Nikolovska-Coleska, et al., Analytical Biochemistry 332(2): 261-273 (2004) for competitive model using free concentrations.

The results, shown as $IC_{50}$ and corresponding Ki values, are set forth below in Table 1.

The displacement of the fluorescent probe with compounds 2, 3, 4, 5, 6 and lenalidomide as a control is illustrated in FIG. 1A. The $IC_{50}$ values in [μM] for lenalidomide and compound 5 are shown in the Table 2.

TABLE 1

Lenalidomide Displacement Assay.

| Compound | CRBN Binding $IC_{50}$ [μM] | CRBN Binding $K_i$ [μM] |
|---|---|---|
| 1 | 55 | 15.7 |
| 2 | 30% at 100 μM | |
| 3 | 30% at 100 μM | |
| 4 | 30% at 100 μM | |
| 5 | 113.5 | 32.5 |
| 6 | Inactive | |
| 7 | 29 | 8.3 |
| 8 | 14 | 4 |
| 11 | 50% at 100 μM | |
| 19 | 53 | 15 |
| 20 | 231 | 66 |
| 21 | 72 | 20.6 |
| 22 | 53 | 15 |
| 23 | 2.9 | 0.8 |
| 24 | 7.7 | 2.2 |
| 25 | 17.5 | 5.0 |
| 26 | 50% at 100 μM | |
| 27 | 50% at 100 μM | |
| 28 | inactive | |
| 29 | inactive | |
| 30 | 50% at 100 μM | |
| 31 | 37.6 | 10.7 |
| 32 | 40 | 11.4 |

TABLE 2

$IC_{50}$ value [μM] for compound 5 and lenalidomide.

| Compound | $IC_{50}$ (μM) |
|---|---|
| Compound 5 | 113.5 |
| Lenalidomide | 5.19 |

As shown in FIG. 1A, inventive compounds 3, 4, and 5 showed moderate binding affinity with CRBN with a fluorescence polarization assay as compared to lenalidomide control (lenalidomide $IC_{50}$=5.19 μM in Table 2).

Figure 1B:
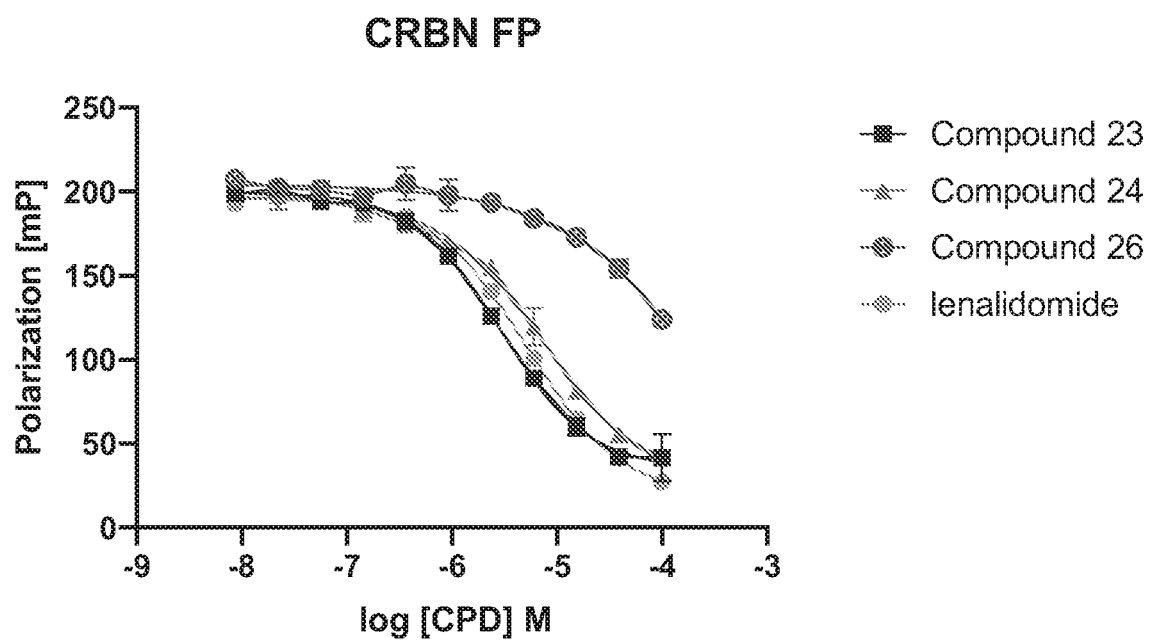
FIG. 1B is a graph that shows cereblon binding (expressed in polarization mP) by various inventive immunomodulatory compounds (inventive compounds 23, 24 and 26) as compared to a control (lenalidomide).

As shown in Table 1 and FIG. 1B, compound 23 resulted in $IC_{50}$ of 2.9 μM, a significant improvement over that of lenalidomide ($IC_{50}$ 5.19 μM in Table 2), an FDA approved binder to CRBN. Compound 24, which is a close analog of compound 23, showed a similar binding affinity ($IC_{50}$ 7.7 μM in Table 2) to that of lenalidomide. Furthermore, 4-NH$_2$ in quinoline of compound 24 to 4-OH substitution in compound 26 significantly reduced the binding affinity from 7.7 μM to weak 50% of probe displacement at 100 μM respectively, as shown in Table 1 and FIG. 1B.

All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A compound having a structure represented by formula (I):

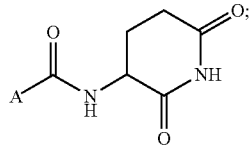

(I)

wherein A represents:

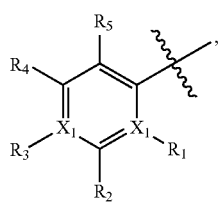

(A₁)

wherein X is C and $X_1$ is N, or

X and $X_1$ are both C, or

X and $X_1$ are both N;

wherein $R_1$ is absent if $X_1$ represents N, and if $X_1$ represents C, $R_1$ represents H, or together with $R_2$ and the other atoms to which they are bound form an optionally substituted 5- or 6-membered carbocyclic group or an optionally substituted 6-membered heterocyclic group;

$R_2$ represents H, halo, hydroxy, optionally substituted C1-C4 alkoxy, 1-benzyl-4-piperidinoxy, optionally substituted 5- or 6-membered carbocyclic group, optionally substituted 5- or 6-membered heterocyclic group, optionally substituted aryl, optionally substituted heteroaryl, or $NR_6R_7$, wherein each of $R_6$ and $R_7$ independently represents H or a substituent or $R_2$ together with $R_1$ and the other atoms to which they are bound form an optionally substituted 5- or 6-membered carbocyclic group or an optionally substituted 6-membered heterocyclic group;

if X represents N, $R_3$ is absent, and if X represents C, $R_3$ independently represents H, halo, hydroxy, optionally substituted amine, 1-benzyl-4-piperidinoxy, optionally substituted 5- or 6-membered carbocyclic group, optionally substituted 5- or 6-membered heterocyclic group, optionally substituted aryl, optionally substituted heteroaryl, or $NR_6R_7$, or wherein $R_2$ and $R_3$, or $R_3$ and $R_4$, together with the atoms to which they are bound form an optionally substituted 6-membered heterocyclic group;

$R_4$, and $R_5$ each independently represents H, halo, hydroxy, optionally substituted amine, 1-benzyl-4-piperidinoxy, optionally substituted 5- or 6-membered carbocyclic group, optionally substituted 6-membered heterocyclic group, optionally substituted aryl, or $NR_6R_7$, or wherein $R_4$ and $R_5$, together with the atoms to which they are bound form an optionally substituted 5- or 6-membered carbocyclic group or an optionally substituted 6-membered heterocyclic group;

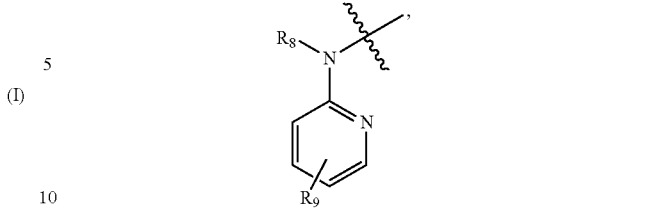

(A₂)

wherein $R_8$ represents H, optionally substituted C1-C4 alkyl, optionally substituted amine, optionally substituted C1-C4 alkoxy, optionally substituted aryl, or an optionally substituted heteroaryl group, and $R_9$ represents H, halo, hydroxy, optionally substituted C1-C4 alkyl, optionally substituted amine, optionally substituted C1-C4 alkoxy, optionally substituted 5- or 6-membered carbocyclic group, or an optionally substituted 5- or 6-membered heterocyclic group;

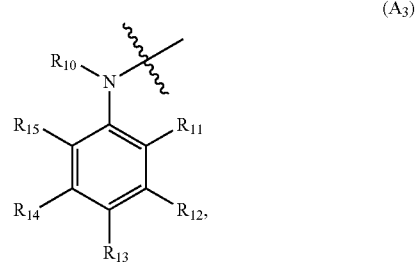

(A₃)

wherein $R_{10}$ represents H, optionally substituted C1-C4 alkyl, optionally substituted amine, optionally substituted C1-C4 alkoxy, optionally substituted aryl, or an optionally substituted heteroaryl group, and $R_{11}$, $R_{12}$, $R_{13}$, $R_{14}$, and $R_{15}$ each independently represents H, halo, hydroxy, optionally substituted C1-C4 alkoxy, optionally substituted aryl, optionally substituted heteroaryl, or $NR_6R_7$, wherein each of $R_6$ and $R_7$ independently represents H or a substituent, or $R_{11}$ together with $R_{12}$ and the other atoms to which they are bound form an optionally substituted 5- or 6-membered carbocyclic group or an optionally substituted 5- or 6-membered heterocyclic group, or $R_{12}$ together with $R_{13}$ and the other atoms to which they are bound form an optionally substituted 5- or 6-membered carbocyclic group or an optionally substituted 5- or 6-membered heterocyclic group, or $R_{13}$ together with $R_{14}$ and the other atoms to which they are bound form an optionally substituted 5- or 6-membered carbocyclic group or an optionally substituted 5- or 6-membered heterocyclic group, or $R_{14}$ together with $R_{15}$ and the other atoms to which they are bound form an optionally substituted 5- or 6-membered carbocyclic group or an optionally substituted 5- or 6-membered heterocyclic group;

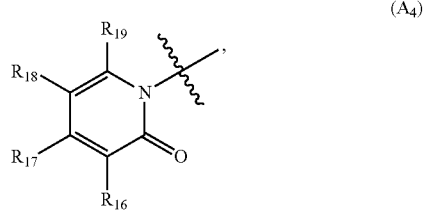

(A₄)

wherein $R_{16}$, $R_{17}$, $R_{18}$ and $R_{19}$ independently represent H or a substituent, or wherein $R_{16}$ and $R_{17}$ together with the atoms to which they are bound form an optionally substituted 5- or 6-membered carbocyclic group, or wherein $R_{16}$ and $R_{17}$ together with the atoms to which they are bound form an optionally substituted 5- or 6-membered carbocyclic group, an optionally substituted 5- or 6-membered heterocyclic group, or wherein $R_{18}$ and $R_{19}$ together with the atoms to which they are bound form an optionally substituted 5- or 6-membered carbocyclic group, or an optionally substituted 5- or 6-membered heterocyclic group; or

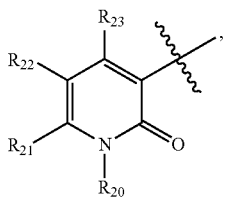

(A$_5$)

wherein $R_{20}$, $R_{21}$, $R_{22}$ and $R_{23}$ independently represent H or a substituent, or wherein $R_{20}$ and $R_{21}$ together with the atoms to which they are bound form an optionally substituted 5- or 6-membered heterocyclic group, or wherein $R_{21}$ and $R_{22}$ together with the atoms to which they are bound form an optionally substituted 5- or 6-membered carbocyclic group, an optionally substituted 5- or 6-membered heterocyclic group, or wherein $R_{22}$ and $R_{23}$ together with the atoms to which they are bound form an optionally substituted 5- or 6-membered carbocyclic group, or an optionally substituted 5- or 6-membered heterocyclic group;

wherein each optional substituent is independently alkyl, alkoxy, alkenyl, alkynyl, carbocyclic, heterocyclic, aryl, heteroaryl, aralkyl, halo, hydroxyl, aryloxy, alkylthio, arylthio, cyano, carbonyl, carboxyl, amino, amido, sulfonyl, or an amino acid, or a pharmaceutically acceptable salt or stereoisomer thereof.

2. The compound of claim 1, wherein A is represented by A$_1$:

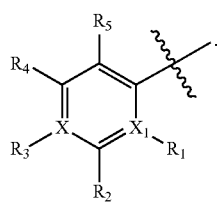

3. The compound of claim 2, wherein X is C and X$_1$ is N, and the compound of formula (I) is represented by formula (Ia):

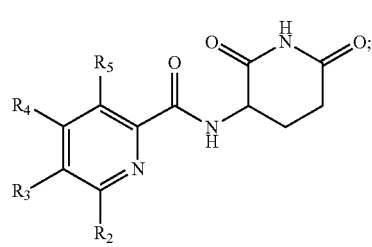

(Ia)

or a pharmaceutically acceptable salt or stereoisomer thereof.

4. The compound of claim 3, wherein not all of $R_2$, $R_3$, $R_4$, and $R_5$ represents H.

5. The compound of claim 3, wherein each of $R_2$, $R_3$, $R_4$, and $R_5$ represents H.

6. The compound of claim 3, wherein one of $R_2$, $R_3$, $R_4$, and $R_5$ represents C5-C6 heterocyclic substituted benzyl or 1-benzyl-4-piperidinoxy.

7. The compound of claim 2, wherein X and X$_1$ are both C, and the compound of formula I is represented by formula (Ib):

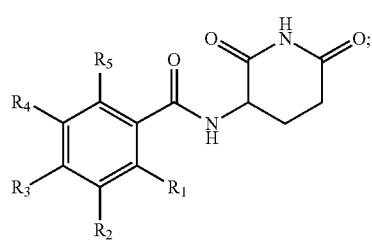

(Ib)

or a pharmaceutically acceptable salt or stereoisomer thereof.

8. The compound of claim 2, wherein X and X$_1$ are both N, and the compound of formula I is represented by formula (Ic):

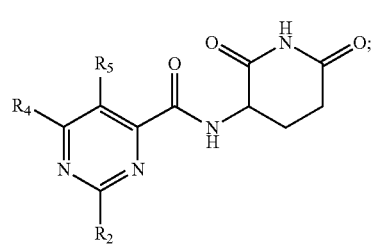

(Ic)

or a pharmaceutically acceptable salt or stereoisomer thereof.

9. The compound of claim 3, wherein at least one of $R_2$, $R_4$ and $R_5$ represents $NR_6R_7$.

10. The compound of claim 8, wherein $NR_6R_7$ is a benzylamino group.

11. The compound of claim 2, wherein at least one of $R_2$, $R_3$, $R_4$ and $R_5$ represents halo, optionally substituted amino, optionally substituted C1-C4 alkoxy or optionally substituted aryl.

12. The compound of claim 2, wherein at least one of $R_2$, $R_3$, $R_4$ and $R_5$ represents methoxy, chloro, amino, benzyloxyamino, benzyloxy, benzyl, or substituted benzyloxy.

13. The compound of claim 11, wherein at least one of $R_2$, $R_3$, $R_4$ and $R_5$ represents benzyloxy substituted with an alkheterocyclic group.

14. The compound of claim 13, wherein the alkheterocyclic group is a morpholino group.

15. The compound of claim 2, wherein $R_2$ represents amino, benzyloxyamino, benzyloxy, substituted benzyloxy, or methoxy.

16. The compound of claim 15, wherein the substituent of the benzyloxy group is a —(CH$_2$)—N-morpholino group.

17. The compound of claim 2, wherein $R_4$ represents chloro.

18. The compound of claim 2, wherein $X_1$ represents C and $R_1$ and $R_2$ together with the atoms to which they are bound form an optionally substituted 6-membered heteroaryl group.

19. The compound of claim 18, wherein the optionally substituted 6-membered heteroaryl group is an optionally substituted pyridyl group.

20. The compound of claim 1, wherein A is represented by $A_2$:

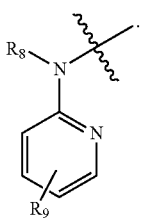

(A$_2$)

21. The compound of claim 20, wherein $R_8$ represents H or methyl and $R_9$ represents hydroxy, NH$_2$, or Cl.

22. The compound of claim 1, wherein A is represented by $A_3$:

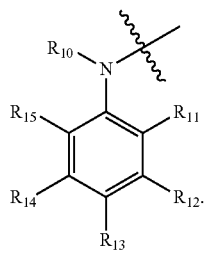

(A$_3$)

23. The compound of claim 22, wherein $R_{10}$ represents H or methyl and $R_{11}$ and $R_{12}$ together with the atoms to which they are bound form an optionally substituted 5-membered heterocyclic group.

24. The compound of claim 1, wherein A is represented by $A_4$:

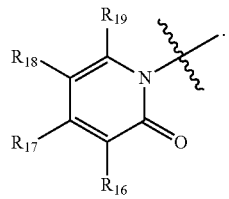

(A$_4$)

25. The compound of claim 24, wherein $R_{16}$ and $R_{17}$ together with the atoms to which they are bound form an optionally substituted 6-membered aryl ring.

26. The compound of claim 25, wherein the optionally substituted 6-membered aryl ring is an optionally substituted phenyl group.

27. The compound of claim 25, wherein the 6-membered aryl ring is unsubstituted.

28. The compound of claim 24, wherein $R_{17}$ and $R_{18}$ together with the atoms to which they are bound form an optionally substituted 6-membered aryl ring.

29. The compound of claim 28, wherein the optionally substituted 6-membered aryl ring is an optionally substituted phenyl group.

30. The compound of claim 28, wherein the 6-membered aryl ring is unsubstituted.

31. The compound of claim 24, wherein $R_{18}$ and $R_{19}$ together with the atoms to which they are bound form an optionally substituted 6-membered aryl ring.

32. The compound of claim 31, wherein optionally substituted 6-membered aryl ring is an optionally substituted phenyl group.

33. The compound of claim 31, wherein the 6-membered aryl ring is unsubstituted.

34. The compound of claim 1, wherein A is represented by $A_5$:

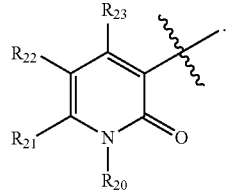

(A$_5$)

35. The compound of claim 4, wherein $R_{20}$ is H, methyl, phenyl, or benzyl, and $R_{21}$, $R_{22}$, and $R_{23}$ are each H.

36. A compound which is:
(1) 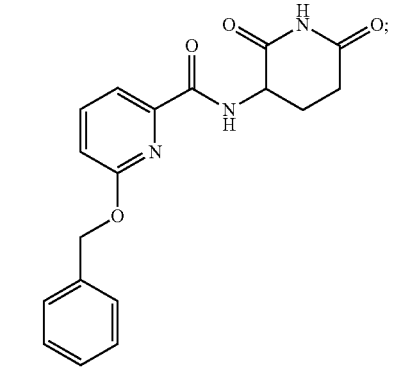
(3) 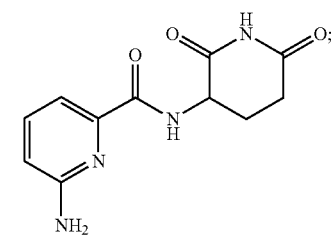
(4) 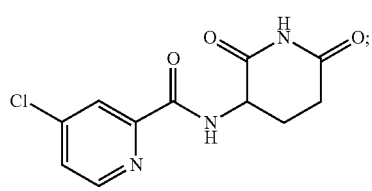
(5) 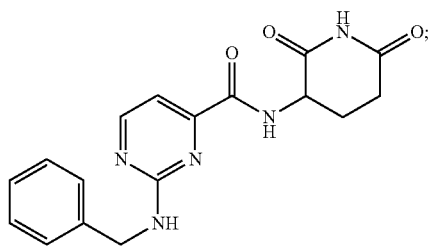
(6) 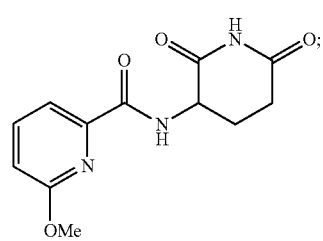
-continued
(7) 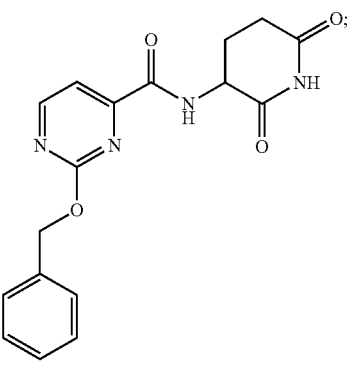
(8) 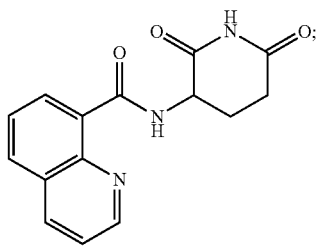
(9) 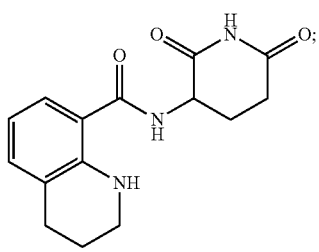
(10) 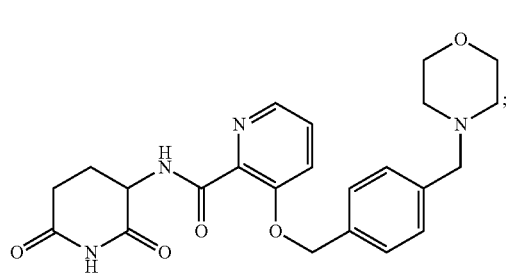
(11) 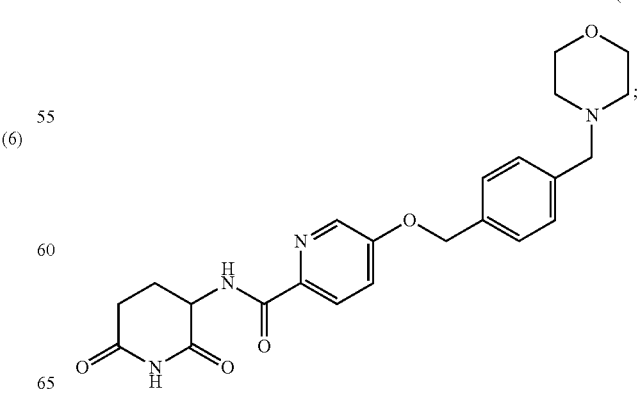

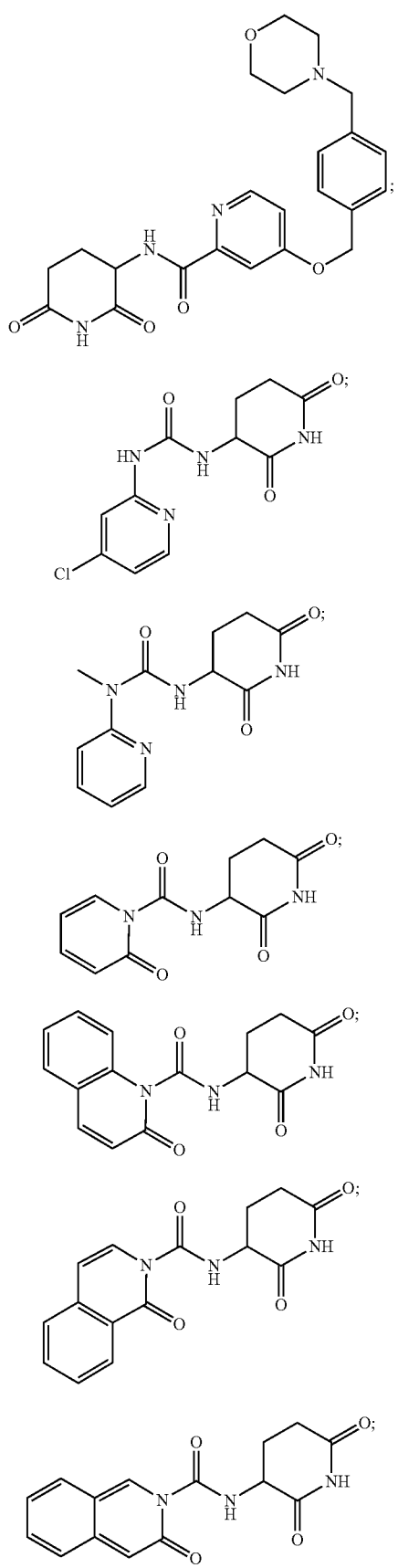
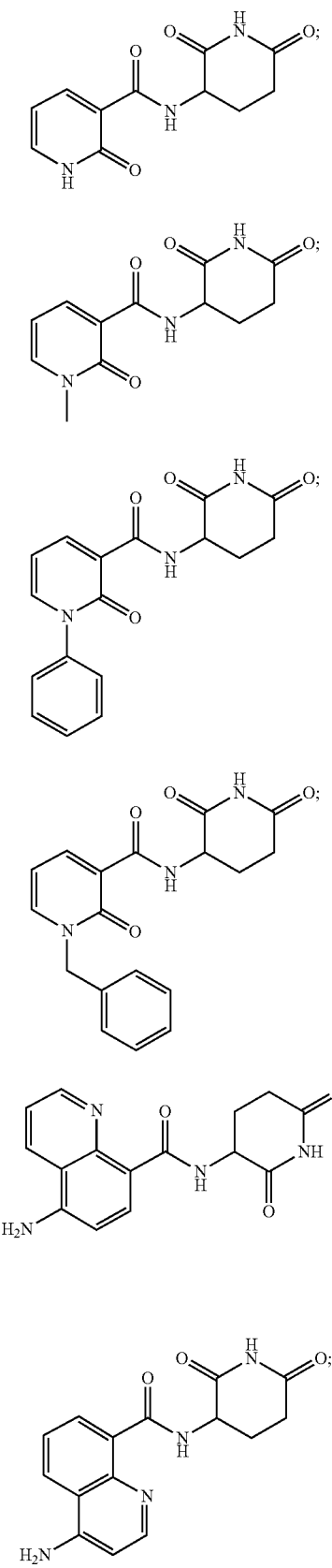

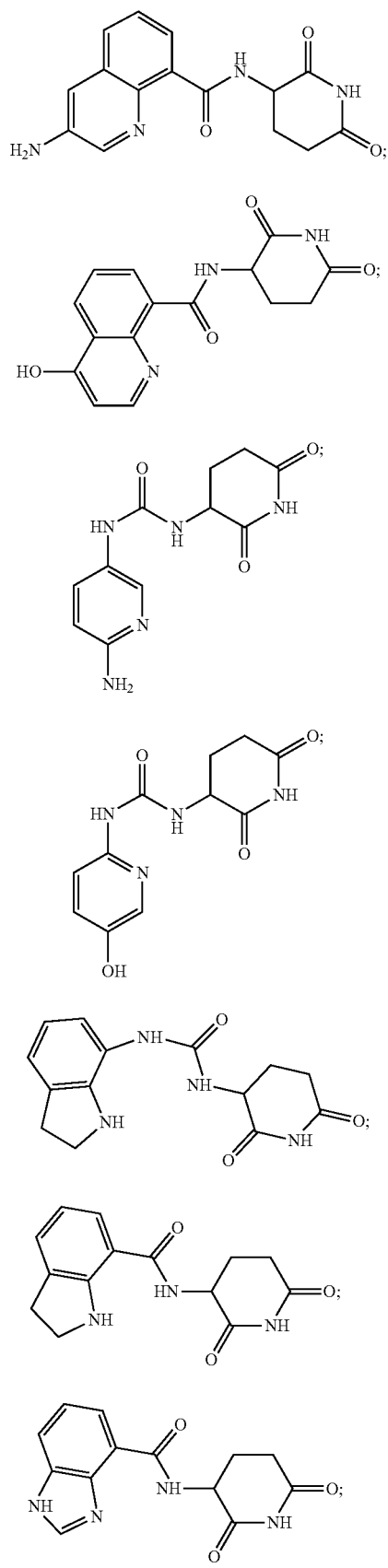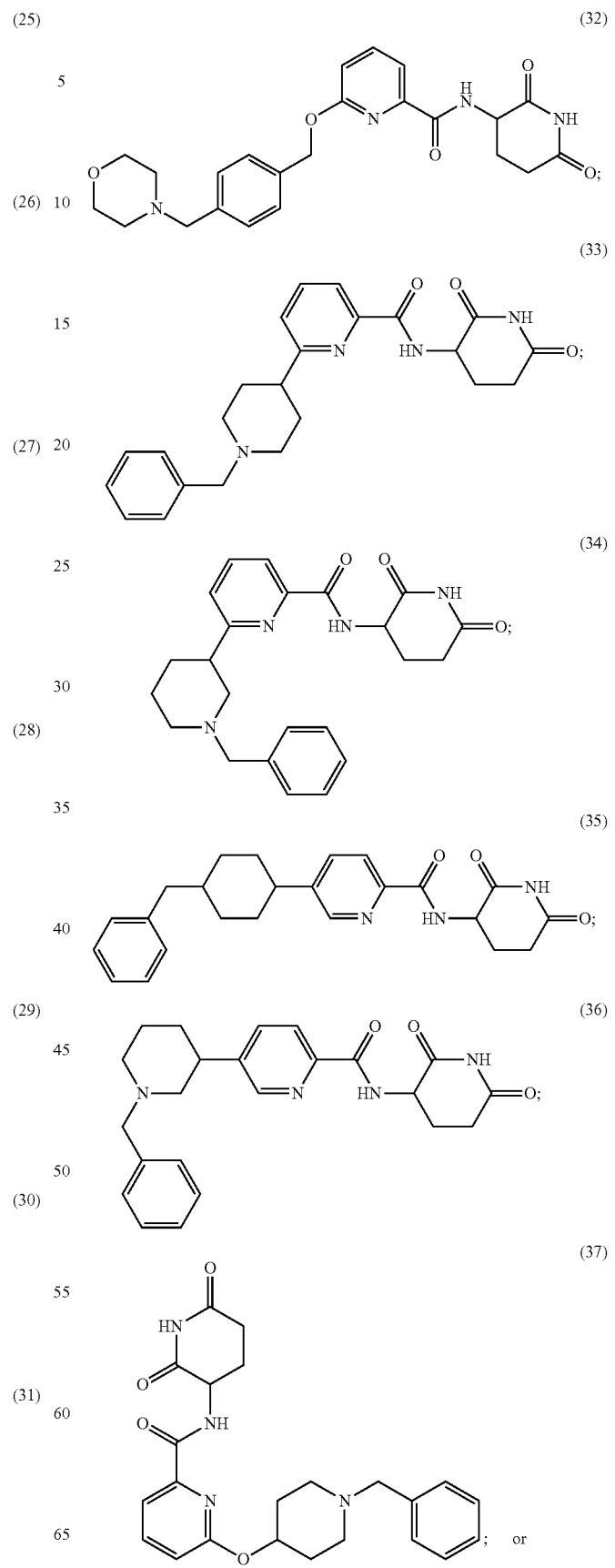

-continued (38)

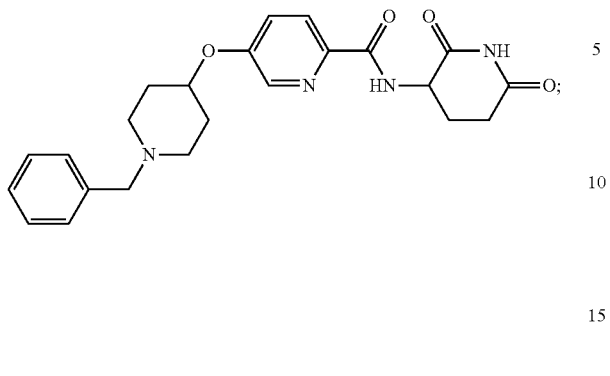

or a pharmaceutically acceptable salt or stereoisomer thereof.

37. A pharmaceutical composition, comprising a therapeutically effective amount of the compound of claim 1 or pharmaceutically acceptable salt or stereoisomer thereof, and a pharmaceutically acceptable carrier.

38. The pharmaceutical composition of claim 37, which is in the form of a capsule or tablet.

39. A method of treating a disease or disorder characterized or mediated by aberrant activity of a protein which is selected from the group consisting of casein kinase 1 alpha (CK1α), family with sequence similarity 83 member F (FAM83F), DTW domain containing 1 (DTWD1), zinc finger protein 91 homolog (ZFP91), ZFP62, ZFP36 ring finger protein like (ZFP36L2), ring finger protein 166 (RNF166), Ikaros family zinc finger protein 1 (IKZF1), IKZF2, IKZF3, IKZF4, IKZF5, Ras-related protein Rab-28 (RAB28), glutathione S-transferase pi 1 (GSTP1), GSPT2, mitochondrial import inner membrane translocase subunit Tim10 (TIMM10), GDNF inducible zinc finger protein 1 (GZF1), early growth response 1 (EGR1), hypermethylated in cancer 1 (HIC1), HIC2, insulinoma-associated protein 2 (INSM2), odd-skipped related transcription factor 2 (OSR2), protein polybromo-1 (PB1), PR domain zinc finger protein 15 (PRD15), spalt like transcription factor 1 (SALL1), SALL3, SALL4, WIZ, zinc finger and BTB domain-containing protein 17 (ZBT17), ZBT41, ZBT49, ZBT7A, ZBT7B, ZBTB2, ZBTB39, zinc finger protein interacting with K protein 1 (ZIK1), zinc finger protein 3 (ZNF3), ZNF217, ZNF276, ZNF316, ZNF324B, ZNF335, ZNF397, ZNF407, ZNF408, ZNF462, ZNF483Or, SNF517, ZNF526, ZNF581, ZNF587, ZNF589, ZNF618, ZNF644, ZNF646, ZNF653, ZNF654, ZNF692, ZNF724, ZNF771, ZNF782, ZNF784, ZNF814, zinc finger and SCAN domain containing 10 (ZSC10), ZSC22, ZC827, and zinc finger with UFM1-specific peptidase domain (ZUFSP), comprising administering to a subject in need thereof a therapeutically effective amount of the compound of claim 1 or a pharmaceutically acceptable salt or stereoisomer thereof.

40. The method of claim 39, wherein the disease is multiple myeloma.

41. The compound of claim 39, wherein the disease or disorder is characterized or mediated by aberrant activity of IKZF2.

42. The compound of claim 36, which is (8)
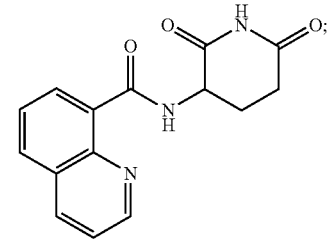

(23)
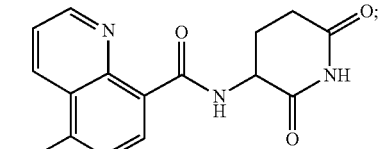

(24)
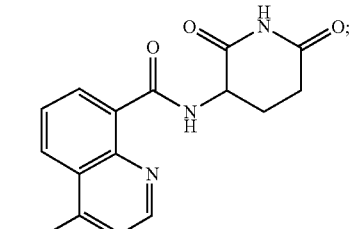

(25)
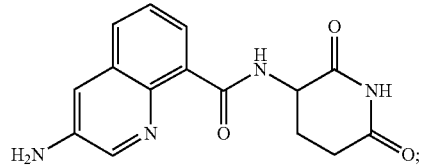

(26)
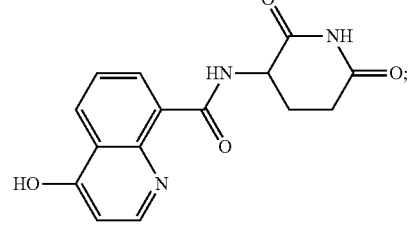

(30)
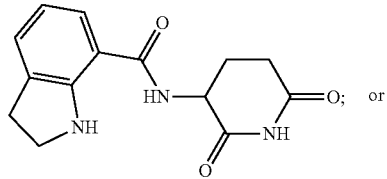
or

(31)
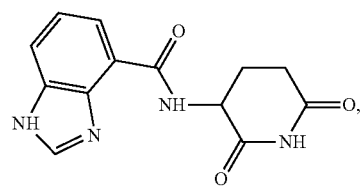

or a pharmaceutically acceptable salt or stereoisomer thereof.

* * * * *

UNITED STATES PATENT AND TRADEMARK OFFICE
CERTIFICATE OF CORRECTION

PATENT NO. : 12,234,220 B2
APPLICATION NO. : 17/255738
DATED : February 25, 2025
INVENTOR(S) : Nathanael Gray et al.

Page 1 of 2

It is certified that error appears in the above-identified patent and that said Letters Patent is hereby corrected as shown below:

In the Claims

In Column 87, Lines 16-25:
Delete the following structure:

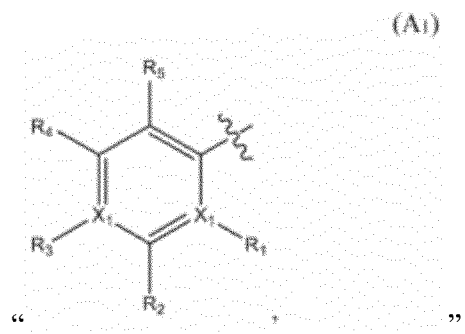

"                    *                    "

Replace with the following structure:

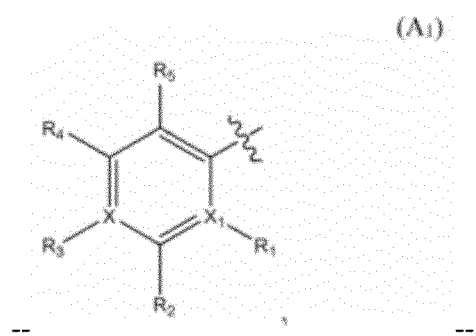

--                    *                    --

Signed and Sealed this
Twenty-fifth Day of March, 2025

Coke Morgan Stewart
*Acting Director of the United States Patent and Trademark Office*

CERTIFICATE OF CORRECTION (continued)
U.S. Pat. No. 12,234,220 B2

Page 2 of 2

In Column 98, Lines 36-43:
Delete the following structure:

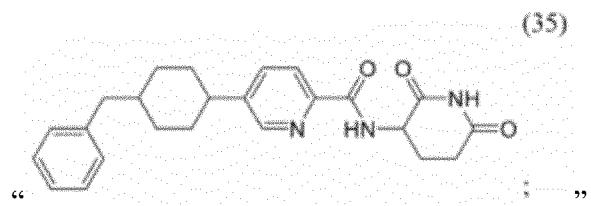

" ; "

Replace with the following structure:

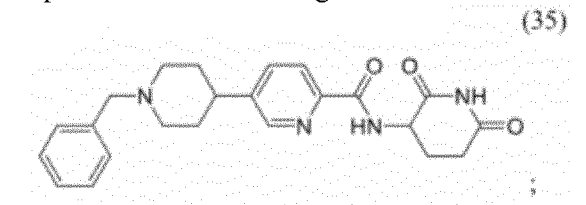

-- ; --